(12) United States Patent
Zhang et al.

(10) Patent No.: US 7,144,885 B2
(45) Date of Patent: Dec. 5, 2006

(54) FUSED TRICYCLIC HETEROCYCLES USEFUL FOR TREATING HYPER-PROLIFERATIVE DISORDERS

(75) Inventors: Chengzhi Zhang, Orange, CT (US); Michael Burke, New Haven, CT (US); Zhi Chen, Hamden, CT (US); Jacques Dumas, Bethany, CT (US); Dongping Fan, North Haven, CT (US); Benjamin D. Jones, Hamden, CT (US); Gaetan Ladouceur, Guilford, CT (US); Wendy Lee, Hamden, CT (US); Barton Phillips, New Haven, CT (US); Scott M. Wilhelm, Orange, CT (US); Qian Zhao, Wallingford, CT (US)

(73) Assignee: Bayer Pharmaceuticals Corporation, West Haven, CT (US)

( * ) Notice: Subject to any disclaimer, the term of this patent is extended or adjusted under 35 U.S.C. 154(b) by 110 days.

(21) Appl. No.: 10/501,690

(22) PCT Filed: Feb. 21, 2003

(86) PCT No.: PCT/US03/05395

§ 371 (c)(1),
(2), (4) Date: Jul. 17, 2004

(87) PCT Pub. No.: WO03/072566

PCT Pub. Date: Sep. 4, 2003

(65) Prior Publication Data

US 2005/0165042 A1    Jul. 28, 2005

Related U.S. Application Data

(60) Provisional application No. 60/399,886, filed on Jul. 31, 2002, provisional application No. 60/359,011, filed on Feb. 22, 2002.

(51) Int. Cl.
*A61K 31/497* (2006.01)
*A61K 31/4355* (2006.01)
*A61K 31/4436* (2006.01)
*A61K 31/443* (2006.01)
*A61K 31/427* (2006.01)

(52) U.S. Cl. ............... 514/255.05; 514/291; 514/337; 514/365; 514/374; 514/443; 514/450; 514/454; 514/463; 514/468; 546/83; 546/284.1; 548/200; 548/236; 549/43; 549/57; 549/350; 549/387; 549/433; 549/436; 549/458; 544/405

(58) Field of Classification Search ............... 549/43, 549/57, 350, 387, 433, 436, 458; 548/200, 548/236; 544/405; 546/83, 284.1
See application file for complete search history.

(56) References Cited

U.S. PATENT DOCUMENTS 5,466,810 A    11/1995    Godfrey ............... 546/202
5,504,213 A    4/1996    Fischer ............... 548/253
5,565,488 A    10/1996    Braunlich ............... 514/469
5,622,989 A    4/1997    Braunlich ............... 514/469
5,691,359 A    11/1997    Fischer ............... 514/337
5,922,740 A    7/1999    Braunlich ............... 514/337

FOREIGN PATENT DOCUMENTS

| EP | 0551662 | 7/1993 |
|---|---|---|
| EP | 0731099 | 9/1996 |
| EP | 0885893 | 12/1998 |
| WO | 9802440 | 1/1998 |
| WO | 0069841 | 11/2000 |
| WO | 0069842 | 11/2000 |
| WO | 0069843 | 11/2000 |
| WO | 0069844 | 11/2000 |

OTHER PUBLICATIONS

Patent Abstracts of Japan, vol. 009, No. 205 (C-299), Aug. 22, 1985 and JP 60 072880 A (Kaken Seiyaku KK), Apr. 24, 1985.
Hayakawa, et al., "4-Hydroxy-3-Methyl-6-Phenylbenzofuran-2-Carboxylic Acid Ethyl Ester Derivatives as Potent Anti-Tumor Agents," *Bioorg. Med. Chem. Lett.*, 14, 455-458 (2004).
Hayakawa, et al., "A Library Synthesis of 4-Hydroxy-3-Methyl-6-Phenylbenzofuran-2-Carboxylic Acid Ethyl Ester Derivatives as Anti-Tumor Agents," *Bioorg. Med. Chem. Lett.*, 14, 4383-4387 (2004).
Hayakawa, et al., "Thienopyridine and Benzofuran Derivatives as Potent Anti-Tumor Agents Possessing Different Structure-Activity Relationships," *Bioorg. Med. Chem. Lett.*, 14, 3411-3414 (2004).

*Primary Examiner*—Kamal A. Saeed
*Assistant Examiner*—Jason M. Nolan

(57) ABSTRACT

This invention relates to a novel fused tricyclic heterocycle of the formula (Ia, Ib) and its use for the treatment of hyper-proliferative disorders

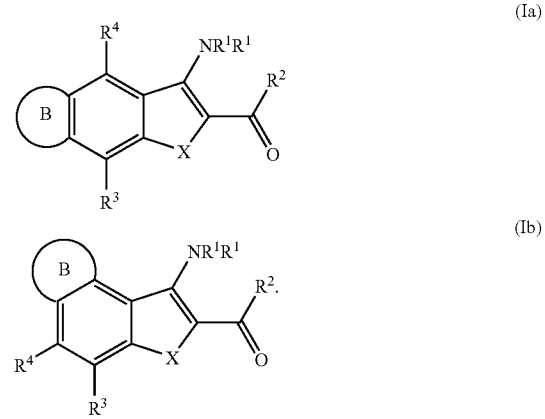

26 Claims, No Drawings

FUSED TRICYCLIC HETEROCYCLES USEFUL FOR TREATING HYPER-PROLIFERATIVE DISORDERS

FIELD OF THE INVENTION

This invention relates to novel fused tricyclic heterocyclic compounds, pharmaceutical compositions containing such compounds, and the use of those compounds and/or compositions for treating hyper-proliferative disorders.

DESCRIPTION OF THE INVENTION

Compounds of the Invention

One embodiment of this invention relates to a compound selected from Formula Ia and Formula Ib

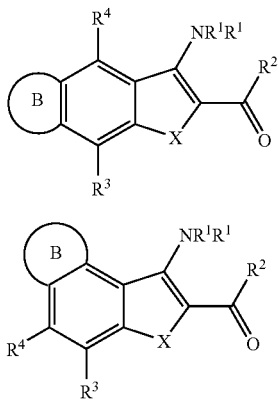

where

X is O or S;

$R^1$ is in each instance independently selected from H, $C_1$–$C_6$ alkyl, benzoyl, and $C(O)R^A$;

$R^A$ is in each instance independently H, $(C_1$–$C_6)$alkoxy, $NR^B R^B$, or $(C_1$–$C_6)$alkyl, said alkyl being optionally substituted with OH, =O, $(C_1$–$C_3)$alkoxy, $C(O)R^B$, halo and $NR^B R^B$;

$R^B$ is in each instance independently H, $(C_3$–$C_6)$cycloalkyl, and $(C_1$–$C_6)$alkyl, said alkyl being optionally substituted with OH, =O, halo, $(C_1$–$C_6)$alkoxy, $NH(C_1$–$C_3)$alkyl, $N[(C_1$–$C_3)$alkyl$]_2$, $NC(O)(C_1$–$C_3)$alkyl and phenyl, and where $R^B$, when it is attached to a N atom, is in each instance $(C_1$–$C_4)$alkyl, then the 2 $(C_1$–$C_4)$alkyl groups, taken together with the N atom to which they are attached, may be joined together to form a saturated ring, and where $R^B$ and $R^B$ together with the N to which they are attached may form a morpholinyl ring or a piperazinyl ring optionally substituted on the available N atom with $(C_1$–$C_6)$alkyl, said alkyl being optionally substituted with OH, =O, $NH_2$, $NH(C_1$–$C_3)$alkyl, $N[(C_1$–$C_3)$alkyl$]_2$, and $(C_1$–$C_6)$alkoxy, and with the proviso that when $R^B$ is attached to S(O) or to $S(O)_2$, it cannot be H;

$R^2$ is selected from phenyl and naphthyl, each optionally substituted with 1, 2, or 3 substituents each independently selected from OH, CN, $NO_2$, $(C_1$–$C_6)$alkyl, $(C_1$–$C_6)$alkoxy, $(C_3$–$C_6)$ cycloalkyl, halo, halo$(C_1$–$C_6)$alkyl, halo$(C_1$–$C_6)$ alkoxy, $C(O)R^A$, $C(O)NR^B R^B$, $NR^B R^B$, $NH[(C_1$–$C_6)$ alkyl$]_{0-1}S(O)_2R^B$, $NH[(C_1$–$C_6)$alkyl$]_{0-1}C(O)R^A$, and $NH[(C_1$–$C_6)$alkyl$]_{0-1}C(O)OR^B$, a heterocycle selected from a six membered heterocycle, a five membered heterocycle and a fused bicyclic heterocycle, each heterocycle being optionally substituted with 1, 2 or 3 substituents each independently selected from OH, CN, $NO_2$, $(C_1$–$C_6)$alkyl, $(C_3$–$C_6)$ cycloalkyl, $(C_1$–$C_6)$alkoxy, halo, halo$(C_1$–$C_6)$alkyl, halo$(C_1$–$C_6)$alkoxy, $C(O)R^A$, $C(O)NR^B R^B$, $NR^B R^B$, $NH[(C_1$–$C_6)$alkyl$]_{0-1}S(O)_2R^B$, $NH[(C_1$–$C_6)$alkyl$]_{0-1}C(O)R^A$, and $NH[(C_1$–$C_6)$alkyl$]_{0-1}C(O)OR^B$, $R^3$ and $R^4$ are each independently selected from H, halo, OH, CN, $(C_1$–$C_3)$alkoxy, $(C_1$–$C_3)$alkyl, halo$(C_1$–$C_3)$alkoxy and halo$(C_1$–$C_3)$alkyl with the proviso that when X in Formula Ib is S, then $R^4$ cannot be $(C_1$–$C_3)$alkyl;

B is a 5 or 6 membered cyclic moiety being optionally substituted with 1 or 2 substituents each independently selected from =O, OH, N oxide, halo, halo$(C_1$–$C_6)$alkyl, halo$(C_1$–$C_6)$alkoxy, $(C_1$–$C_6)$alkyl, $(C_1$–$C_3)$alkylphenyl, $(C_1$–$C_6)$alkoxy, $C(O)R^A$, $C(O)OR^B$, $C(O)NR^B R^B$, $NR^B R^B$, $NH[(C_1$–$C_6)$alkyl$]_{0-1} S(O)_2R^B$, and $NH[(C_1 C_6)$ alkyl$]_{0-1}C(O)R^A$;

or a pharmaceutically acceptable salt or ester thereof.

The terms identified above have the following meaning throughout:

The term "optionally substituted" means that the moiety so modified may have from none to up to about the highest number of substituents indicated. When there are two or more substituents on any moiety, each substituent is defined independently of any other substituent and can, accordingly, be the same or different.

The term "$(C_1$–$C_6)$alkyl, said alkyl being optionally substituted" means an alkyl group as defined below wherein each C atom is bonded to 0, 1, 2 or 3H atoms, as appropriate, and any up to all H atoms may be replaced with a recited substituent, with the proviso that combinations of recited substituents result in a chemically stable compound.

The terms "$(C_1$–$C_6)$alkyl", "$(C_1$–$C_4)$alkyl", and "$(C_1$–$C_3)$ alkyl" mean linear or branched saturated carbon groups having from about 1 to about 3, 4, or 6 C atoms respectively. Such groups include but are not limited to methyl, ethyl, n-propyl, isopropyl, n-butyl, isobutyl, sec-butyl, tert-butyl, and the like.

The terms "$(C_1$–$C_6)$alkoxy" and "$(C_1$–$C_3)$alkoxy" mean a linear or branched saturated carbon group having from about 1 to about 6 or 3 C atoms, respectively, said carbon group being attached to an O atom. The O atom is the point of attachment of the alkoxy substituent. Such groups include but are not limited to methoxy, ethoxy, n-propoxy, isopropoxy, n-butoxy, isobutoxy, sec-butoxy, tert-butoxy, and the like.

The term "$C_3$–$C_6$ cycloalkyl" means a saturated monocyclic alkyl group of from 3 to about 6 carbon atoms and includes such groups as cyclopropyl, cyclopentyl, cyclohexyl, and the like.

The term "halo" means an atom selected from Cl, Br, F and I, where Cl, Br and F are preferred and Cl and F are most preferred.

The terms "halo$(C_1$–$C_6)$alkyl" and "halo$(C_1$–$C_3)$alkyl" mean a linear or branched saturated carbon group having from about 1 to about 6 or 3 C atoms respectively that is substituted with at least 1 and up to perhalo (that is, up to 3 per C atom, as appropriate) Cl or F atoms selected in each instance independently from any other Cl or F atom. Such groups include but are not limited to trifluoromethyl, trichloromethyl, pentafluoroethyl, fluorobutyl, 6-chlorohexyl, and the like.

The terms "halo($C_1$–$C_6$)alkoxy" and "halo($C_1$–$C_3$) alkoxy" mean a linear or branched saturated carbon group having from about 1 to about 6 or 3 C atoms, respectively, said carbon group being attached to an O atom and being substituted with at least 1 and up to perhalo (that is, up to 3 per C atom, as appropriate) Cl or F atoms selected in each instance independently from any other Cl or F atom. Such groups include but are not limited to trifluoromethoxy, trichloromethoxy, pentafluoroethoxy, fluorobutoxy, 6-chlorohexoxy, and the like.

The term "six membered heterocycle" means an aromatic ring made of 6 atoms, 1, 2, or 3 of which are N atoms, the rest being C, where the heterocycle is attached to the core molecule at any available C atom and is optionally substituted at any available C atom with the recited substituents. Such groups include pyridine, pyrimidine, pyridazine and triazine in all their possible isomeric forms.

The term "five membered heterocycle" means an aromatic ring made of 5 atoms and having 1, 2 or 3 heteroatom(s) each selected independently from O, N, and S, the rest being C atoms, with the proviso that there can be no more than 2 O atoms in the heterocycle and when there are 2 O atoms they must be nonadjacent. This heterocycle is attached to the core molecule at any available C atom and is optionally substituted at any available C or N atom with the recited substituents. Such groups include pyrrole, furan, thiophene, imidazole, pyrazole, thiazole, oxazole, isoxazole, isothiazole, triazole, oxadiazole, thiadiazole, and tetrazole in all their possible isomeric forms.

The term "fused bicyclic heterocycle" means a group having from 9 to 12 atoms divided into 2 rings that are fused together through adjacent C atoms where 1, 2, or 3 of the remaining atoms are heteroatoms each independently selected from N, O, and S. The heteroatoms may be located at any available position on the fused bicyclic moiety with the proviso that there can be no more than 2 O atoms in any fused bicyclic heterocycle, and when 2 O atoms are present, they must not be adjacent. At least one of the two fused rings must be aromatic. The other ring, if it were not fused to the aromatic ring, may be aromatic, partially saturated or unsaturated. An aromatic ring is always attached to the core molecule through any available C atom. The fused bicyclic heterocycle is optionally substituted at any available C atom with the recited substituents. Such groups include 5-5, 5-6, and 6-6 fused bicycles, where one of the rings is one of the heterocycles described above and the second ring is either benzene or another heterocycle including, but not limited to, chroman, chromene, benzofuran, benzthiophene, quinoline, isoquinoline, phthalazine, naphthyridine, quinoxaline, purine, indole, indazole, isoindole, indolizine, cinnoline, pteridine, isoindole, thienofuran, imidazothiazole, dithianaphthalene, benzoxazine, piperonyl, and the like.

The term "B is a 5 or 6 membered cyclic moiety" means a partially unsaturated or an aromatic ring having about 5 or 6 atoms respectively, said ring having all C atoms or having 1 or 2 heteroatoms selected from O, N and S, with the proviso that there can be no more than 2 O atoms in any heterocyclic moiety and when there are 2 O atoms, they must be non-adjacent. The term "partially unsaturated" used in relation to B includes a ring as described above, that, if it stood alone and was not fused to the core molecule, could be saturated. That is, the ring may be, by itself, a saturated ring but, when fused to the core molecule, becomes partially saturated. The cyclic moiety is fused to the core molecule through any 2 adjacent C atoms and is optionally substituted at any available C or N atom with the recited substituents. Such cyclic moieties include but are not limited to cyclopentyl, cyclohexyl, include pyrrole, furan, thiophene, imidazole, pyrazole, thiazole, oxazole, isoxazole, oxazine, isothiazole, pyridine, pyrimidine, pyridazine, pyrazoline, piperidine, piperazine, pyrrolidine, imidazolidine, imidazoline, and the like, in all their possible isomeric forms.

The term "N-oxide" means that for heterocycles containing an otherwise unsubstituted $sp^2$ N atom, the N atom may bear a covalently bound O atom, i.e., —N(->O). Examples of such N-oxide substituted heterocycles include pyridyl N-oxides, pyrimidyl N-oxides, pyrazinyl N-oxides and pyrazolyl N-oxides.

The term "Formula I" means, severally and collectively, Formula Ia and Formula Ib.

Representative compounds of Formula Ia and Formula Ib are disclosed later herein.

The compounds of this invention may contain one or more asymmetric centers, depending upon the location and nature of the various substituents desired. Asymmetric carbon atoms may be present in the (R) or (S) configuration or (R,S) configuration. In certain instances, asymmetry may also be present due to restricted rotation about a given bond, for example, the central bond adjoining two substituted aromatic rings of the specified compounds. Substituents on a ring may also be present in either cis or trans form, and a substituent on a double bond may be present in either Z or E form. It is intended that all such configurations (including enantiomers and diastereomers) are included within the scope of the present invention. Preferred compounds are those with the absolute configuration of the compound of this invention which produces the more desirable biological activity. Separated, pure or partially purified isomers or racemic mixtures of the compounds of this invention are also included within the scope of the present invention.

The use of pharmaceutically acceptable salts of the compounds of this invention are also within the scope of this invention. The term "pharmaceutically acceptable salt" refers to either inorganic or organic acid or base salts of a compound of the present invention that have properties acceptable for the therapeutic use intended. For example, see S. M. Berge, et al. "Pharmaceutical Salts," *J. Pharm. Sci.* 1977, 66, 1–19.

Representative salts of the compounds of this invention include the conventional non-toxic salts and the quaternary ammonium salts that are formed, for example, from inorganic or organic acids or bases by means well known in the art. For example, such acid addition salts include acetate, adipate, alginate, ascorbate, aspartate, benzoate, benzenesulfonate, bisulfate, butyrate, citrate, camphorate, camphorsulfonate, cinnamate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, itaconate, lactate, maleate, mandelate, methanesulfonate, 2-naphthalenesulfonate, nicotinate, nitrate, oxalate, pamoate, pectinate, persulfate, 3-phenylpropionate, picrate, pivalate, propionate, succinate, sulfonate, tartrate, thiocyanate, tosylate, and undecanoate. The term acid addition salts also comprises the hydrates and the solvent addition forms which the compounds of this invention are able to form. Examples of such forms are, for example, hydrates, alcoholates and the like.

Base salts include alkali metal salts such as potassium and sodium salts, alkaline earth metal salts such as calcium and magnesium salts, and ammonium salts with organic bases such as dicyclohexylamine and N-methyl-D-glucamine. Additionally, basic nitrogen containing groups may be quaternized with such agents as lower alkyl halides such as methyl, ethyl, propyl, and butyl chlorides, bromides and iodides; dialkyl sulfates including dimethyl, diethyl, and dibutyl sulfate; and diamyl sulfates, long chain halides such as decyl, lauryl, myristyl and strearyl chlorides, bromides and iodides, aralkyl halides including benzyl and phenethyl bromides, and others.

The esters of appropriate compounds of this invention are pharmaceutically acceptable esters such as alkyl esters, including methyl, ethyl, propyl, isopropyl, butyl, isobutyl or pentyl esters, and the like. Additional esters such as phenyl-($C_1$–$C_5$)alkyl may be used, although methyl ester is preferred.

Unless the context clearly indicates to the contrary, whenever the term "compounds of this invention," "compounds of the present invention", and the like, are used herein, they are intended to include the chemically feasible pharmaceutically acceptable salts and/or esters as well as all stereoisomeric forms of the referenced compounds.

Method of Making the Compounds of the Present Invention

Proton ($^1$H) nuclear magnetic resonance (NMR) spectra were measured with a General Electric GN-Omega 300 (300 MHz) spectrometer with either $Me_4Si$ (δ 0.00) or residual protonated solvent ($CHCl_3$ δ 7.26; MeOH δ 3.30; DMSO δ 2.49) as standard. Carbon ($^{13}$C) NMR spectra were measured with a General Electric GN-Omega 300 (75 MHz) spectrometer with solvent ($CDCl_3$ δ 77.0; $d_3$-MeOD; δ 49.0; $d_6$-DMSO δ 39.5) as standard.

Chiral separations were performed using a commercially available Chiracel® AD HPLC column, eluting with a gradient of isopropanol in hexane (from 1% to 15%) with addition of 0.1% trifluoroacetic acid.

DEFINITIONS

When the following abbreviations are used herein, they have the following meaning:
ADDP 1,1'-(azodicarbonyl)-dipiperidine
DBU 1,8-Diazabicyclo[5.4.0]undec-7-ene
DMF N,N-dimethylformamide
DMSO Dimethylsulfoxide
EA Elemental analysis
ES Electrospray
Et Ethyl
$Et_2O$ Diethyl ether
EtOAc Ethyl acetate
GC-MS Gas chromatography-mass spectroscopy
HEX Hexanes
LC-MS Liquid Chromatography/Mass Spectroscopy
Me Methyl
MeCN Acetonitrile
MeOH Methanol
MPLC Medium Pressure Liquid Chromatograph
NCS N-chlorosuccinimide
NMR Nuclear Magnetic Resonance Spectroscopy
Ph Phenyl
PyBOP Benzotriazole-1-yl-oxy-tris-pyrrolidino-phosphonium hexafluorophosphate
RT (RT) Retention time (HPLC)
Rf TLC Retention Factor
rt Room temperature
THF Tetrahydrofuran
TLC Thin layer chromatography In general, the compounds of this invention may be prepared by standard techniques known in the art, by known processes analogous thereto, and/or by processes disclosed below, using starting materials which are either commercially available, producible according to routine, conventional chemical methods or the synthesis of which is described herein. The particular process to be utilized in the preparation of a compound of this invention depends upon the specific compound desired. Such factors as whether the amine is substituted or not, the selection of the specific substituents possible at various locations on the molecule, and the like, each play a role in the path to be followed. Those factors are readily recognized by one of ordinary skill in the art.

The general method used to prepare the compounds in this invention is illustrated in Reaction Scheme 1 below. The amino benzofuran or benzothiophene compounds of formula (Ia) or (Ib) may be synthesized by the condensation of haloketone of formula (IIa) or (IIb) and a properly substituted 2-cyanophenol (X=O) or thiophenol (X=S), and 1-aryl-2-halo-ethanone (III). The reaction conditions may be carried out under basic conditions (such as cesium carbonate, potassium carbonate, sodium carbonate, DBU), in a solvent such as DMF and MeCN, and at temperatures between room temperature to 100° C. The components IIa, IIb, and III, can be prepared but not limited to the methods described below. The various means that used to prepare components (III) were summarized in method I, to prepare components IIa and IIb were summarized in method II, the synthesis of benzofuran core were summarized in method III, and the synthesis of benzothiophene core were summarized in method IV.

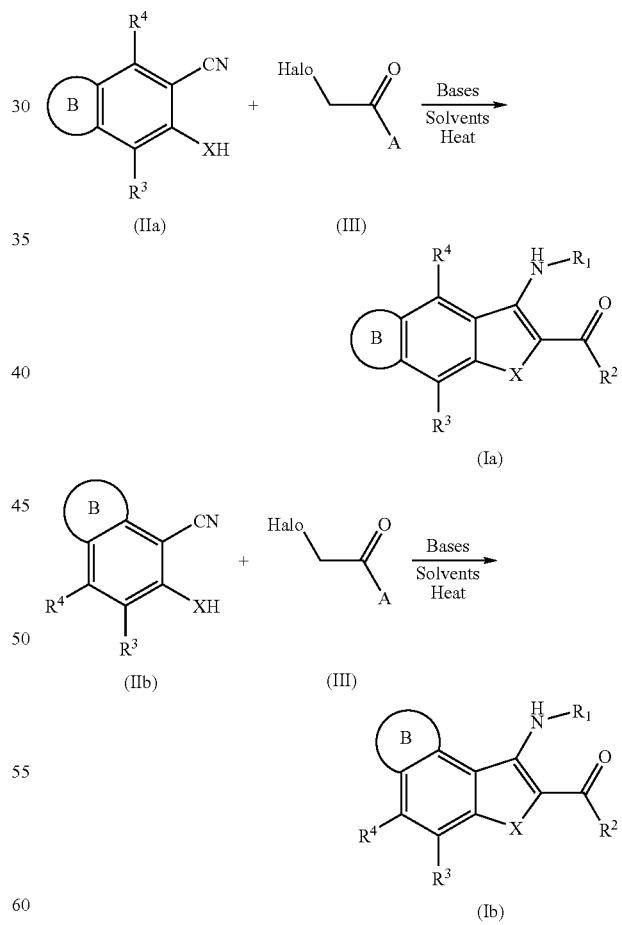

It is to be understood that sensitive or reactive substituents attached to intermediates or to compounds of Formula (Ia) and (Ib) may need to be protected and deprotected during the preparations described above. Protecting groups in general may be added and removed by conventional methods well known in the art (see, e.g., T. W. Greene and P. G. M. Wuts, *Protective Groups in Organic Synthesis*; Wiley: New York, (1999)).

Variations of the compounds of the invention can be readily prepared using the processes described above and referenced below, or by other standard chemical processes known in the art, by employing appropriate starting materials or intermediate compounds that are readily available and/or are described herein.

Generally, a desired salt of a compound of this invention can be prepared in situ during the final isolation and purification of a compound by means well known in the art. For example, a desired salt can be prepared by separately reacting the purified compound in its free base or free acid form with a suitable organic or inorganic acid, or suitable organic or inorganic base, respectively, and isolating the salt thus formed. In the case of basic compounds, for example, the free base is treated with anhydrous HCl in a suitable solvent such as THF, and the salt isolated as a hydrochloride salt. In the case of acidic compounds, the salts may be obtained, for example, by treatment of the free acid with anhydrous ammonia in a suitable solvent such as ether and subsequent isolation of the ammonium salt. These methods are conventional and would be readily apparent to one skilled in the art.

The compounds of this invention may be esterified by a variety of conventional procedures including reacting the appropriate anhydride, carboxylic acid or acid chloride with the alcohol group of a compound of this invention. The appropriate anhydride is reacted with the alcohol in the presence of a base to facilitate acylation such as 1,8-bis [dimethylamino]naphthalene or N,N-dimethylaminopyridine. Or, an appropriate carboxylic acid can be reacted with the alcohol in the presence of a dehydrating agent such as dicyclohexylcarbodiimide, 1-[3-dimethylaminopropyl]-3-ethylcarbodiimide or other water soluble dehydrating agents which are used to drive the reaction by the removal of water, and, optionally, an acylation catalyst. Esterification can also be effected using the appropriate carboxylic acid in the presence of trifluoroacetic anhydride and, optionally, pyridine, or in the presence of N,N-carbonyldiimidazole with pyridine. Reaction of an acid chloride with the alcohol can be carried out with an acylation catalyst such as 4-DMAP or pyridine.

One skilled in the art would readily know how to successfully carry out these as well as other known methods of esterification of alcohols.

The purification of isomers and the separation of isomeric mixtures of a compound of Formula (Ia) and (Ib) may be accomplished by standard techniques known in the art.

The following examples are provided to further illustrate the compounds of the invention and their preparation but should not be construed to be limiting in any way.

PREPARATIVE EXAMPLES OF THE INVENTION

Proton ($^1$H) nuclear magnetic resonance (NMR) spectra were measured with a General Electric GN-Omega 300 (300 MHz) spectrometer with either Me$_4$Si ($\delta$ 0.00) or residual protonated solvent (CHCl$_3$ $\delta$ 7.26; MeOH $\delta$ 3.30; DMSO $\delta$ 2.49) as standard. Carbon ($^{13}$C) NMR spectra were measured with a General Electric GN-Omega 300 (75 MHz) spectrometer with solvent (CDCl$_3$ $\delta$ 77.0; d$_3$-MeOD; $\delta$ 49.0; d$_6$-DMSO $\delta$ 39.5) as standard.

Chiral separations were performed using a commercially available Chiracel® AD HPLC column, eluting with a gradient of isopropanol in hexane (from 1% to 15%) with addition of 0.1% trifluoroacetic acid.

General Method I: Preparation of Intermediate 1-aryl-2-halo-ethanones (III)

The starting ketones of formula (III) are prepared by the methods exemplified below.

Example 1

Method I-1

Preparation
2-bromo-1-(2,4,6-trichlorophenyl)ethanone

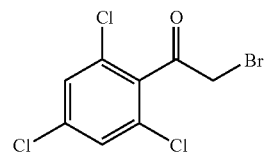

A mixture of 1,3,5-trichlorobenzene (10.0 g, 55.1 mmol), 2-bromoacetyl bromide (5.0 mL, 57.8 mmol, 1.05 eq), and aluminum chloride (7.7 g, 57.8 mmol, 1.05 eq) was heated neat at 80° C. under argon for 17 h until a black precipitate is formed. The reaction was cooled to room temperature, and the resultant black mass was dissolved in ethyl acetate (500 mL). Water (200 mL) was added slowly at 0° C. to quench the reaction, and the biphasic layers were separated. The organic layer was then washed with water (2×150 mL) and brine (1×150 mL), dried (MgSO$_4$), filtered, and evaporated in vacuo. Recrystallization from hexane gave 11.5 g (69.3%) of 2-bromo-1-(2,4,6-trichlorophenyl)ethanone as a fluffy white solid. $^1$H-NMR (DMSO-d$_6$) $\delta$ 7.86 (s, 2H), 4.78 (s, 2H); R$_f$=0.28, 2% ethyl acetate-hexane.

Example 2

Method I-2

Preparation of
2-bromo-1-(2,5-dichlorophenyl)ethanone

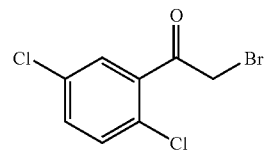

To 2,5-dichloroacetophenone (5.0 g, 26.45 mmol) in anhydrous tetrahydrofuran (53 mL) under argon was added phenyltrimethylammonium tribromide (9.94 g, 26.45 mmol, 1.0 eq) at 0° C. The reaction mixture was stirred at ambient temperature for 16 h, concentrated, and re-dissolved in ethyl acetate. The organic layer was washed with water (2×250 mL) and brine (1×150 mL), dried (MgSO$_4$), filtered, and evaporated in vacuo. Purification using MPLC chromatography (Biotage) gave 3.47 g (52.5%) of 2-bromo-1-(2,5-dichlorophenyl)ethanone as a clear oil. $^1$H-NMR (DMSO-d$_6$) $\delta$ 7.93 (dd, J=2.1 Hz, 0.9 Hz, 1H), 7.61 to 7.60 (m, 2H), 4.86 (s, 2H);

Many 2-bromo-1-arylethanones were prepared using this method. A few examples are listed below:

Example 3

Preparation of Starting Material
1-[2,4-bis(trifluoromethyl)phenyl]-2-bromoethanone

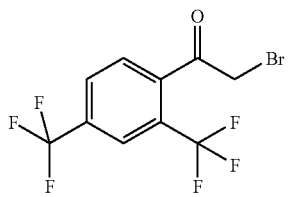

This compound was prepared from 1-[2,4-bis(trifluoromethyl)phenyl]ethanone (5.0 g, 19.52 mmol) in the manner described for 2-bromo-1-(2,5-dichlorophenyl)ethanone, affording 4.12 g (63%) of a white solid. $^1$H-NMR (DMSO-$d_6$) δ 8.28 to 8.16 (m, 3H), 4.98 (s, 2H);

Example 4

Preparation of intermediate
2-Bromo-1-(2-bromo-phenyl)-ethanone

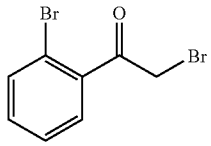

This compound was prepared from 1-(2-bromo-phenyl)-ethanone (2.5 g, 12.6 mmol) in the manner described for 2-bromo-1-(2,5-dichlorophenyl)ethanone (Method I-2), affording 1.98 g (57%) of 2-bromo-1-(2-bromo-phenyl)-ethanone as a clear oil. $^1$H-NMR (CD$_2$Cl$_2$) δ 8.13 (t, J=2 Hz, 1H), 7.92 (dm, J=8 Hz, 1H), 7.78 (dm, J=8 Hz, 1H), 7.42 (t, J=8 Hz, 1H), 4.49 (s, 2H); TLC Rf=0.38, 15%, ethyl acetate-hexanes.

Example 5

Preparation of
2-Bromo-1-(2-bromo-4-fluoro-phenyl)-ethanone

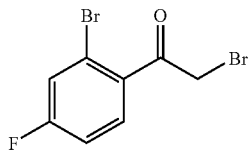

This compound was prepared from 1-(2-bromo-4-fluoro-phenyl)-ethanone (2.5 g, 11.52 mmol) in the manner described for 2-bromo-1-(2,5-dichlorophenyl)-ethanone (Method I-2), affording 2.14 g (63%) of 2-bromo-1-(2-bromo-4-fluoro-phenyl)-ethanone as a clear oil. $^1$H-NMR (CD$_2$Cl$_2$) δ 7.57 (dd, J=9, 6 Hz, 1H), 7.44 (dd, J=8, 2 Hz, 1H), 7.21 ((m, 7.21–7.14, 1H), 4.51 (s, 2H); TLC Rf=0.38, 15% ethyl acetate-hexanes.

Example 6

Method I-3

Preparation of
2-chloro-1-(4-methyl-3-pyridinyl)ethanone

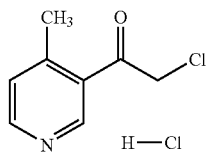

Step 1: Preparation of 1-(4-methyl-3-pyridinyl)ethanone

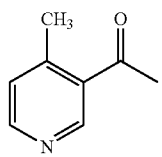

A solution of 3-acetylpyridine (100 g, 0.82 mmol), dimethyl sulfide (400 mL, 5.4 mmol) and copper (I) iodide (7.94 g, 0.041 mmol) in anhydrous THF (2 L) was stirred at room temperature under an argon atmosphere. Phenyl chloroformate (0.4 mL, 0.82 mmol) was then added, producing a dark brown precipitate. After 30 min, the mixture was cooled below –21° C. and methyl magnesium bromide (1.4 M in 3:1 toluene-THF, 586 mL, 0.82 mmol) was added over 50 min, keeping the reaction temperature below –15° C. The color lightened as the mixture became a solution; a lime green precipitate formed near the end of the addition, but redissolved upon completion. The mixture was stirred and allowed to warm slowly; after 2 h it had warmed to 8.8° C. Saturated aqueous ammonium chloride solution (500 mL) was added; after stirring 10 min, the mixture was poured into a separatory funnel with water (500 mL). The organic phase was separated, washed with brine (500 mL), dried (Na$_2$SO$_4$), filtered and then concentrated in vacuo. The residue was purified by silica gel chromatography using a hexane-EtOAc gradient to afford 134.3 g (63.7%) of the intermediate dihydropyridine.

A solution of the intermediate dihydropyridine (0.52 mmol) in dichloromethane (100 mL) was added to a stirred suspension of sulfur (16.67 g, 0.52 mmol) in decalin and slowly heated to reflux under an argon sweep. After refluxing 1 h, the mixture was allowed to cool to room temperature, then filtered through a pad of silica gel. After eluting the decalin with hexane, elution with a hexane-diethyl ether gradient afforded 49.4 g (70.3%) the desired 1-(4-methyl-3-pyridinyl)ethanone as a reddish-brown oil: TLC Rf 0.19 (diethyl ether); TLC Rf 0.14 (1:1 hexane-EtOAc); $^1$H NMR (CD$_2$Cl$_2$) δ 8.9 (s, 1H), 8.5(d, 1H), 7.2 (dd, 1H), 2.6 (s, 3H), 2.51 (s, 3H); MS GC-MS (MH$^+$135).

Step 2: Preparation of 2-chloro-1-(4-methyl-3-pyridinyl)ethanone Hydrochloride

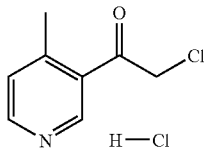

In a 500 mL round bottom flask was placed 1-(4-methyl-3-pyridinyl)ethanone (10.0 g, 74.1 mmol) in 90 mL of Et$_2$O. To this solution was added 88.9 mL of 1M HCl/Et$_2$O (1.2 eq, 88.9 mmol) with stirring and the solution allowed to stir for 1 h at room temperature, at which point, the precipitate was filtered and washed with Et$_2$O. The solid was then dried in vacuo at about 60° C. This HCl salt (12. g, 70.0 mmol) was then dissolved in 70.0 mL of 1M HCl/acetic acid where 9.34 g (1 eq, 70.0 mmol) of N-chlorosuccinimide (NCS) was added and the reaction allowed to stir under Argon at room temperature overnight. At this point, 300 mL of Et$_2$O was added resulting in an off-white precipitate. This was allowed to stir for 1 h at which point the solid was filtered and rinsed with Et$_2$O to provide 12.0 g (83%) of the desired 2-chloro-1-(4-methyl-3-pyridinyl)ethanone hydrochloride. $^1$H-NMR (DMSO-d$_6$) δ 2.51 (s, 3H), 5.15 (s, 2H), 7.68 (d, 1H), 8.68 (d, 1H), 9.06 (s, 1H); MS GC-MS [MH]$^+$169.

Example 7

Method I-4

Preparation of 2-chloro-1-[4-(trifluoromethyl)-3-pyridinyl]ethanone Hydrochloride

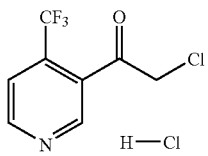

Step 1: In a 250 mL round bottom flask was placed 3.0 g of 4-trifluoronicotinic acid (15.7 mmol, 1 eq) in 100 mL of THF. To this was added 5.3 mL (3.8 g, 37.7 mmol, 2.4 eq) of triethylamine and 9.8 g (18.8 mmol, 1.2 eq) of PyBOP. This was allowed to stir for 10 min at room temperature where 2.7 g of Meldrum's acid (18.8 mmol, 1.2 eq) was added and the reaction allowed stirring at room temperature overnight. (18 h).

At this point, 30 mL of 1M HCl (aq) was added and the reaction turned immediately from orange to purple. This was then heated at for 18 h gradually turning from purple to yellow.

The reaction was then basified with saturated NaHCO$_3$ and extracted with EtOAc (3×200 mL). The combined organic layers were dried, filtered, and evaporated. The residue was purified via BIOTAGE (35% EtOAc/Hex) to provide methyl 4-trifluoromethylnicotinate 1.84 g (62%) of the desired product as a colorless oil. TLC R$_f$=0.57 (50% EtOAc:Hex).

Step 2: In a 100 mL flask was placed 1.84 g (9.7 mmol, 1 eq) of methyl 4-trifluoromethylnicotinate in 25 mL of 1 M HCl in CH$_3$COOH. To this was then added 1.3 g of NCS (9.7 mmol, 1 eq) and the reaction allowed stirring overnight (18 h).

The mixture was then transferred to a 500 mL Erlenmeyer flask and to this was added 300 mL of 2 M HCl in Et$_2$O with stirring. This resulted in a white precipitate which was then filtered to provide 1.2 g (49%) of the desired 2-chloro-1-[4-(trifluoromethyl)-3-pyridinyl]ethanone hydrochloride as a white solid. $^1$H-NMR (DMSO-d$_6$) δ 9.21 (s, 1H), 9.02 (d, 1H), 7.94 (d, 1H), 5.19 (s, 2H).

Example 8

Method I-5

Preparation of 2-bromo-1-(3-ethyl-pyrazin-2-yl)-ethanone

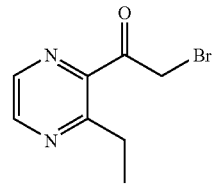

To a solution of 2-acetyl-3-ethylpyrazine (1.0 g, 6.66 mmol) in chloroform (15 mL) was added Br2 (0.38 mL, 7.32 mmol, 1.1 eq) dropwise at 0° C. The reaction mixture was stirred at 40° C. for 4 h. The reddish solution turned to dark brown. The reaction mixture was concentrated in vacuo and used in the step 2 without further purification. MS LC-MS (MH$^+$=231).

Example 9

Method I-6

Preparation of 2-chloro-1-(2,5-dichloro-3-pyridinyl)-ethanone

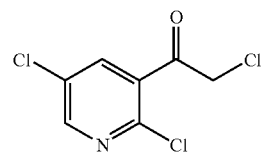

Step 1: In a 100 mL round bottom flask was placed magnesium chloride (316.7 mg, 3.33 mmol, 0.7 eq in 20 mL of toluene. To this suspension was added dimethyl malonate (653 mg, 4.94 mmol, 1.04 eq) and triethylamine (1.63 mL, 11.69 mmol, 2.46 eq). The resulted mixture was stirred for 1 h at room temperature then a solution of 2,5-dichloropyridine-3-carbonyl chloride (1.0 g, 4.75 mmol, 1.0 eq) in 10 mL of toluene was added slowly and the reaction was allowed stirring at room temperature overnight (18 h).

At this point, 30 mL of water and 1.0 mL of concentrated HCl was added and extracted with ethyl ether (3×50 mL). The combined organic layers were washed with brine, dried (MgSO4), filtered, and evaporated to provide 2.0 g of reddish crude oil. This oil was dissolved in 4.4 mL of DMSO and 0.16 mL of water and was allowed to heat at 135° C. overnight (18 h).

The reaction solution was cooled down and 30 mL of water was added and extracted with ethyl ether (3×50 mL). The combined organic layers were washed with brine, dried (MgSO4), filtered and evaporated to provide 1-(2,5-dichloro-3-pyridinyl)ethanone, 2.0 g of brownish oil which will be used in next step reaction without purification.

Step 2: In a 50 mL flask was placed 1-(2,5-dichloro-3-pyridinyl)ethanone (505 mg, 2.66 mmol, 1 eq) in 2.7 mL of 1 M HCl in CH3COOH. To this was then added NCS (355.2 mg, 2.66 mmol, 1 eq) and the reaction allowed stirring overnight. (18 h).

The mixture was basified with solution of 40% NaOH to pH about 8 at 0° C. then extracted with EtOAc (3×50 mL). The combined organic layers were washed with brine, dried (MgSO4), filtered and evaporated to provide a crude residue, which was chromatographed with Hexane/EtOAc=3/1 to provide 339.3 mg of desired 2-chloro-1-(2,5-dichloro-3-pyridinyl)ethanone as a yellow semi-solid (56.8%). 1H-NMR (DMSO-d6) δ 8.66 (s, 1H), 8.46 (s, 1H), 5.11 (s, 2H).

Example 10

Method I-7

Preparation of 1-Benzo[1,3]dioxol-4-yl-2-bromo-ethanone

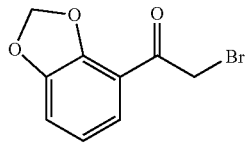

Step 1: Preparation of Starting Material 1-Benzo[1,3]dioxol-4-yl-ethanone

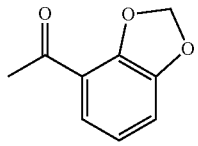

To a solution of MeMgBr in THF (1 M, 50 mL, 50 mmol, 1.5 eq) was diluted with 50 mL THF and cooled to −10° C. A solution of benzo[1,3]dioxole-4-carbaldehyde (5.0 g, 33.3 mmol) in 50 mL THF was slowly added, and the reaction left to stir for 1 h. The reaction mixture was then quenched by poured into 500 mL of ice cold sat. ammonium chloride and the mixture was extracted with ether. The organic layers were dried over sodium sulfate and filtered through a plug of silica gel before concentrating in vacuo, providing 4.9 g of a white solid. A mixture of this solid (2.0 g, 12.0 mmol) and MnO2 (10.5 g, 120.4 mmol, 10.0 eq) in 75 mL diethyl ether was stirred vigorously for 48 h. The reaction mixture was then filtered first through a plug of silica gel, then through a 0.46 μm frit before concentrating in vacuo to provide 2.1 g of an off-white solid. Purification by MPLC (Biotage) using a hexane-ethyl acetate gradient provided 1.47 g (74%) of 1-benzo[1,3]dioxol-4-yl-ethanone as an off-white solid.

1H-NMR (CDCl3) δ 7.35 (d, J=8 Hz, 1H), 6.97 (dm, J=8 Hz, 1H), 6.87 (dd, J=8 Hz, 1H), 6.08 (s, 2H), 2.59 (s, 3H); TLC Rf=0.18, 25% ethyl acetate-hexanes.

Step 2: Preparation of Intermediate 1-Benzo[1,3]dioxol-4-yl-2-bromo-ethanone

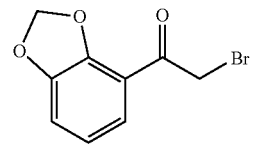

This compound was prepared from 1-benzo[1,3]dioxol-4-yl-ethanone (2.15 g, 13.1 mmol) in the manner described for 2-bromo-1-(2,5-dichlorophenyl)ethanone (Method I-2), affording 1.54 g (48%) of 1-benzo[1,3]dioxol-4-yl-2-bromo-ethanone as an off-white solid.

1H-NMR (CD2Cl2) δ 7.41 (dd, J=8, 1 Hz, 1H), 7.05 (dd, J=8, 1 Hz, 1H), 6.94 (dd, J=8, 8 Hz, 1H), 6.13 (s, 2H), 4.55 (s, 2H). TLC Rf=0.28, 15%, ethyl acetate-hexanes.

General Method II: Preparation of substituted 2-cyanophenols (IIa and IIb)

Example 11

Method II-1

Preparation of of 5,6,7,8-tetrahydro-3-cyano-2-naphthol and of 5,6,7,8-tetrahydro-1-cyano-2-naphthol as a mixture

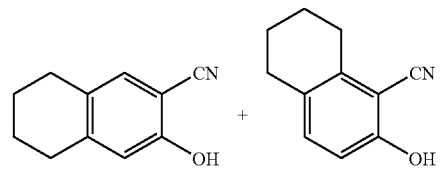

To a stirred mixture of 5,6,7,8-tetrahydro-2-naphthol (10.0 g, 67.47 mmol) in anhydrous dichloroethane (45 mL) was added, at 0° C., 1.0 M boron trichloride in dichloromethane (74.2 mL, 74.2 mmol, 1.1 eq,) followed by methyl thiocyanate (5.1 mL, 74.2 mmol, 1.1 eq) and aluminum chloride (9.0 g, 67.47 mmol, 1.0 eq). The reaction mixture was stirred at room temperature for 2 days and then cooled to 0° C. To the dark brown reaction mixture was added 50% aqueous sodium hydroxide solution (150 mL) until pH reached above 12. The resulting yellow biphasic layers were stirred at reflux for 1 h and then cooled to room temperature. The biphasic layers were separated, and the aqueous layer was adjusted to pH 1 with 50% aqueous hydrogen chloride solution (~200 mL) at 0° C. The acidified aqueous mixture was extracted with ethyl acetate (3×400 mL), and the combined organic layers were dried (MgSO4), filtered, and concentrated under reduced pressure. The crude cyanophenols were purified through a pad of silica eluted with 25% ethyl acetate-hexane to give a 2:1 mixture of 5,6,7,8-tetrahydro-3-cyano-2-naphthol and of 5,6,7,8-tetrahydro-1-cyano-2-naphthol, respectively, as a white solid (6.64 g, 56.8%). For 5,6,7,8-tetrahydro-3-cyano-2-naphthol:

1H-NMR (DMSO-d6) δ 10.55 (s, 1H), 7.23 (s, 1H), 6.65 (s, 1H), 2.73 to 2.49 (m, 8H); MS GC-MS (MH+=174).

For 5,6,7,8-tetrahydro-1-cyano-2-naphthol:

$^1$H-NMR (DMSO-d$_6$) δ 10.63 (s, 1H), 7.12 (d, J=8.4 Hz, 1H), 6.72 (d, J=8.4 Hz, 1H), 1.75 to 1.58 (m, 8H); MS GC-MS (MH$^+$=174).

The mixture prepared according to the above-described procedure gave a range of 2:1 to 1:1 ratio of the two regioisomers in favor of 5,6,7,8-tetrahydro-3-cyano-2-naphthol. They were used as such to prepare the benzofuran derivatives that can be separated by convention chromatographic purification means.

An improved procedure as described in method II-2, however, gave 5,6,7,8-tetrahydro-3-cyano-2-naphthol exclusively.

Example 12

Method II-2

Preparation of 5,6,7,8-tetrahydro-3-cyano-2-naphthol

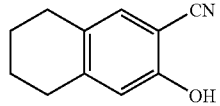

In a 1000 mL round-bottom flask was placed 5,6,7,8-tetrahydro-2-naphthalenol (13.4 g, 90.9 mmol, 1 eq) in 60 mL of dry dichloroethane under argon. This was cooled to 0° C. where boron trichloride (100 mL, 1M in CH$_2$Cl$_2$, 100 mmol, 1.1 eq) was added via cannula over 10 min. At this point, methyl thiocyanate (7.3 g, 100 mmol, 1.1 eq) was added followed by aluminum trichloride (12.1 g, 90.9 mmol, 1 eq). The reaction was allowed to warm up to rt slowly overnight (18 h) and then allowed to stir further 72 h.

At this point, 200 mL of 50% w/w NaOH was added, together with 150 mL of water, resulting in a thick paste. The flask was equipped with a large volume condenser and then heated at 100° C. for 3 h. The mixture was transferred to an Erlenmeyer flask and acidified to pH~1 with conc. HCl. This solution was then extracted in portions with EtOAc and the combined organic layers were dried over NaSO$_4$, filtered and evaporated. The residue was suspended in CH$_2$Cl$_2$ and filtered. The filtrate was concentrated and the suspension procedure was repeated until no further solid precipitated. The combined solids were found to be nearly pure product with minor contaminants. The contaminants were removed with silica gel plug filtration to provide 10.7 g (68%) of the desired product as an off-white solid.

$^1$H-NMR (CD$_3$CN) δ 7.77 (s, 1H, OH), 7.25 (s, 1H), 6.70 (s, 1H), 2.76 (m, 2H), 2.69 (m, 2H), 1.77 (m, 4H). LC/MS RT=2.86; [M+H+MeCN]$^+$=215.4.

Example 13

Preparation of 6-hydroxy-indan-5-carbonitrile

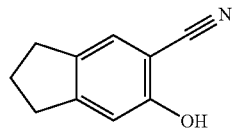

To a stirred solution of Indan-5-ol (5.0 g, 32.3 mmol) in anhydrous dichloroethane (21.5 mL) was added, at 0° C., 1.0 M boron trichloride in dichloromethane (41.0 mL, 41.0 mmol, 1.2 eq), followed by methyl thiocyanate (2.43 mL, 35.5 mmol, 1.1 eq) and aluminum chloride (4.30 g, 2.3 mmol, 1.0 eq). The reaction mixture was stirred at room temperature for 2 d and then cooled to 0° C. To the dark brown reaction mixture was added 50% aqueous sodium hydroxide solution (100 mL) until pH=11. The resulting yellow biphasic layers were stirred at reflux for 3 h. The biphasic layers were separated, and the aqueous layer was adjusted to pH=1 with 50% aqueous hydrogen chloride solution at 0° C. The acidified aqueous mixture was extracted with ethyl acetate, and the combined organic layers were dried over sodium sulfate and concentrated at reduced pressure. Crystallization from ether-hexane afforded the cyanophenol as a white solid (3.02 g, 50.9%). $^1$H-NMR (DMSO-d$_6$) δ 10.67 (s, 1H), 7.36 (s, 1H), 6.84 (s, 1H), 2.81 (t, J=7.5 Hz, 2H), 2.73 (t, J=7.5 Hz, 2H), 1.99 to 1.93 (m, 2H); R$_f$=0.23, 25% ethyl acetate-hexane.

This one-step cyanation was widely used in this invention to prepare the substituted 2-cyanophenols needed for many examples. In case the desired substituted phenol is not commercially available, it was synthesized by conventional methods. Some examples are shown below (but not limited to these examples):

Example 14

Preparation of 8-methyl-5,6,7,8-tetraydro-napthalen-2-ol

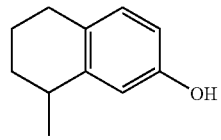

Step 1: Preparation of 7-methoxy-1-methyl-1,2,3,4-tetrahdro-napthalen-1-ol

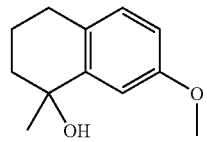

To a round-bottomed flask which had been purged of air and back-filled with argon was added methylmagnesium bromide (16.9 g, 142 mmol). This was cooled to −78° C. To this was added anhydrous THF (125 mL) via canula. Once this had cooled back to −78° C., a solution of 7-methoxy-1-tetralone (10 g, 57 mmol) in anhydrous THF (100 mL) was added slowly by canula. After this addition was complete, the cold bath was removed and the flask was allowed to return to rt. This solution was then poured into saturated ammonium carbonate (500 mL) which had been pre-chilled to 0° C. Ethyl acetate (200 mL) was added and the mixture was poured into a separatory funnel. The organic layer was washed once with water (2×200 mL) and once with a mixture of water and brine. The organic layer was collected and dried overnight using magnesium sulfate. This solution was filtered through a pad of celite and concentrated in vacuo to yield 10.75 g (93.6%) of 7-methoxy-1-methyl-1,2,3,4-tetrahdro-napthalen-1-ol. $^1$HNMR (DMSO-$d_6$) δ 7.04 (d, J=2.3 Hz, 1H), 6.91 (d, J=8.1 Hz, 1H), 6.67 (dd, J=8.0, 2.3 Hz, 1H), 4.83 (s, 1H), 3.68 (s, 3H), 2.59 (m, 2H), 1.82 (m, 1H), 1.75 (m, 2H), 1.65 (m, 1H), 1.34 (s, 3H), GC/MS RT=10.2 min, ($M^+$=192), TLC Rf=0.55 (30% ethyl acetate-hexanes).

Step 2: Preparation of 7-methoxy-1-methyl-1,2,3,4-tetrahydro-napthalene

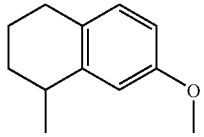

To a round-bottomed flask which had been purged of air and back-filled with argon was added palladium (II) hydroxide (2.1 g, 15 mmol). Ethanol (220 mL) was added via canula, and a solution of 7-methoxy-1-methyl-1,2,3,4-tetrahdro-napthalen-1-ol in ethanol (220 mL) was then added in the same manner. While stirring vigorously, the flask was purged of argon under vacuum and backfilled with hydrogen gas; this process was repeated 3 times. The solution was allowed to stir under 1 atm hydrogen for 6 h at rt. The solution was then filtered through a pad of celite once followed by a 0.45 μm syringe filter. The filtrate was concentrated in vacuo to yield 8.67 g (91.3%) of 7-methoxy-1-methyl-1,2,3,4-tetrahydro-napthalene as a greenish oil. $^1$HNMR (DMSO-$d_6$) δ 6.83 (d, J=8.8 Hz, 1H), 6.68 (d, J=2.50 Hz, 1H), 6.56 (dd, J=8.5, 2.8 Hz, 1H), 3.65 (s, 3H), 2.76 (m, 1H), 2.57 (m, 2H), 1.86–1.52 (m, 3H), 1.39 (m, 1H), 1.18 (d, J=7.3, 3H), GC/MS RT=9.57 min ($M^+$=176), TLC Rf=0.9 (30% ethyl acetate-hexane).

Step 3: Preparation of 8-methyl-5,6,7,8-tetraydro-napthalen-2-ol

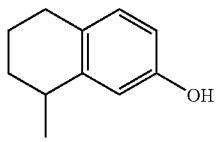

To a solution of 7-methoxy-1-methyl-1,2,3,4-tetrahydro-napthalene (230 mg, 1.30 mmol) in dichloromethane (2.5 mL) at 0° C. was added aluminum chloride (870 mg, 6.52 mmol). This was allowed to stir for 5 min. Ethane thiol (405 mg, 6.52 mmol) was added and the solution was allowed to stir 1 h at 0° C. followed by 2 h at rt. The reaction was then cooled back down to 0° C. and quenched with water (10 mL). The product was then extracted using methylene chloride (3×10 mL). The organic was dried with sodium sulfate and concentrated in vacuo to yield 208 mg (98.1%) of 8-methyl-5,6,7,8-tetraydro-napthalen-2-ol. $^1$HNMR (CD$_2$Cl$_2$) δ 6.91 (d, J=8.5 Hz, 1H), 6.68 (d, J=1 Hz, 1H), 6.61 (dd, J=8.5, 2.8, 1H) 4.64 (s, 1H), 2.84 (m, 1H), 2.66 (m, 2H), 1.95–1.76 (m, 2H), 1.75–1.60 (m, 1H), 1.56–1.42 (m, 1H), 1.25 (d, J=5.1 Hz, 3H), GC-MS RT=11.20 min, ($M^+$=162), TLC Rf=0.75 (10% ethyl acetate-hexane).

Example 15

Method II-3

Preparation of starting material 7-Hydroxy-chroman-6-carbonitrile

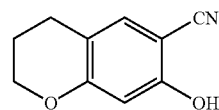

Step 1: Preparation of 4-(3-Hydroxy-propyl)-benzene-1,3-diol

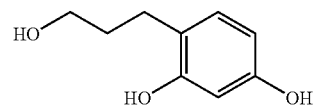

To a stirred solution of 7-hydroxycoumarin (7.0 g, 43.2 mmol) in anhydrous THF (200 mL) at rt under argon was added Lithium borohydride (2M, 65.8 mL, 129.6 mmol, 3.0 eq) solution in THF dropwise. Anhydrous methanol (1.0 mL) was added as catalyst to the reaction mixture. The mixture was heated at 65° C. for 17 h. The reaction mixture was then cooled to ambient temperature. Saturated ammonium chloride solution (40 mL) was added dropwise to the solution, followed by 1N HCl solution (40 mL). The mixture was extracted with ethyl acetate (2×100 mL). The combined organic extracts were dried (Na$_2$SO$_4$), filtered, and evaporated in vacuo. The residue was purified on silica gel (flash column chromatography) eluting with 30% ethyl acetate-hexane to provide the desired product as white solid (3.05 g, 42%). $^1$H-NMR (CD$_3$CN) δ 6.91 (d, 1H), 6.29 (s, 1H), 6.28 (d, 1H), 3.51 (t, 2H), 2.56 (t, 2H), 1.73 (m, 2H). MS GC-MS ($M^+$=168).

Step 2: Preparation of Chroman-7-ol

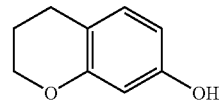

To a stirred solution of 4-(3-Hydroxy-propyl)-benzene-1,3-diol (3.05 g, 18.1 mmol, from Step 1) in anhydrous THF (50 mL) were added Ph$_3$P (7.13 g, 27.2 mmol, 1.5 eq) and ADDP (6.86 g, 27.2 mmol, 1.5 eq) under argon. The mixture was stirred at rt for 17 h. The white solid was filtered off and the solvent was removed from the filtrate. The residue was purified on silica gel (flash column chromatography) eluting with 5% ethyl acetate-hexane followed by 20% ethyl acetate-hexane to provide the desired product as white solid (1.80 g, 60.5%). $^1$H-NMR (CD$_3$CN) δ 6.87 (d, 1H), 6.70 (broad, s, 1H, OH), 6.31 (dd, J=2.4, 8.2 Hz, 1H), 6.20 (d, 1H), 4.12 (t, 2H), 2.69 (t, 2H), 1.95 (m, 2H).

Step 3: Preparation of starting material 7-Hydroxy-chroman-6-carbonitrile

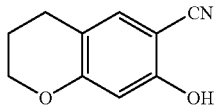

In a 250 mL round-bottom flask was placed Chroman-7-ol (1.8 g, 12.0 mmol, from Step 3-1-2) in dry dichloroethane (30 mL) under argon. The solution was cooled to 0° C. where boron trichloride (13.2 mL, 1M in $CH_2Cl_2$, 13.2 mmol, 1.1 eq) was added dropwise. At this point, methyl thiocyanate (0.97 g, 13.2 mmol, 1.1 eq) was added followed by aluminum trichloride (1.6 g, 12.0 mmol, 1 eq). The reaction was allowed to warm up to rt and stirred for 17 h. The reaction mixture was cooled down to 0° C. and 10 mL of 50% w/w NaOH was added to adjust the solution to PH~14, followed by 40 mL of water. The solution was then refluxed at 65° C. for 2 h. The solution was allowed to cool to ambient temperature. The aqueous layer was washed with dichloromethane (20 mL). The aqueous solution was then transferred to an Erlenmeyer flask and acidified to pH~1 with conc. HCl (aq.). This solution was extracted with EtOAc (3×20 mL) and the combined organic layers were dried over $Na_2SO_4$, filtered and evaporated. The residue was suspended in cold $CH_2Cl_2$ and filtered. The filtrate was concentrated and the suspension procedure was repeated until no further solid precipitated. The combined solids were found to be nearly pure product with minor contaminants. The desired product was white solid (1.20 g, 54.3%). $^1$H-NMR ($CD_3CN$) δ 7.87 (s, 1H, OH), 7.25 (s, 1H), 6.35 (s, 1H), 4.21 (t, 2H), 2.70 (t, 2H), 1.98 m, 2H).

Example 16

Method II-4

Preparation of 7-Hydroxy-2,2-dimethyl-chroman-6-carbonitrile

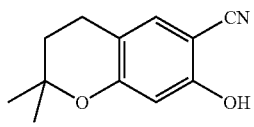

Step 1: Preparation of 7-Methoxy-2,2-dimethyl-chroman

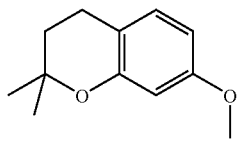

A solution of precocene I (5.0 g, 26.3 mmol) in EtOH (200 mL) was hydrogenated by using 10% Pd/C (0.5 g) as catalyst. The catalyst was filtered of and EtOH was removed under reduced pressure. The crude material was then washed with dichloromethane (2×50 mL) to afford the desired product as white solid (4.55 g, 90%). $^1$H-NMR ($CD_3CN$) δ 6.97 (d, J=8.0 Hz, 1H), 6.42 (d, J=8.0 Hz, 1H), 6.27 (s, 1H), 3.74 (s, 3 H), 2.72 (t, 2 H), 1.80 (t, 2 H), 1.32 (s, 6 H); MS LC-MS ($MH^+$=193).

Step 2: Preparation of 2,2-Dimethyl-chroman-7-ol

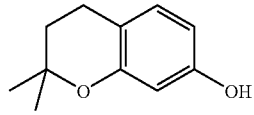

To a stirred solution of 7-Methoxy-2,2-dimethyl-chroman (4.55 g, 23.7 mmol, from step 1) in anhydrous dichloromethane (50 mL) was added 1M $BBr_3$ (72.86 mL, 47.4 mmol, 2.0 eq) via cannula over 10 min. The resulting dark brown solution was stirred at rt for 17 h. Saturated solution of $NaHCO_3$ (50 mL) was added and extracted with $CH_2Cl_2$ (3×50 mL. The combined organic layers were dried over $Na_2SO_4$, filtered and evaporated. The residue was purified on silica gel (flash column chromatography) eluting with 5% ethyl acetate-hexane followed by 20% ethyl acetate-hexane to provide the desired product as white solid (1.76 g, 42%). $^1$H-NMR ($CD_3CN$) δ 6.89 (d, J=8.5 Hz, 1H), 6.68 (broad, s, 1H, OH), 6.31 (dd, J=2.4, 8.5 Hz, 1H), 6.15 (d, J=2.4 Hz, 1H), 2.69 (t, 2H), 1.79 (t, 2H), 1.31 (s, 6H). MS LC-MS ($MH^+$=179).

Step 3: Preparation of 7-Hydroxy-2,2-dimethyl-chroman-6-carbonitrile

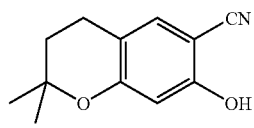

In a 250 mL round-bottom flask was placed 2,2-dimethyl-Chroman-7-ol (1.76 g, 9.87 mmol, from Step 4-1-2) in 30 mL of dry dichloroethane under argon. The solution was cooled to 0° C. where boron trichloride (10.8 mL, 1M in $CH_2Cl_2$, 10.8 mmol, 1.1 eq) was added dropwise. At this point, methyl thiocyanate (0.80 g, 10.8 mmol, 1.1 eq) was added followed by aluminum trichloride (1.32 g, 9.87 mmol, 1 eq). The reaction was allowed to warm up to rt and stirred for 17 h. The reaction mixture was cooled down to 0° C. and 10 mL of 50% w/w NaOH was added to adjust the solution to PH—14, followed by 40 mL of water. The solution was then refluxed at 65° C. for 2 h. The solution was allowed to cool to ambient temperature. The aqueous layer was washed with dichloromethane (20 mL). The aqueous solution was transferred to an Erlenmeyer flask and acidified to pH~1 with conc. HCl. This solution was then extracted with EtOAc (3×20 mL) and the combined organic layers were dried over $Na_2SO_4$, filtered and evaporated. The residue was purified on silica gel (flash column chromatography) eluting with 5% ethyl acetate-hexane followed by 20% ethyl acetate-hexane to provide the desired product as white solid. The desired product was white solid (0.33 g, 16.5%). $^1$H-NMR ($CD_3CN$) δ 7.93 (broad s, 1H, OH), 7.26 (s, 1H), 6.28 (s, 1H), 2.69 (t, 2H), 1.80 (t, 2H), 1.32 (s, 6H).

Example 17

Method II-5

Preparation of 4-Chloro-3-hydroxy-5,6,7,8-tetrahydro-naphthalene-2-carbonitrile and 1-Chloro-3-hydroxy-5,6,7,8-tetrahydro-naphthalene-2-carbonitrile

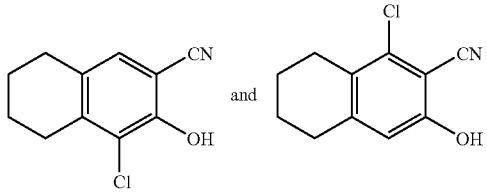

In a 100 mL round-bottom flask was placed 5,6,7,8-tetrahydro-3-cyano-2-naphthol (1.0 g, 5.77 mmol, 1 eq, from Method II-2) in 20 mL of dry acetonitrile under argon. Sulfuryl chloride (6.09 mL, 28.85 mmol, 5.0 eq) was added dropwise. The reaction was stirred at rt for 18 h. The reaction mixture was concentrated and purified on silica gel (flash column chromatography) eluting with 20% ethyl acetate-hexane. A 1:1 diastereomeric mixture of 4-Chloro-3-hydroxy-5,6,7,8-tetrahydro-naphthalene-2-carbonitrile and 1-Chloro-3-hydroxy-5,6,7,8-tetrahydro-naphthalene-2-carbonitrile was obtained as a yellow liquid (887 mg, 66.6%, isomer ratio: 1:1). $^1$H-NMR (CD$_3$CN) δ 7.81 (s, 1H), 3.24 (m, 1H), 2.66 (m, 1H), 2.33 (m, 1H), 2.07(m, 2H), 1.88 (m, 2H), 1.43 (m, 1H). GC-MS (M$^+$=207).

Example 18

Method II-6

Preparation of 3-hydroxy-8-oxo-5,6,7,8-tetrahydronaphthalene-2-carbonitrile

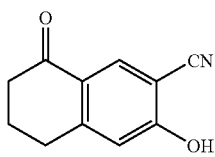

5,6,7,8-tetrahydro-2-naphthalenol prepared in method II-2 (1.5 g, 8.7 mmol) was dissolved in 1,4-dioxane (8 mL) in a 100 mL round bottom flask. To this was added water (2 mL), and 2,3-dichloro-5,6-dicyano-1,4-benzoquinone (DDQ) (4.1 g, 18.2 mmol, 2.1 eq) in anhydrous 1,4-dioxane (16 mL) dropwise. The reaction mixture turned to black immediately after addition and resulting mixture was stirred at room temperature for 3 h. The mixture was filtered and the filtrate was evaporated in vacuo. The residue was participated between EtOAc and saturated aqueous sodium bicarbonate. The aqueous layer was acidified to about pH 3 and was extracted with EtOAc three times. The organic layers were combined and evaporated in vacuo. Purification using MPLC chromatography (Biotage) gave 0.64 g (40%) of 3-hydroxy-8-oxo-5,6,7,8-tetrahydronaphthalene-2-carbonitrile as a light brown solid.

1H-NMR (CH$_3$OH-d4) δ 8.11 (s, 1H), 6.83 (s, 1H), 2.97 (t, J=6.0 Hz, 2H), 2.60 (t, J=6.7 Hz, 2H), 2.12 (m, 2H); Rf=0.39 (100% EtOAc).

Example 19

Method II-7

Preparation of 2-hydroxy-5-hydroxymethoxy-benzonitrile

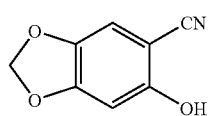

Step 1: Preparation of Starting Material 4-ethoxy-2-hydroxy-5-methyl-benzaldehyde

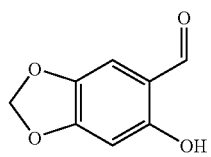

A mixture of sesamol (5.0 g, 36.2 mmol), paraformaldehyde (7.3 g, 244.4 mmol, 6.75 eq), magnesium chloride (5.2 g, 54.3 mmol, 1.5 eq), and triethylamine (13.7 g, 135.8 mmol, 3.75 eq) was heated in 180 mL of acetonitrile at reflux for 1 h. The reaction was cooled to room temperature, then poured into 500 mL 1 N HCl and the mixture extracted with 3 portions of ether (3×250 mL). The organic layers were combined, washed with a saturated sodium chloride solution and then dried with sodium sulfate. Evaporation in vacuo gave a yellow solid which after recrystallization provided 4.3 g (71.5%) of 4-ethoxy-2-hydroxy-5-methyl-benzaldehyde as a bright yellow solid. $^1$H-NMR (CD$_2$Cl$_2$) δ 11.79 (s, 1H), 9.62 (s, 1H), 6.89 (s, 1H), 6.44 (s, 1H), 6.01 (s, 2H); MS LC-MS (MH$^+$=167.1); LC-MS R$_f$=1.93.

Step 2: Preparation of 2-hydroxy-5-hydroxymethoxy-benzonitrile

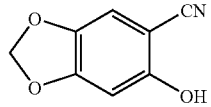

A mixture of 4-ethoxy-2-hydroxy-5-methyl-benzaldehyde (2.4 g, 14.6 mmol), sodium acetate (2.40 g, 29.25 mmol, 2.0 eq), acetic acid (3.4 g, 57.1 mmol, 3.9 eq), and nitroethane (2.2 g, 29.25 mmol, 2.0 eq) was heated in a sealed tube at 115° C. for 18 h. The black reaction mixture was poured into 40 g of ice and extracted 5 times with diethyl ether (100 mL). The organic layers were combined, washed 3 times with sat. sodium bicarbonate solution (25 mL), one time with brine, dried with sodium sulfate an finally concentrated in vacuo to give a black colored oil. Purification by MPLC chromatography (Biotage) using a hexane-ethyl acetate gradient gave 1.45 g (61%) of 2-hydroxy-5-hydroxymethoxy-benzonitrile as an orange solid. $^1$H-NMR (DMSO-d$_6$) δ 10.69 (s, 1H), 7.04 (s, 1H), 6.51 (1, 2H), 6.01 (s, 2H); TLC Rf=0.73, 50% ethyl acetate-hexanes.

Example 20

Method III Preparation of Benzofuran

Method III-1

Preparation of 3-amino-5,6,7,8-tetrahydronaphtho[2,3-b]furan-2-yl)(2,4-dichlorophenyl) methanone

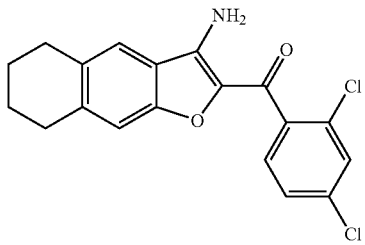

To a stirred solution of 5,6,7,8-tetrahydro-3-cyano-2-naphthol from method II-2 (8.15 g, 47.06 mmol) and 2,2',4'-trichloroacetophenone (11.57 g, 51.76 mmol, 1.1 eq) in anhydrous N,N-dimethylformamide (94 mL) was added potassium carbonate (7.80 g, 56.47 mmol, 1.2 eq), and the orange reaction mixture was stirred at 90° C. for 17 h. The resulting dark wine colored reaction was poured into ethyl acetate (500 mL) and water (300 mL). The ethyl acetate layer was washed with saturated aqueous ammonium chloride, water, and brine. The organic layer was then dried (MgSO$_4$), filtered, and evaporated in vacuo. The crude product was absorbed onto silica and purified on silica gel (flash column chromatography) eluting with 10% ethyl acetate-hexane followed by 15% ethyl acetate-hexane to collect the lower R$_f$ compound. Crystallization from ether-hexane afforded the desired benzofuran as a yellow solid (7.30 g, 43.1%). $^1$H-NMR (DMSO-d$_6$) δ 7.72 (t, J=1.4 Hz, 1H), 7.70 (s, 1H), 7.53 (d, J=0.9 Hz, 2H), 7.41 (broad s, 2H), 7.08 (s, 1H), 2.85 to 2.78 (m, 4H), 1.75 to 1.69 (m, 4H); MS LC-MS (MH$^+$=360/362); Anal. Calculated for C$_{19}$H$_{15}$Cl$_2$NO$_2$: C, 63.35%; H, 4.20%; N, 3.89%. found C, 63.23%; H, 3.98%; N, 3.83%.

The other compounds of Table 1 can be prepared in like manner to the preparation of Example 20 by employing the appropriate starting materials that are readily available and/or the synthesis of which is taught herein, and using the process described above or other standard chemical processes known in the art. A few examples are listed below:

Example 21

Preparation of the Title Compound (3-amino-6,7-dihydro-5H-1-oxa-s-indacen-2-yl)-(2,4-dichlorophenyl)methanone

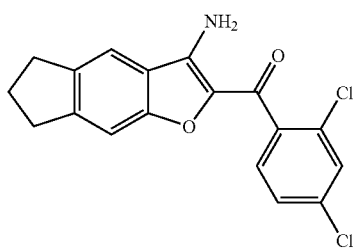

To 6-hydroxy-indan-5-carbonitrile (100 mg, 0.63 mmol) and 2,2',4'-trichloroacetophenone (141 mg, 0.63 mmol, 1.0 eq) in anhydrous N,N-dimethylformamide (4 mL) was added potassium carbonate (173 mg, 1.26 mmol, 2.0 eq). The reaction mixture was stirred under argon at 80° C. for 16 h. The brown reaction mixture was cooled and poured into ethyl acetate and water. The organic layer was washed with water, brine, dried over sodium sulfate, and concentrated at reduced pressure. The crude product was purified on the MPLC (Biotage) eluted with 30% ethyl acetate-hexane. Trituration from hexane afforded the 126.7 mg (58.1%) of the product. $^1$H-NMR (Acetone-d$_6$) δ 7.75 (d, J=0.6, 1H), 7.61 to 7.50 (m, 3H), 7.16 (d, J=0.6, 1H), 6.93 (broad s, 2H), 2.94 (m, 4H), 2.08 (m, 2H); MS ES (MH$^+$=346/348); Rf=0.70 (30% ethyl acetate-hexane).

Example 22

Preparation of (7-Amino-1,3,5-trioxa-s-indacen-6-yl)-(2,4-dichloro-phenyl)-methanone

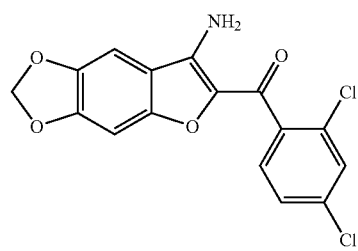

A solution of 2-hydroxy-5-hydroxymethoxy-benzonitrile (0.10 g, 0.61 mmol), 2,2',4'-trichloroacetophenone (0.16 g, 0.74 mmol, 1.2 eq) and potassium carbonate (0.13 g, 0.92 mmol, 1.5 eq) in 1 mL DMF was stirred overnight at 80° C. The reaction mixture was then partitioned between ethyl acetate and water. The organic layer was separated, washed with brine, dried with sodium sulfate and filtered through a plug of silica. Concentration in vacuo provided an orange solid, purification of which by RP-HPLC (H$_2$O-MeCN gradient) provided 0.13 g (61%) of (7-amino-1,3,5-trioxa-s-indacen-6-yl)-(2,4-dichloro-phenyl)-methanone as a yellow solid. $^1$H-NMR (DMSO-d$_6$) δ 7.70–7.69 (m, 1 H), 7.51–7.49, (m 2H), 7.42, (s, 1H) 7.30 (bs, 2H), 7.03 (s, 1H), 6.07 (s, 2H); MS LC-MS (MH$^+$=350.2/352.1), LC-MS RT=3.21 min.

Example 23

Preparation of 3-Amino-5,6,7,8-tetrahydro-naphtho-[2,3-b]furan-2-yl)benzo[1,3]dioxol-4-yl-methanone

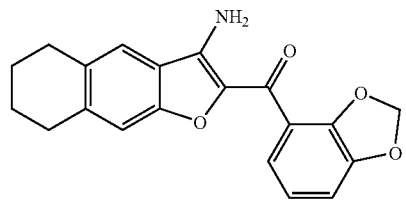

This compound was prepared using 1-Benzo[1,3]dioxol-4-yl-2-bromo-ethanone prepared in method I-7 (0.15 g, 10.62 mmol), in the manner described for 3-amino-5,6,7,8-tetrahydro-naphtho[2,3-b]furan-2-yl)(2,4-dichloro-phenyl)-methanone (Method III-1):, affording 0.36 g (21%) of 3-Amino-5,6,7,8-tetrahydro-naphtho-[2,3-b]furan-2-yl) benzo[1,3]dioxol-4-yl-methanone as a yellow solid. $^1$H-NMR (MeOH-d$_4$) δ 7.40 (s, 1H), 7.31 (dd, J=8 Hz, 1 Hz), 6.97 (dd, J=7 Hz, 1 Hz, 1H), 6.82 (s, 1H), 6.19 (s, 2H), 2.68–2.60 (m, 4H), 1.68–1.62 (m, 4H); MS LC-MS (MH$^+$=336.2), RT=3.86 min.

Example 24

Preparation of 3-Amino-2-(3-methoxy-benzoyl)-7,8-dihydro-6H-naphtho[2,3-b]furan-5-one

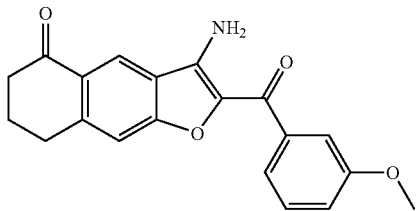

To a solution of 3-hydroxy-8-oxo-5,6,7,8-tetrahydronaphthalene-2-carbonitrile from method II-6 (45 mg, 0.24 mmol) and 3-methoxyphenacyl bromide (60 mg, 0.26 mmol, 1.1 eq) in anhydrous N,N-dimethylformamide (2 mL) was added potassium carbonate (66 mg, 0.48 mmol, 2 eq). The reaction mixture was shaken at 90° C. for 17 h. The mixture was cooled to room temperature and poured into ethyl acetate and water. The aqueous layer was extracted with ethyl acetate twice. Combined the organic layers and evaporated in vacuo. The crude product was washed with methanol and gave 19 mg (24%) of 3-Amino-2-(3-methoxy-benzoyl)-7,8-dihydro-6H-naphtho[2,3-b]furan-5-one as a yellow solid. $^1$H-NMR (DMSO-d$_6$) δ 8.72 (s, 1H), 7.68 to 7.42 (m, 5H), 7.18 to 7.14 (m, 1H), 6.33 (s, 1H), 3.84 (s, 3H), 3.07 (t, J=6.0 Hz, 2H), 2.65 (t, J=6.6 Hz, 2H), 2.50 (m, 2H); MS LC-MS (MH$^+$=336.2); Rf=0.62, 50% ethyl acetate-hexane.

Example 25

Preparation of of (3-Amino-6,7-dihydro-5H-furo[3,2-g]chromen-2-yl)-(3-methoxyl-phenyl)-methanone

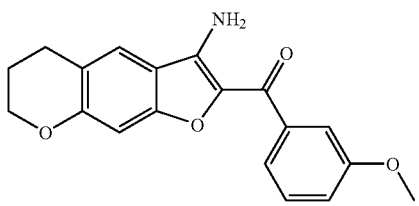

To a stirred solution of 7-Hydroxy-chroman-6-carbonitrile from method II-3 (30 mg, 0.17 mmol) and 3-methoxyphenacyl bromide (78.5 mg, 0.34 mmol, 2.0 eq) in anhydrous N,N-dimethylformamide (1.0 mL) was added potassium carbonate (47.3 mg, 0.34 mmol, 2.0 eq), and the orange reaction mixture was stirred at 100° C. for 17 h. The resulting dark wine colored reaction was poured into ethyl acetate (10 mL) and water (10 mL). This mixture was then extracted with EtOAc (2×10 mL). The combined organic layers were then dried (Na$_2$SO$_4$), filtered, and evaporated in vacuo. The residue was purified by pre-HPLC to afford the desired product as a yellow solid (30.7 mg, 54.9%). $^1$H-NMR (CD$_3$CN) δ 7.73 (d, J=7.3 Hz, 1H), 7.66 (s, 1H), 7.50 (s, 1H), 7.44 (t, 1H), 7.34 (dd, J=2.8, 8.5 Hz, 1H), 6.80 (s, 1H), 4.25 (t, 2H), 3.89 (s, 3H), 2.93 (t, 2H), 2.03 (m, 2H); MS LC-MS (MH$^+$=324).

Example 26

Preparation of of (3-Amino-7,7-dimethyl-6,7-dihydro-5H-furo[3,2,-g]chromen-2-yl)-(3-nitro-phenyl)-methanone

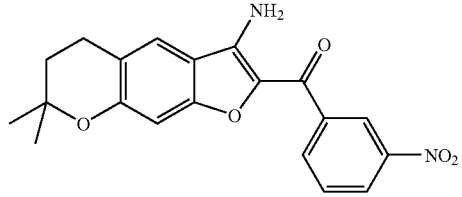

To a stirred solution of 7-Hydroxy-2,2-dimethyl-chroman-6-carbonitrile from method II-4 (30 mg, 0.15 mmol) and 2-bromo-1-(3-nitro-phenyl)-ethanone (72.1 mg, 0.30 mmol, 2.0 eq) in anhydrous N,N-dimethylformamide (1.0 mL) was added potassium carbonate (40.8 mg, 0.30 mmol, 2.0 eq), and the orange reaction mixture was stirred at 100° C. for 17 h. The resulting dark wine colored reaction was poured into ethyl acetate (10 mL) and water (10 mL). This mixture was then extracted with EtOAc (2×10 mL). The combined organics were then dried (Na$_2$SO$_4$), filtered, and evaporated in vacuo. The residue was purified by pre-HPLC to afford the desired product as a yellow solid (18.7 mg, 33.5%). $^1$H-NMR (CD$_3$CN) δ 8.89, (s, 1H), 8.54 (d, J=8.0 Hz, 1H), 8.36 (d, J=8.0 Hz, 1H), 7.75 (t 1H), 7.55 (s, 1H), 6.74, (s, 1H), 2.95 (t, 2H), 1.90 (t, 2 H), 1.38 (s, 6 H) LC-MS (MH$^+$=367).

The other compounds of Table 1 can be prepared in like manner as described above by choosing the appropriate starting materials that are readily available and/or the synthesis of which is taught herein, and using the process described above or other standard chemical processes known in the art.

TABLE 1

Examples prepared using Method III-1

| Example | Structure | Rf (TLC solvent) Or RT (min)* | LC/MS ([M + H]+) | Synth. of (III)** | Synth. of (IIa)** | Synth. of (Ia) |
|---------|-----------|-------------------------------|------------------|-------------------|-------------------|----------------|
| 27 | 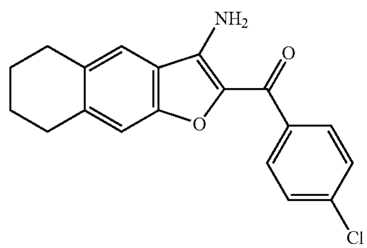 | Rf = 0.36 [25% EtOAc/HEX] | 326/328 | comm | II-2 | III-1 |
| 28 | 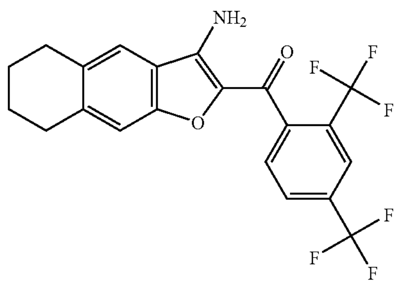 | Rf = 0.48 [25% EtOAc/HEX] | 428 | I-2 | II-2 | III-1 |
| 29 | 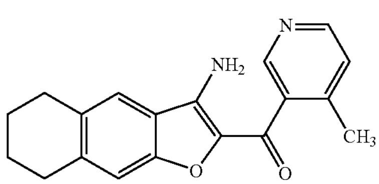 | RT = 2.23 | 307.3 | I-3 | II-2 | III-1 |
| 30 | 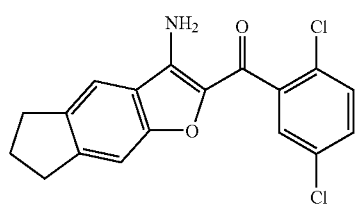 | Rf = 0.70 [30% EtOAc/HEX] | 346/348 | comm | II-2 | III-1 |
| 31 | 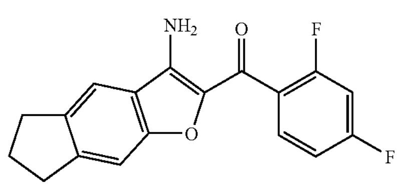 | Rf = 0.75 [25% EtOAc/HEX] | 314.3 | comm | II-2 | III-1 |
| 32 | 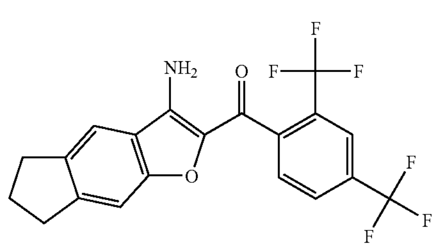 | Rf = 0.60 [30% EtOAc/HEX] | 414 | I-2 | II-2 | III-1 |

TABLE 1-continued

Examples prepared using Method III-1

| Example | Structure | Rf (TLC solvent) Or RT (min)* | LC/MS ([M + H]+) | Synth. of (III)** | Synth. of (IIa)** | Synth. of (Ia) |
|---|---|---|---|---|---|---|
| 33 | 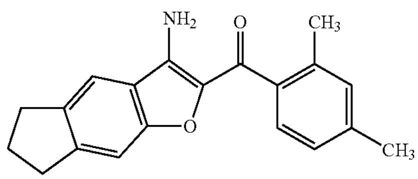 | Rf = 0.60 [30% EtOAc/HEX] | 306 | comm | II-2 | III-1 |
| 34 | 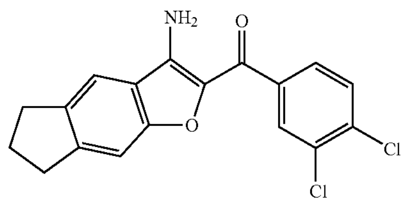 | Rf = 0.65 [30% EtOAc/HEX] | 361 | comm | II-2 | III-1 |
| 35 | 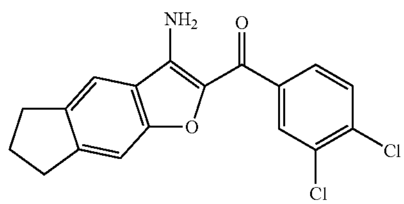 | Rf = 0.75 [30% EtOAc/HEX] | 347 | comm | II-2 | III-1 |
| 36 | 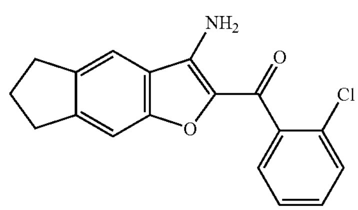 | Rf = 0.75 [25% EtOAc/HEX] | 312.3/314.3 | comm | II-2 | III-1 |
| 37 | 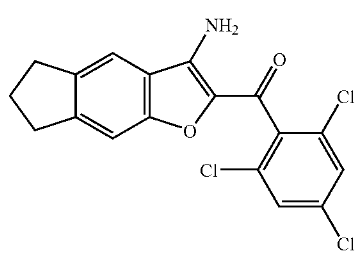 | Rf = 0.60 [30% EtOAc/HEX] | 381 | comm | II-2 | III-1 |
| 38 | 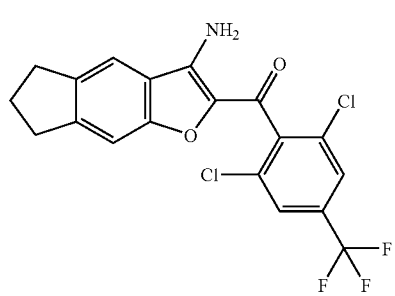 | Rf = 0.53 [30% EtOAc/HEX] | 415 | comm | II-2 | III-1 |

TABLE 1-continued

Examples prepared using Method III-1

| Example | Structure | Rf (TLC solvent) Or RT (min)* | LC/MS ([M + H]+) | Synth. of (III)** | Synth. of (IIa)** | Synth. of (Ia) |
|---|---|---|---|---|---|---|
| 39 | 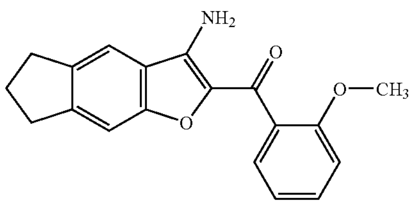 | Rf = 0.65 [30% EtOAc/HEX] | 308 | comm | II-2 | III-1 |
| 40 | 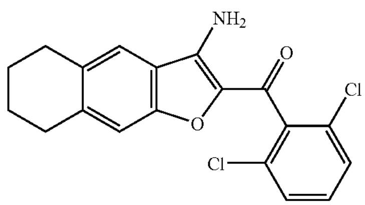 | Rf = 0.63 [30% EtOAc/HEX] | 361 | comm | II-2 | III-1 |
| 41 | 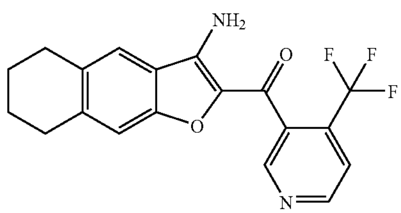 | Rf = 0.60 [50% EtOAc:HEX] RT = 3.25 | 364.4 | I-4 | II-2 | III-1 |
| 42 | 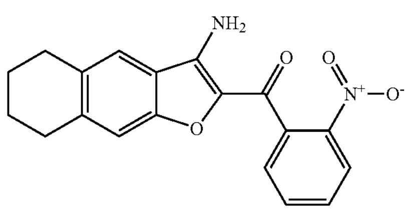 | Rf = 0.58 [30% EtOAc/HEX] | 337 | comm | II-2 | III-1 |
| 43 | 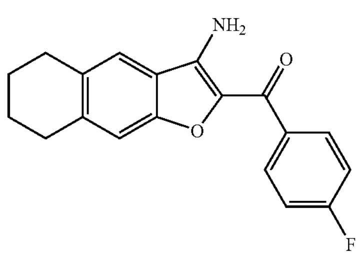 | Rf = 0.68 [30% EtOAc/HEX] | 310 | comm | II-2 | III-1 |
| 44 | 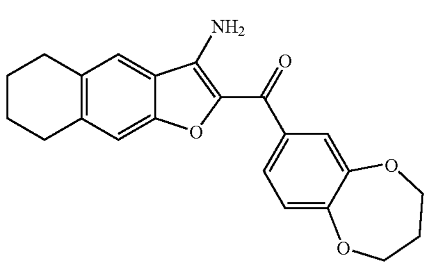 | Rf = 0.55 [30% EtOAc/HEX] | 364 | comm | II-2 | III-1 |

TABLE 1-continued

Examples prepared using Method III-1

| Example | Structure | Rf (TLC solvent) Or RT (min)* | LC/MS ([M + H]+) | Synth. of (III)** | Synth. of (IIa)** | Synth. of (Ia) |
|---|---|---|---|---|---|---|
| 45 | 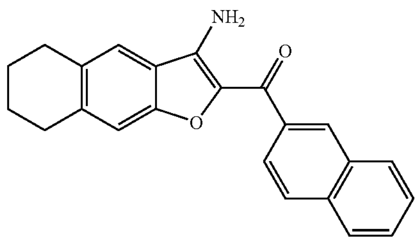 | Rf = 0.55 [30% EtOAc/HEX] | 342 | comm | II-2 | III-1 |
| 46 | 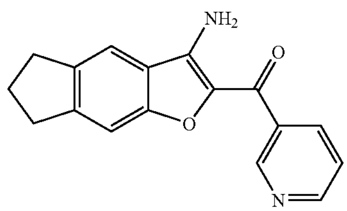 | Rf = 0.25 [30% EtOAc/HEX] | 279 | I-3 step 2 | II-2 | III-1 |
| 47 | 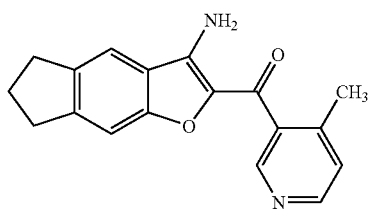 | Rf = 0.25 [30% EtOAc/HEX] | 293 | I-3 | II-2 | III-1 |
| 48 | 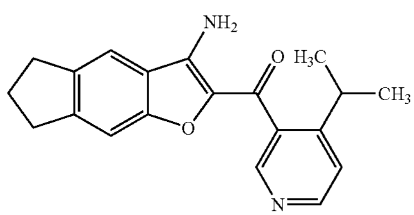 | Rf = 0.23 [30% EtOAc/HEX] | 321 | I-3 | II-2 | III-1 |
| 49 | 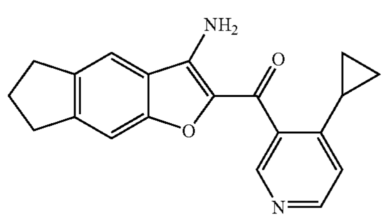 | Rf = 0.20 [30% EtOAc/HEX] | 319 | I-3 | II-2 | III-1 |
| 50 | 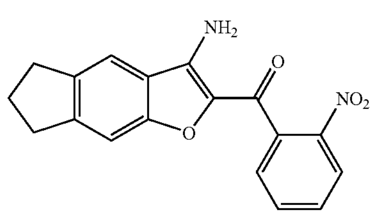 | Rf = 0.75 [30% EtOAc/HEX] | 323 | comm | II-2 | III-1 |

TABLE 1-continued

Examples prepared using Method III-1

| Example | Structure | Rf (TLC solvent) Or RT (min)* | LC/MS ([M + H]+) | Synth. of (III)** | Synth. of (IIa)** | Synth. of (Ia) |
|---|---|---|---|---|---|---|
| 51 | 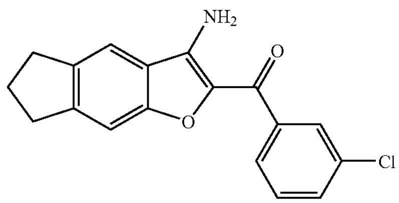 | Rf = 0.75 [30% EtOAc/HEX] | 312 | comm | II-2 | III-1 |
| 52 | 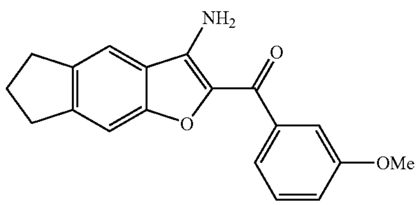 | Rf = 0.70 [30% EtOAc/HEX] | 308 | comm | II-2 | III-1 |
| 53 | 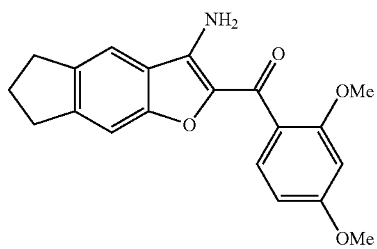 | Rf = 0.70 [30% EtOAc/HEX] | 338 | comm | II-2 | III-1 |
| 54 | 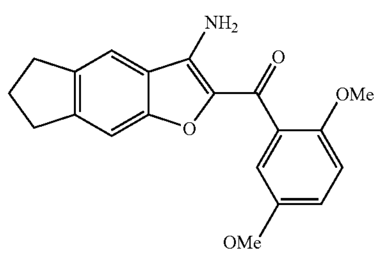 | Rf = 0.65 [30% EtOAc/HEX] | 338 | comm | II-2 | III-1 |
| 55 | 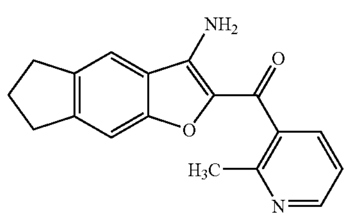 | RT = 2.30 | 293..2 | I-4 | II-2 | III-1 |
| 56 | 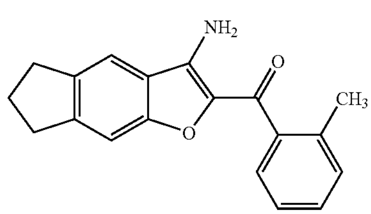 | Rf = 0.70 [30% EtOAc/HEX] | 292 | I-2 | II-2 | III-1 |

TABLE 1-continued

Examples prepared using Method III-1

| Example | Structure | Rf (TLC solvent) Or RT (min)* | LC/MS ([M + H]+) | Synth. of (III)** | Synth. of (IIa)** | Synth. of (Ia) |
|---|---|---|---|---|---|---|
| 57 | 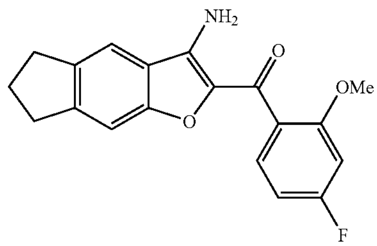 | Rf = 0.70 [30% EtOAc/HEX] | 326 | I-2 | II-2 | III-1 |
| 58 | 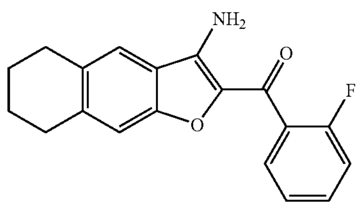 | Rf = 0.32 [25% EtOAc/HEX] | 310 | I-2 | II-2 | III-1 |
| 59 | 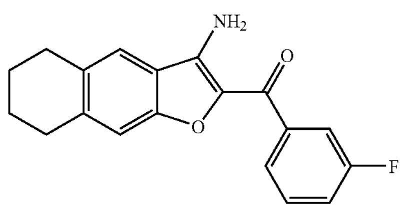 | Rf = 0.70 [30% EtOAc/HEX] | 310 | comm | II-2 | III-1 |
| 60 | 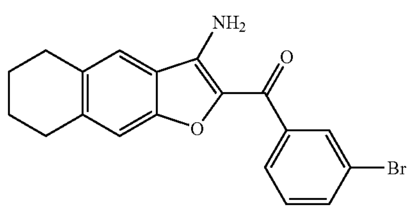 | Rf = 0.68, [30% EtOAc/HEX] | 370/372 | comm | II-2 | III-1 |
| 61 | 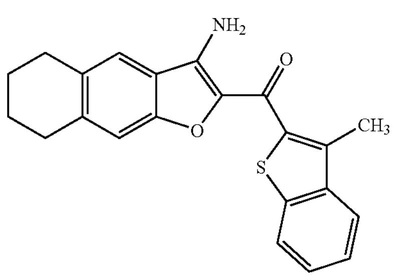 | Rf = 0.68, [30% EtOAc/HEX] | 362 | comm | II-2 | III-1 |
| 62 | 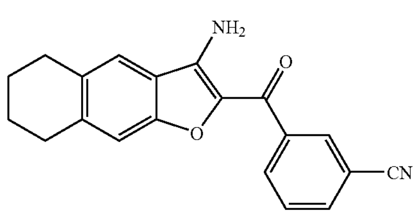 | Rf = 0.55, [30% EtOAc/HEX] | 317 | comm | II-2 | III-1 |

TABLE 1-continued

Examples prepared using Method III-1

| Example | Structure | Rf (TLC solvent) Or RT (min)* | LC/MS ([M + H]+) | Synth. of (III)** | Synth. of (IIa)** | Synth. of (Ia) |
|---|---|---|---|---|---|---|
| 63 | 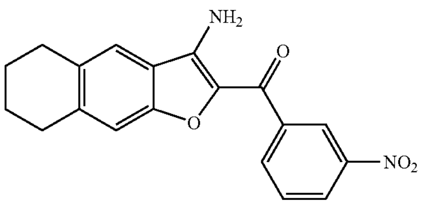 | Rf = 0.53 [30% EtOAc/HEX] | 337 | comm | II-2 | III-1 |
| 64 | 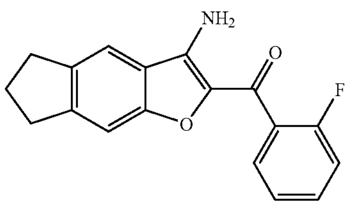 | Rf = 0.55 [30% EtOAc/HEX] | 296 | comm | II-2 | III-1 |
| 65 | 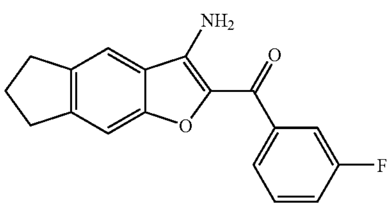 | Rf = 0.60 [30% EtOAc/HEX] | 296 | comm | II-2 | III-1 |
| 66 | 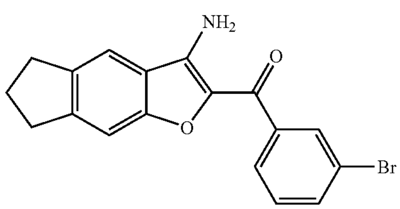 | Rf = 0.60, [30% EtOAc/HEX] | 356/358 | comm | II-2 | III-1 |
| 67 | 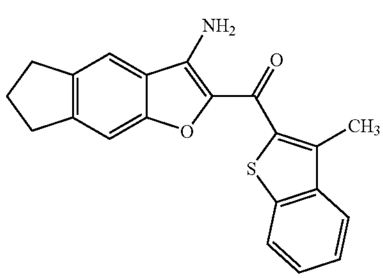 | Rf = 0.62, [30% EtOAc/HEX] | 348 | comm | II-2 | III-1 |
| 68 | 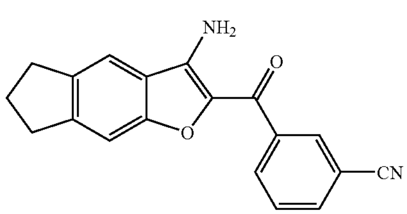 | Rf = 0.53, [30% EtOAc/HEX] | 303 | comm | II-2 | III-1 |

TABLE 1-continued

Examples prepared using Method III-1

| Example | Structure | Rf (TLC solvent) Or RT (min)* | LC/MS ([M + H]+) | Synth. of (III)** | Synth. of (IIa)** | Synth. of (Ia) |
|---|---|---|---|---|---|---|
| 69 | 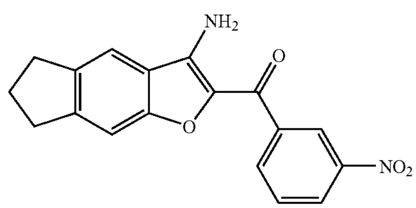 | Rf = 0.53, [30% EtOAc/HEX] | 323 | comm | II-2 | III-1 |
| 70 | 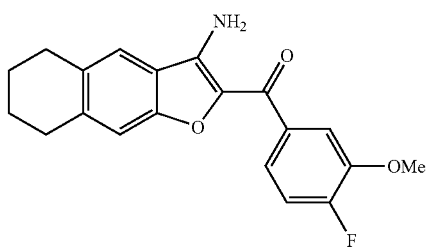 | Rf = 0.38, [30% EtOAc/HEX] | 340 | I-2 | II-2 | III-1 |
| 71 | 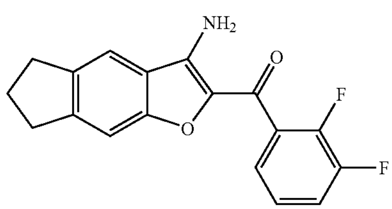 | Rf = 0.38, [30% EtOAc/HEX] | 314 | I-2 | II-2 | III-1 |
| 72 | 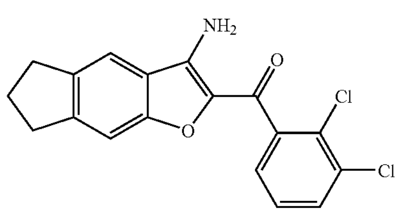 | Rf = 0.40, [30% EtOAc/HEX] | 346 | I-2 | II-2 | III-1 |
| 73 | 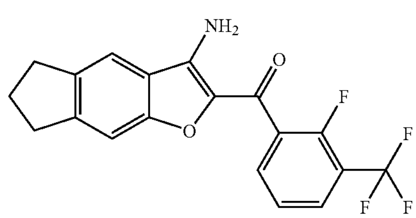 | Rf = 0.50, [30% EtOAc/HEX] | 364 | I-2 | II-2 | III-1 |
| 74 | 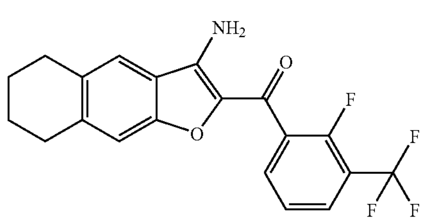 | Rf = 0.45, [30% EtOAc/HEX] | 378 | I-2 | II-2 | III-1 |

TABLE 1-continued

Examples prepared using Method III-1

| Example | Structure | Rf (TLC solvent) Or RT (min)* | LC/MS ([M + H]+) | Synth. of (III)** | Synth. of (IIa)** | Synth. of (Ia) |
|---|---|---|---|---|---|---|
| 75 | 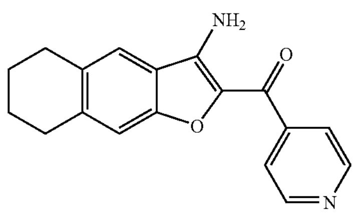 | Rf = 0.36 [75% EtOAc/HEX] RT = 2.56 | 293.4 | | II-2 | III-1 |
| 76 | 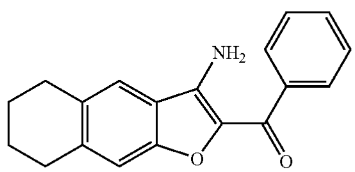 | RT = 3.18 | 292 | | II-2 | III-1 |
| 77 | 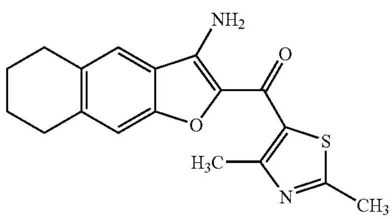 | RT = 4.46 | 327 | I-2 | II-2 | III-1 |
| 78 | 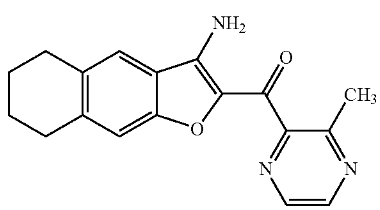 | RT = 3.6 | 308 | I-2 | II-2 | III-1 |
| 79 | 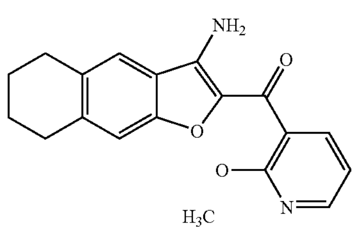 | RT = 3.01 | 323.4 | I-4 | II-2 | III-1 |
| 80 | 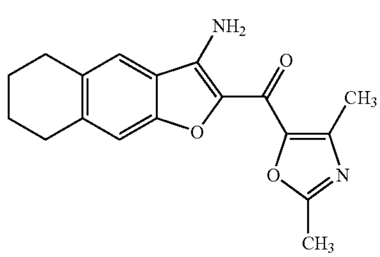 | RT = 3.31 | 311 | I-5 | II-2 | III-1 |

TABLE 1-continued

Examples prepared using Method III-1

| Example | Structure | Rf (TLC solvent) Or RT (min)* | LC/MS ([M + H]+) | Synth. of (III)** | Synth. of (IIa)** | Synth. of (Ia) |
|---|---|---|---|---|---|---|
| 81 | 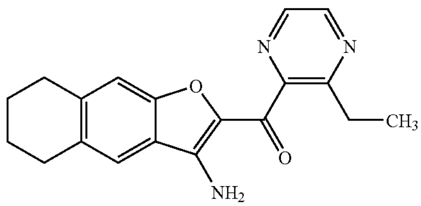 | RT = 3.28 | 322 | I-5 | II-2 | III-1 |
| 82 | 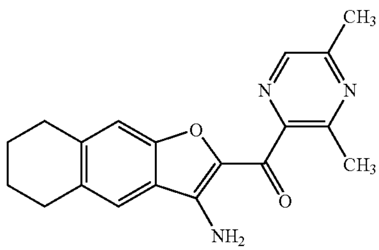 | RT = 3.22 | 322 | I-5 | II-2 | III-1 |
| 83 | 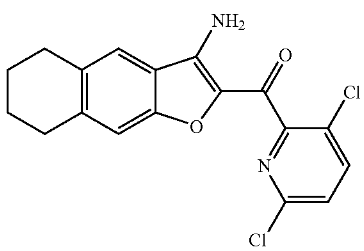 | RT = 3.84 | 361.3 | I-4 | II-2 | III-1 |
| 84 | 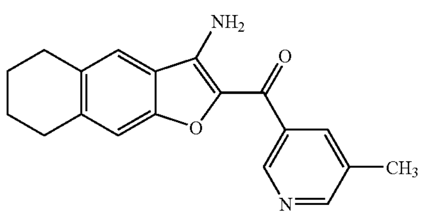 | RT = 2.4 | 307.4 | I-4 | II-2 | III-1 |
| 85 | 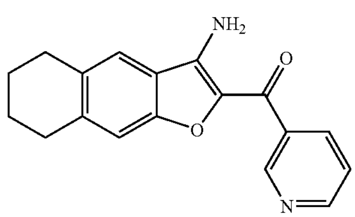 | RT = 2.4 | 293.3 | I-3 step 2 | II-2 | III-1 |
| 86 | 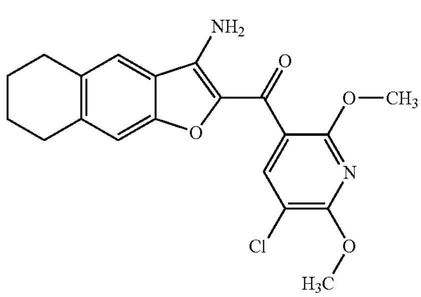 | RT = 3.74 | 387.3 | I-4 | II-2 | III-1 |

TABLE 1-continued

Examples prepared using Method III-1

| Example | Structure | Rf (TLC solvent) Or RT (min)* | LC/MS ([M + H]+) | Synth. of (III)** | Synth. of (IIa)** | Synth. of (Ia) |
|---|---|---|---|---|---|---|
| 87 | 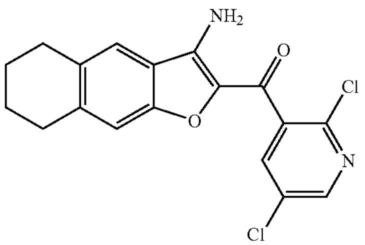 | RT = 3.52 | 361.3 | I-6 | II-2 | III-1 |
| 88 | 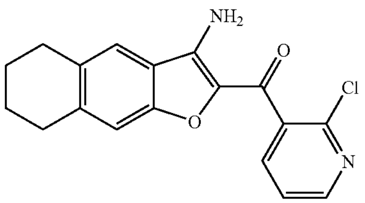 | RT = 3.08 | 327.3 | I-6 | II-2 | III-1 |
| 89 | 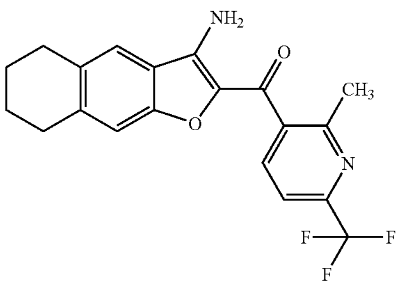 | RT = 3.65 | 375.4 | I-6 | II-2 | III-1 |
| 90 | 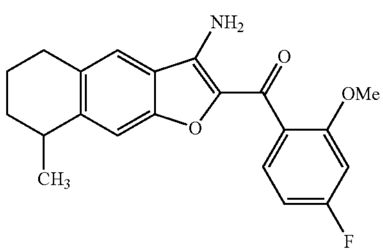 | RT = 3.65 | 354.1 | I-2 | II-2 | III-1 |
| 91 | 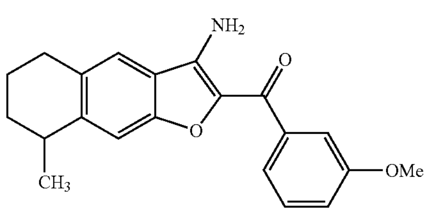 | RT = 3.8 | 336.2 | comm | II-2 | III-1 |
| 92 | 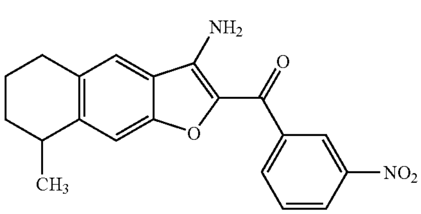 | RT = 3.85 | 351.2 | comm | II-2 | III-1 |

TABLE 1-continued

Examples prepared using Method III-1

| Example | Structure | Rf (TLC solvent) Or RT (min)* | LC/MS ([M + H]+) | Synth. of (III)** | Synth. of (IIa)** | Synth. of (Ia) |
|---|---|---|---|---|---|---|
| 93 | 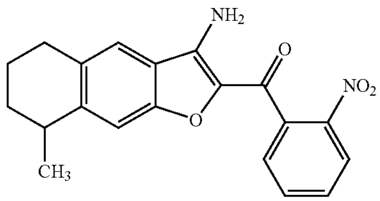 | RT = 3.48 | 351.1 | comm | II-2 | III-1 |
| 94 | 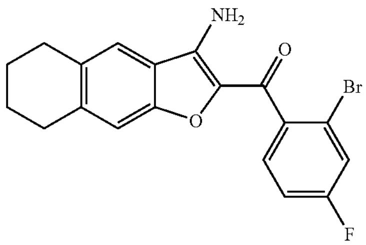 | RT = 3.67 | 388.3 | I-2 | II-2 | III-1 |
| 95 | 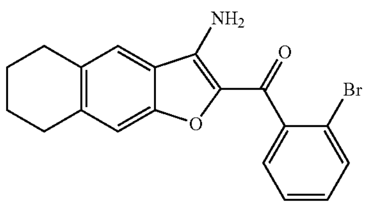 | RT = 4.04 | 370.3/372.2 | I-2 | II-2 | III-1 |
| 96 | 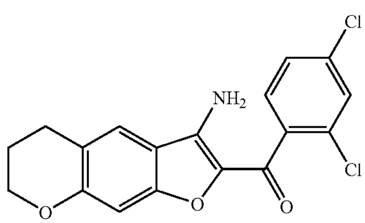 | RT = 3.62 | 362/364 | comm | II-3 | III-1 |
| 97 | 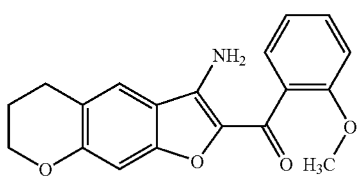 | RT = 3.24 | 324 | comm | II-3 | III-1 |
| 98 | 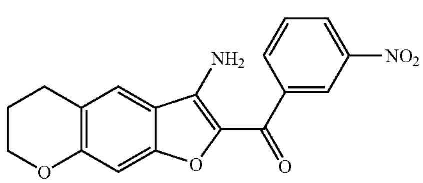 | RT = 3.53 | 339 | comm | II-3 | III-1 |
| 99 | 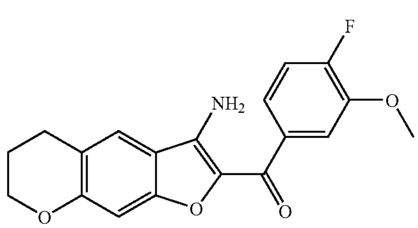 | RT = 3.57 | 342 | I-2 | II-3 | III-1 |

TABLE 1-continued

Examples prepared using Method III-1

| Example | Structure | Rf (TLC solvent) Or RT (min)* | LC/MS ([M + H]+) | Synth. of (III)** | Synth. of (IIa)** | Synth. of (Ia) |
|---|---|---|---|---|---|---|
| 100 | 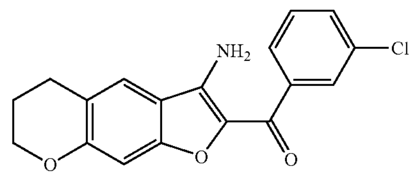 | RT = 3.84 | 328 | comm | II-3 | III-1 |
| 101 | 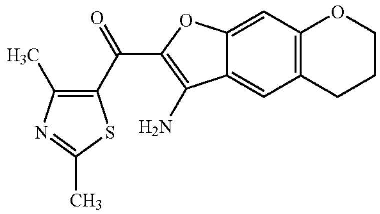 | RT = 2.59 | 329 | I-2 | II-3 | III-1 |
| 102 | 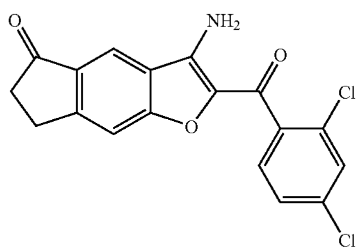 | RT = 3.32 | 360.3/362.3 | comm | II-6 | III-1 |
| 103 | 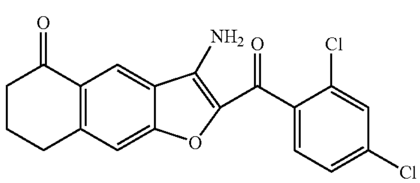 | Rf = 0.54 [50% EtOAc/HEX] RT = 3.69 | 374.3/376.3 | comm | II-6 | III-1 |
| 104 | 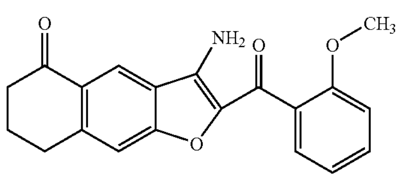 | Rf = 0.34 [50% EtOAc/HEX] | 336.3 | comm | II-6 | III-1 |
| 105 | 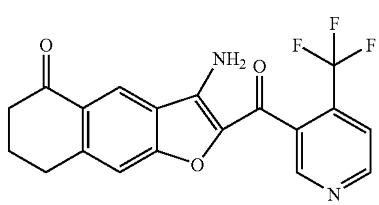 | Rf = 0.38 [50% EtOAc/HEX] | 375.3 | I-4 | II-6 | III-1 |
| 106 | 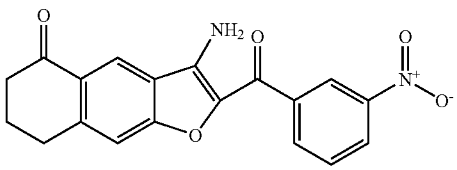 | Rf = 0.62 [50% EtOAc/HEX] | 351.2 | comm | II-6 | III-1 |

TABLE 1-continued

Examples prepared using Method III-1

| Example | Structure | Rf (TLC solvent) Or RT (min)* | LC/MS ([M + H]+) | Synth. of (III)** | Synth. of (IIa)** | Synth. of (Ia) |
|---|---|---|---|---|---|---|
| 107 | 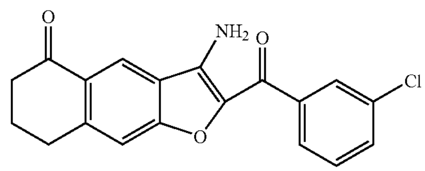 | Rf = 0.6 [50% EtOAc/HEX] | 340.2/342.2 | comm | II-6 | III-1 |
| 108 | 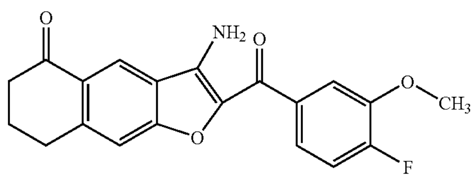 | Rf = 0.6 [50% EtOAc/HEX] | 354.1 | I-2 | II-6 | III-1 |
| 109 | 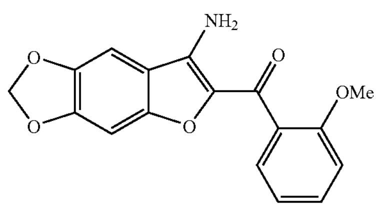 | RT = 2.96 | 312 | comm | II-7 | III-1 |

Footnotes:
*The following is the LCMS conditions:
HPLC - electrospray mass spectra (HPLC ES-MS) were obtained using a Gilson HPLC system equipped with two Gilson 306 pumps, a Gilson 215 Autosampler, a Gilson diode array detector, a YMC Pro C-18 column (2 × 23 mm, 120 A), and a Micromass LCZ single quadrupole mass spectrometer with z-spray electrospray ionization. Spectra were scanned from 120–1000 amu over 2 seconds. ELSD (Evaporative Light Scattering Detector) data was also acquired as an analog channel. Gradient elution was used with Buffer A as 2% acetonitrile in water with 0.02% TFA and Buffer B as 2% water in Acetonitrile with 0.02% TFA at 1.5 mL/min. Samples were eluted as follows: 90% A for 0.5 minutes ramped to 95% B over 3.5 minutes and held at 95% B for 0.5 minutes and then the column is brought back to initial conditions over 0.1 minutes. Total run time is 4.8 minutes.
**comm means commercially available.

Example 110 and Example 111

Method III-2

Preparation of (3-Amino-5,6,7,8-tetrahydro-naphtho[2,3-b]furan-2-yl)-(2-methyl-pyridin-3-yl)-methanone (110) and (1-Amino-6,7,8,9-tetrahydro-naphtho[2,1-b]furan-2-yl)-(2-methyl-pyridin-3-yl)-methanone (111)

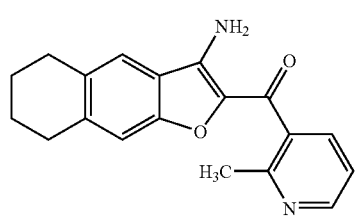

Example 110 and

Example 111

In a 7 mL vial was placed 70 mg (0.40 mmol, 1 eq) of a 1:1 mixture of 3-hydroxy-5,6,7,8-tetrahydro-naphthalene-2-carbonitrile and 2-hydroxy-5,6,7,8-tetrahydro-naphthalene-1-carbonitrile in 2 mL of DMF. To this was added 168 mg (1.21 mmol, 3 eq) of K$_2$CO$_3$ and the mixture allowed to stir for 5 min. At this point, 2-chloro-1-(2-methyl-pyridin-3-yl)-ethanone (92 mg, 0.44 mmol, 1.1 eq) was added and the vial heated at 80° C. overnight. The mixture was filtered and the DMF removed in vacuo. The residue was then dissolved in a minimal amount of CH$_3$CN where the minor isomer Example 111 was found to precipitate. The yellow solid was then filtered off and the process repeated until no further precipitation. The combined filtrates were then evaporated to provide Example 110 (95% pure). The two isomers were characterized as follows: Example 110: $^1$H-NMR (CD$_3$CN) δ 8.56 (m, 1H), 7.85 (d, 1H), 7.53 (s, 1H), 7.30 (m, 1H), 7.04 (s, 1H), 6.46 (br s, 2H), 2.93–2.88 (m, 4H), 1.86–1.80 (m, 4H), LC-MS (+esi MH$^+$=307.2, RT=2.48), TLC R$_f$=0.57 (75% EtOAc/Hex); Example 111 $^1$H-NMR (DMSO-d$_6$) δ 8.54 (dd, 1H), 7.78 (dd, 1H), 7.33 (dd, 1H), 7.16 (dd, 2H), 7.06 (br s, 2H), 3.16 (dd, 2H), 2.75 (dd, 2H), 1.86–1.71 (m, 4H), LC-MS (+esi MH$^+$=307.2, RT=2.48), TLC R$_f$=0.57 (75% EtOAc/Hex);

The other compounds of Table 2 can be prepared in like manner as described above by choosing the appropriate starting materials that are readily available and/or the synthesis of which is taught herein, and using the process described above or other standard chemical processes known in the art.

TABLE 2

Examples prepared using Method III-2

| Example | Structure | Rf (TLC solvent) Or RT (min)* | LC/MS ([M + H]$^+$) | Synth. of (III)** | Synth. of (IIa) or (IIb)** | Synth. of (Ia) or (Ib) |
|---|---|---|---|---|---|---|
| 112 | 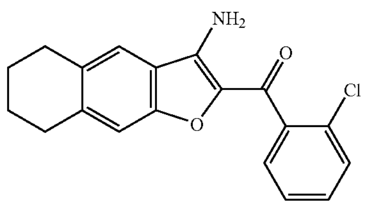 | Rf = 0.65 [25% EtOAc/HEX] | 326.3/328.3 | comm | II-1 | III-2 |
| 113 | 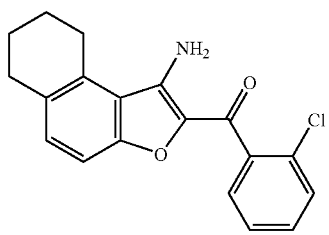 | Rf = 0.70 [30% EtOAc/HEX] | 326 | comm | II-1 | III-2 |
| 114 | 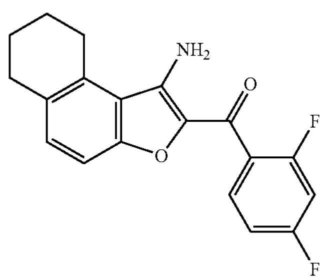 | Rf = 0.65 [30% EtOAc/HEX] | 328 | comm | II-1 | III-2 |
| 115 | 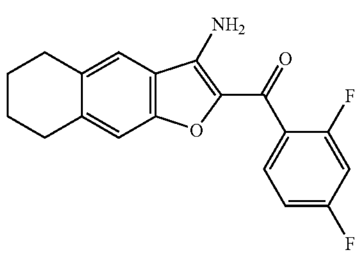 | Rf = 0.55 [25% EtOAc/HEX] | 328 | comm | II-1 | III-2 |
| 116 | 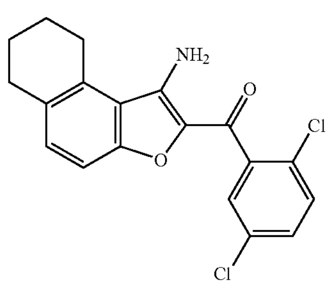 | Rf = 0.65 [30% EtOAc/HEX] | 361 | comm | II-1 | III-2 |

TABLE 2-continued

Examples prepared using Method III-2

| Example | Structure | Rf (TLC solvent) Or RT (min)* | LC/MS ([M + H]+) | Synth. of (III)** | Synth. of (IIa) or (IIb)** | Synth. of (Ia) or (Ib) |
|---|---|---|---|---|---|---|
| 117 | 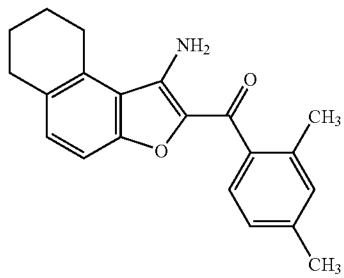 | Rf = 0.63 [30% EtOAc/HEX] | 320 | comm | II-1 | III-2 |
| 118 | 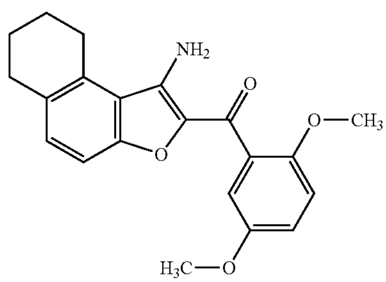 | Rf = 0.65 [30% EtOAc/HEX] | 352 | comm | II-1 | III-2 |
| 119 | 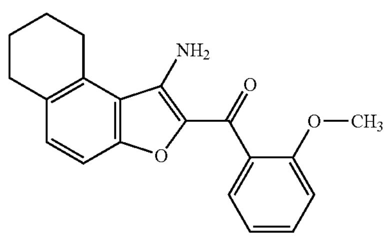 | Rf = 0.65 [30% EtOAc/HEX] | 322 | comm | II-1 | III-2 |
| 120 | 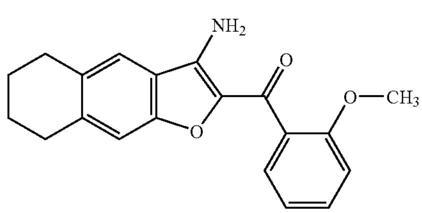 | Rf = 0.60 [30% EtOAc/HEX] | 322 | comm | II-1 | III-2 |
| 121 | 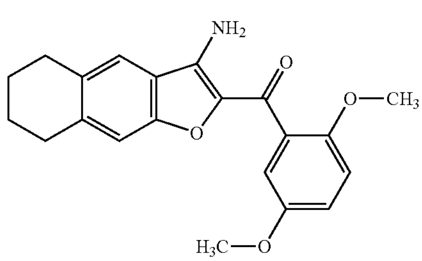 | Rf = 0.60 [30% EtOAc/HEX] | 352 | comm | II-1 | III-2 |

TABLE 2-continued

Examples prepared using Method III-2

| Example | Structure | Rf (TLC solvent) Or RT (min)* | LC/MS ([M + H]+) | Synth. of (III)** | Synth. of (IIa) or (IIb)** | Synth. of (Ia) or (Ib) |
|---|---|---|---|---|---|---|
| 122 | 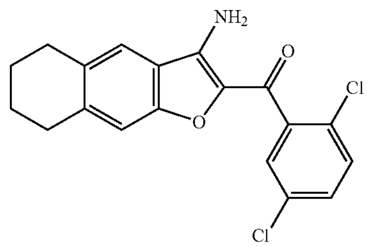 | Rf = 0.60 [30% EtOAc/HEX] | 361 | comm | II-1 | III-2 |
| 123 | 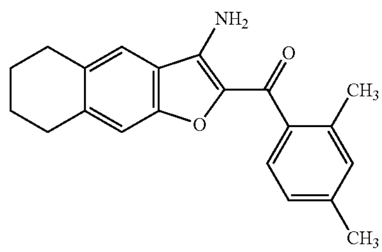 | Rf = 0.58 [30% EtOAc/HEX] | 320 | comm | II-1 | III-2 |
| 124 | 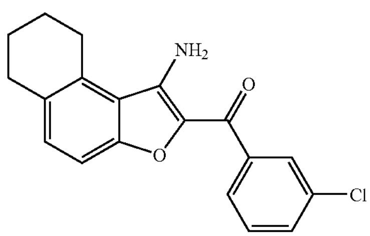 | Rf = 0.70 [30% EtOAc/HEX] | 326 | comm | II-1 | III-2 |
| 125 | 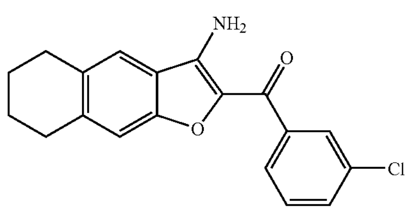 | Rf = 0.65 [30% EtOAc/HEX] | 326 | comm | II-1 | III-2 |
| 126 | 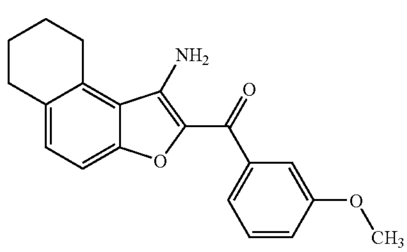 | Rf = 0.65 [30% EtOAc/HEX] | 322 | comm | II-1 | III-2 |
| 127 | 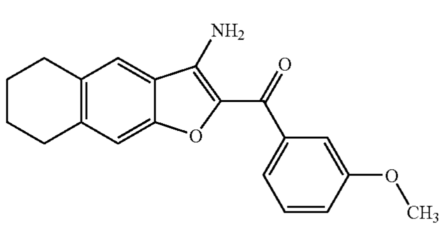 | Rf = 0.60 [30% EtOAc/HEX] | 322 | comm | II-1 | III-2 |

TABLE 2-continued

Examples prepared using Method III-2

| Example | Structure | Rf (TLC solvent) Or RT (min)* | LC/MS ([M + H]+) | Synth. of (III)** | Synth. of (IIa) or (IIb)** | Synth. of (Ia) or (Ib) |
|---|---|---|---|---|---|---|
| 128 | 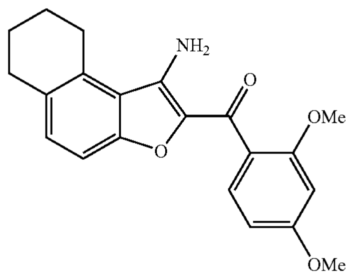 | Rf = 0.65 [30% EtOAc/HEX] | 352 | comm | II-1 | III-2 |
| 129 | 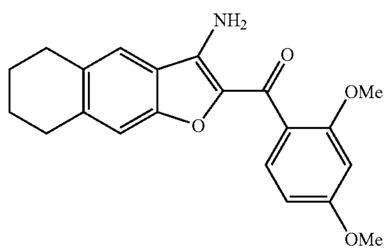 | Rf = 0.60 [30% EtOAc/HEX] | 352 | comm | II-1 | III-2 |
| 130 | 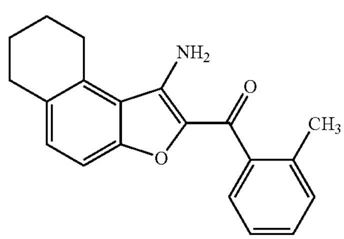 | Rf = 0.70 [30% EtOAc/HEX] | 306 | comm | II-1 | III-2 |
| 131 | 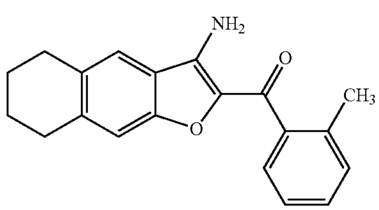 | Rf = 0.65 [30% EtOAc/HEX] | 306 | comm | II-1 | III-2 |
| 132 | 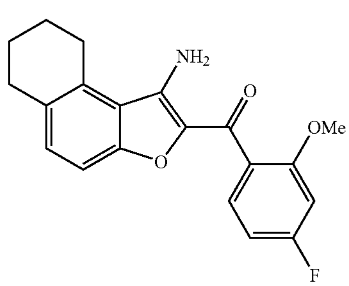 | Rf = 0.68 [30% EtOAc/HEX] | 340 | I-2 | II-1 | III-2 |

TABLE 2-continued

Examples prepared using Method III-2

| Example | Structure | Rf (TLC solvent) Or RT (min)* | LC/MS ([M + H]+) | Synth. of (III)** | Synth. of (IIa) or (IIb)** | Synth. of (Ia) or (Ib) |
|---|---|---|---|---|---|---|
| 133 | 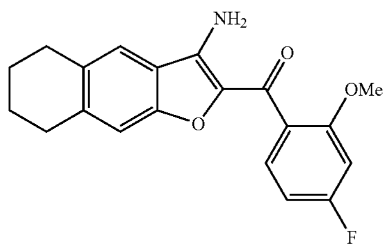 | Rf = 0.63 [30% EtOAc/HEX] | 340 | I-2 | II-1 | III-2 |
| 134 | 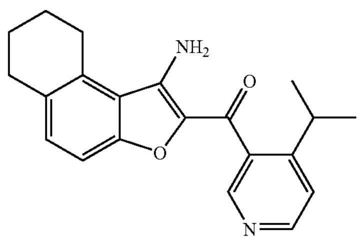 | Rf = 0.25 [30% EtOAc/HEX] | 335 | I-3 | II-1 | III-2 |
| 135 | 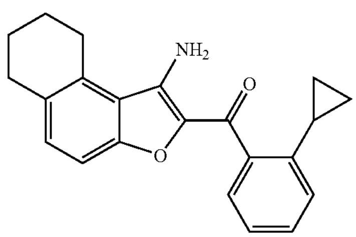 | Rf = 0.25 [30% EtOAc/HEX] | 333 | I-3 | II-1 | III-2 |
| 136 | 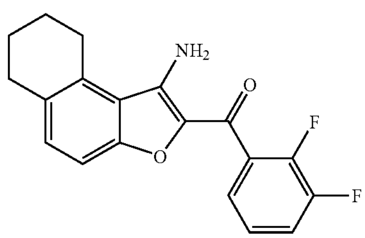 | Rf = 0.48, [30% EtOAc/HEX] | 328 | I-2 | II-1 | III-2 |
| 137 | 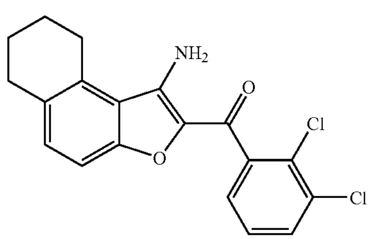 | Rf = 0.50, [30% EtOAc/HEX] | 360 | I-2 | II-1 | III-2 |
| 138 | 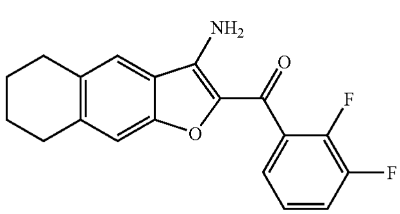 | Rf = 0.43, [30% EtOAc/HEX] | 328 | I-2 | II-1 | III-2 |

TABLE 2-continued

Examples prepared using Method III-2

| Example | Structure | Rf (TLC solvent) Or RT (min)* | LC/MS ([M + H]+) | Synth. of (III)** | Synth. of (IIa) or (IIb)** | Synth. of (Ia) or (Ib) |
|---------|-----------|-------------------------------|------------------|-------------------|----------------------------|------------------------|
| 139 | 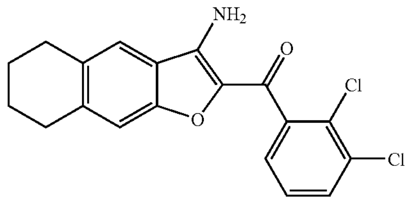 | Rf = 0.45, [30% EtOAc/HEX] | 360 | I-2 | II-1 | III-2 |

Footnotes:
*The following is the LCMS conditions:
HPLC - electrospray mass spectra (HPLC ES-MS) were obtained using a Gilson HPLC system equipped with two Gilson 306 pumps, a Gilson 215 Autosampler, a Gilson diode array detector, a YMC Pro C-18 column (2 × 23 mm, 120 A), and a Micromass LCZ single quadrupole mass spectrometer with z-spray electrospray ionization. Spectra were scanned from 120–1000 amu over 2 seconds. ELSD (Evaporative Light Scattering Detector) data was also acquired as an analog channel. Gradient elution was used with Buffer A as 2% acetonitrile in water with 0.02% TFA and Buffer B as 2% water in Acetonitrile with 0.02% TFA at 1.5 mL/min. Samples were eluted as follows: 90% A for 0.5 minutes ramped to 95% B over 3.5 minutes and held at 95% B for 0.5 minutes and then the column is brought back to initial conditions over 0.1 minutes. Total run time is 4.8 minutes.
**comm means commercially available.

Example 140 and 141

Method III-3

Preparation of 3-Amino-9-chloro-5,6,7,8-tetrahydro-naphtho[2,3-b]furan-2-yl))-(2-methyl-pyridin-3-yl)-methanone Example 140 3-Amino-4-chloro-5,6,7,8-tetrahydro-naphtho[2,3-b]furan-2-yl)-(2-methyl-pyridin-3-yl)-methanone Example 141

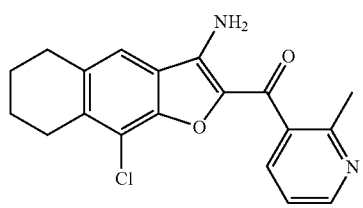

Example 140 and

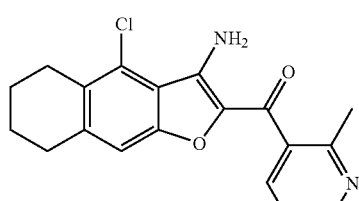

Example 141

To a stirred solution of the mixture of 4-chloro-3-hydroxy-5,6,7,8-tetrahydro-naphthalene-2-carbonitrile and 1-chloro-3-hydroxy-5,6,7,8-tetrahydro-naphthalene-2-carbonitrile 5,6,7,8-tetrahydro-3-cyano-2-naphthol prepared from method II-5 (50 mg, 0.24 mmol) and 2-bromo-1-(2-methyl-pyridin-3-yl)-ethanone (51.5 mg, 0.24 mmol, 1.0 eq) in anhydrous N,N-dimethylformamide (1.0 mL) was added DBU (109.8 mg, 0.72 mmol, 3.0 eq). The dark brown reaction mixture was stirred at 110° C. for 17 h. The reaction was then poured into ethyl acetate (10 mL) and water (10 mL). After separation of the layers, the aqueous layer was extracted with ethyl acetate (3×10 mL). The organic layers was dried (Na₂SO₄), filtered, and evaporated in vacuo. The crude product was purified first by preparative HPLC and then purified by preparative TLC with eluting solution 20% ethyl acetate-hexane. The desired products (8.8 mg, 8.0%) and (4.6 mg, 5.6%) were obtained as yellow solids. Example 140: ¹H-NMR (CD₃CN) δ 8.59 (dd, J=1.8, 4.7 Hz, 1H), 7.91 (dd, J=1.8, 7.7 Hz, 1H), 7.53 (s, 1H), 7.31 (m, 1H), 6.46 (broad s, 2H, NH₂), 2.92 (m, 4H), 2.57 (s, 3H), 1.85 (m, 4H); MS LC-MS (MH⁺=341); Example 141: ¹H-NMR (CD₃CN) δ 8.58 (dd, J=1.8, 4.7 Hz, 1H), 7.86 (dd, J=1.8, 7.7 Hz, 1H), 7.30 (m, 1H), 7.05 (s, 1H), 6.67 (broad s, 2H, NH₂), 2.88 (m, 4H), 2.55 (s, 3H), 1.84 (m, 4H); MS LC-MS (MH⁺=341).

Example 142

Method III-4

Preparation of (3-Amino-7,8-dihydro-naphtho[2,3-b]furan-2-yl)-(2,4-dichloro-phenyl)-methanone Step 1: Preparation of Starting Material 3-hydroxy-5,6-dihydro-naphthalene-2-carbonitrile

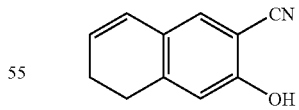

To the suspension of 3-hydroxy-8-oxo-5,6,7,8-tetrahydronaphthalene-2-carbonitrile from (150 mg, 0.8 mmol) in 2 mL anhydrous THF was added 2M LiBH4 in THF (0.6 mL, 1.2 mmol, 1.5 eq) and 0.5 mL anhydrous methanol. The reaction was shaken at 40° C. for 2 h. To this was added 5 mL water and some 1N HCl until pH=2. The mixture was extracted with ethyl acetate 3 times and dried down with genavac at high temperature. The resulting dark liquid (about 100 mg) was used directly in the next step reaction.

Step 2: Preparation of (3-Amino-7,8-dihydro-naphtho[2,3-b]furan-2-yl)-(2,4-dichloro-phenyl)-methanone

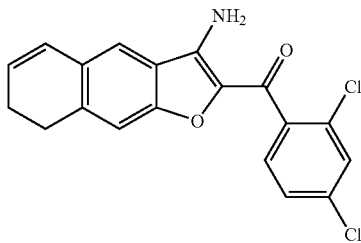

To a solution of 3-hydroxy-5,6-dihydro-naphthalene-2-carbonitrile from step 1 (100 mg, 0.58 mmol) and 2,4-dichlorophenacyl chloride (144 mg, 0.64 mmol, 1.1 eq) in anhydrous N,N-dimethylformamide (2 mL) was added potassium carbonate (161 mg, 1.2 mmol, 2 eq). The reaction mixture was shaken at 90° C. for 17 h. The mixture was cooled to room temperature and poured into ethyl acetate and water. Separated the organic phase and extracted the aqueous layer with ethyl acetate twice. Combined the ethyl acetate extracts and the original organic layer and evaporated in vacuo. The crude product was purified by HPLC and gave 39.4 mg (14% for two steps) of (3-Amino-7,8-dihydro-naphtho[2,3-b]furan-2-yl)-(2,4-dichloro-phenyl)methanone as a brown oil. $^1$H-NMR (acetone-$d_6$) δ 7.63 to 7.61 (m, 2H), 7.59 (s, 1H), 7.52 to 7.54 (m, 1H), 7.13 (s, 1H), 7.04 (broad, s, 2H), 6.59 (ft, J=10 Hz, 1.2 Hz, 1H), 6.07 (m, 1H), 2.92 (t, J=8.0 Hz, 2H), 2.33 (m, 2H); MS LC-MS (MH$^+$=358.1/360.1); Rf=0.51, 30% ethyl acetate-hexane.

Example 143

Method III-5

Preparation of (3-Amino-naphtho[2,3-b]furan-2-yl)-(2,4-dichloro-phenyl)-methanone

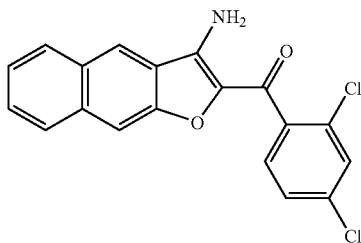

Step 1: Preparation of Starting Material acetic acid 3-carbamoyl-naphthalen-2-yl ester

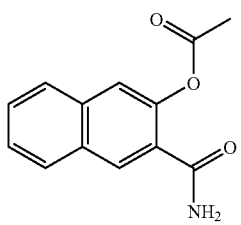

To a solution of 3-hydroxy-naphthalene-2-carboxamide (10.0 g, 53.42 mmol, 1.0 eq) in anhydrous pyridine (11 mL) at 0° C. was added acetic anhydride (6.3 mL, 66.77 mmol, 1.25 eq). The reaction mixture was stirred at room temperature for 18 h. The precipitate from the reaction was filtered and washed with hexane (4×50 mL) until the filtrate became clear, affording 10.08 g (82.3%) of the product. $^1$H-NMR (DMSO-$d_6$) δ 8.20 (s, 1H), 8.00 (d, J=7.8 Hz, 1H), 7.92 (d, J=8.4 Hz, 1H), 7.90 (s, 1H), 7.67 (s, 1H), 7.62 to 7.55 (m, 2H), 7.45 (broad s, 1H), 2.25 (s, 3H); LC-MS (ES MH$^+$=230); R$_f$=0.15 (50% ethyl acetate-hexane).

Step 2: Preparation of Starting Material 3-hydroxy-naphthalene-2-carbonitrile

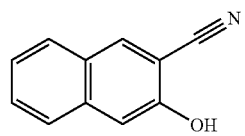

A mixture of acetic acid 3-carbamoyl-naphthalen-2-yl ester (10.08 g, 43.97 mmol, 1.0 eq) and 2.0 M thionyl chloride in dichloromethane (90 mL) was stirred at reflux for 2 h. Solvent was evaporated, and the residue was diluted in water (20 mL), methanol (400 mL), and 2N sodium hydroxide solution (75 mL). The reaction mixture was stirred at 35° C. for 2 h, acidified to pH=1 with 2N HCl, and then extracted with ethyl acetate (3×). The combined organic layers were washed with water, brine, and dried over sodium sulfate. The solvent was removed at reduce pressure and purified on the MPLC (Biotage) eluted with 20% ethyl acetate-hexane to give 4.77 g (64.6%) of the product. $^1$H-NMR (DMSO-$d_6$) δ 11.06 (s, 1H), 8.40 (s, 1H), 7.86 (d, J=8.1 Hz, 1H), 7.76 (d, J=8.0 Hz, 1H), 7.56 to 7.51 (m, 1H), 7.39 to 7.34 (m, 1H), 7.30 (s, 1H); R$_f$=0.40 (50% ethyl acetate-hexane).

Step 3: Preparation of the Title Compound: (3-Amino-naphtho[2,3-b]furan-2-yl)-(2,4-dichloro-phenyl)methanone

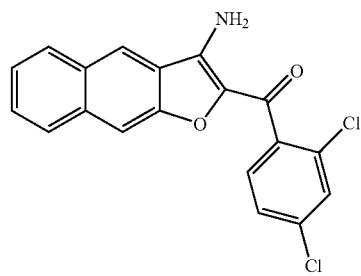

To a stirred solution of 3-hydroxy-naphthalene-2-carbonitrile from step 2 (200 mg, 1.18 mmol) and 2,2',4'-trichloroacetophenone (317 mg, 1.42 mmol, 1.2 eq) in anhydrous N,N-dimethylformamide (4.7 mL) was added potassium carbonate (326.7 mg, 2.36 mmol, 2.0 eq), and the orange reaction mixture was stirred at 80° C. for 16 h. The resulting dark wine colored reaction was diluted with ethyl acetate and water. The organic layer was washed with saturated aqueous ammonium chloride, water, brine, and dried over magnesium sulfate. The solvent was removed at reduced pressure and the crude product was purified on the MPLC (biotage) eluted with 15% ethyl acetate-hexane. Crystallization from ether-hexane afforded 243 mg (57.7%) of the desired benzofuran. $^1$H-NMR (DMSO-$d_6$) δ 8.66 (s, 1H), 7.99 (d, J=8.1 Hz, 1H), 7.93 (d, J=8.1 Hz, 1H), 7.88 (s, 1H), 7.76 (d, J=1.5 Hz, 1H), 7.72 (broad s, 2H), 7.63 to 7.42 (m, 4H); LC-MS (ES MH+=356).

Example 144

Method III-6

Preparation of 3-(3-amino-5,6,7,8-tetrahydronaphtho[2,3-b]furan-2-carbonyl)benzamide

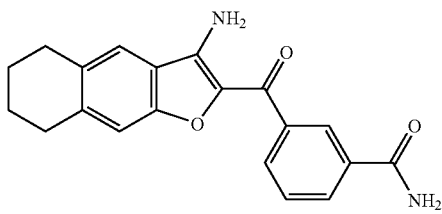

To a solution of 3-(3-amino-5,6,7,8-tetrahydronaphtho[2,3-b]furan-2-carbonyl)-benzonitrile (Example 62, 100 mg, 0.32 mmol) in acetone (5.0 mL) and water (3.0 mL) was added sodium percarbonate with 25% hydrogen peroxide (496 mg, 3.16 mmol, 10 eq). The reaction mixture was stirred at room temperature for 18 h. The volatile solvent was concentrated, and the residue was diluted with ethyl acetate, washed with water, brine, and dried over sodium sulfate. The solvent was removed at reduced pressure, and the crude product was recrystallized from ethyl acetate-hexane to afford 14.9 mg (14.1%) of the product. $^1$H-NMR (DMSO-$d_6$) δ 8.71 (d, J=1.5, 1H), 8.35 (dd, J=8.1, 1.2 Hz, 1H), 8.13 (dd, J=6.9, 1.2 Hz, 1H), 7.65 (m, 3H), 7.19 (broad, s, 2H), 7.03 (broad, s, 2H), 2.89 (m, 4H), 1.84 (m, 4H); LC-MS (ES MH+=335, RT=2.77 min). $R_f$=0.10 (50% ethyl acetate-hexane).

Example 145

Method III-7

Preparation of N-acetyl-N-[2-(2,4-dichlorobenzoyl)-5,6,7,8-tetrahydronaphtho[2,3-b]furan-3-yl]acetamide

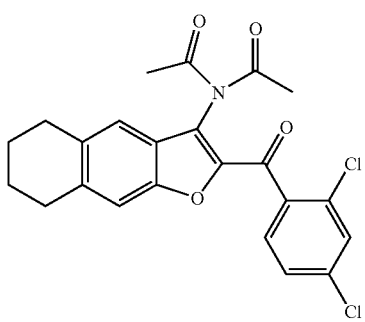

A mixture of (3-amino-5,6,7,8-tetrahydronaphtho[2,3-b]furan-2-yl)(2,4-dichlorophenyl)methanone (150 mg, 0.46 mmol) from Example 142, acetyl chloride (0.16 mL, 2.3 mmol, 5.0 eq), and diisopropylethylamine polystyrene resin (245 mg, 0.92 mmol, 2.0 eq, 3.77 mol/g loading) in dichloroethane (4.6 mL) was shaken at 70° C. for 15 h. The resin was filtered and washed with dichloromethane (2×10 mL), methanol (2×10 mL), and dichloromethane (2×10 mL). The filtrate was evaporated in vacuo. Crystallization from ether-hexane gave 73.2 mg (35.8%) as a white solid. $^1$H-NMR (DMSO-$d_6$) δ 7.82 (s, 1H), 7.62 (d, J=0.6 Hz, 1H), 7.61 (d, J=1.8 Hz, 1H), 7.46 (broad s, 2H), 2.84 (m, 4H), 2.20 (s, 6H), 1.73 (broad s, 4H); MS GC-MS (MH+=444/445); $R_f$=0.55 (25% ethyl acetate-hexane).

Example 146

Method III-8a

Preparation of N-[2-(2,4-dichlorobenzoyl)-5,6,7,8-tetrahydronaphtho[2,3-b]furan-3-yl]-acetamide

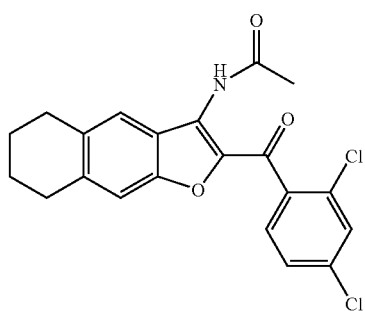

To a solution of N-acetyl-N-[2-(2,4-dichlorobenzoyl)-5,6,7,8-tetrahydronaphtho[2,3-b]furan-3-yl]-acetamide (40 mg, 0.09 mmol) in anhydrous THF (1.8 mL) was added 2N sodium hydroxide solution (1.8 mL), and the reaction mixture was stirred at 100° C. for 1 h. The reaction was diluted with ethyl acetate, washed with saturated aqueous ammonium chloride solution, water, and brine. The organic layer was then dried over sodium sulfate, filtered, and evaporated under reduced pressure. The crude product was purified on the MPLC (Biotage) eluted with 5% ethyl acetate-hexane to afford 24.5 mg (67.6%) as yellow foam. $^1$H-NMR (DMSO-$d_6$) δ 10.22 (s, 1H), 7.79 (t, J=1.2 Hz, 1H), 7.62 (s, 1H), 7.58 (d, J=0.9 Hz, 2H), 7.30 (s, 1H), 2.84 to 2.79 (m, 4H), 2.06 (s, 3H), 1.74 to 1.72 (m, 4H); LC-MS (ES MH+=402); $R_f$=0.68 (25% ethyl acetate-hexane).

Example 147

Method II-8b

Preparation of (3-Amino-8-benzyl-5,6,7,8-tetrahydro-furo[3,2-g]quinolin-2-yl)-(2,4-dichloro-phenyl)-methanone

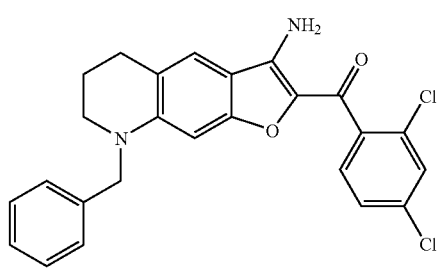

Step 1: Preparation of Intermediate 1,2,3,4-Tetrahydro-quinolin-7-ol

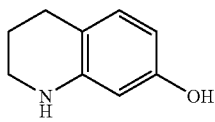

PtO$_2$ (528 mg, 2.33 mmol) was added to a dry flask. Ethanol (70 mL), tetrahydrofuran (70 mL), and hydrogen chloride (7.6 mL, 2N) were added after the flask was flushed with argon. Quinolin-7-ol (1000 mg, 6.89 mmol) was added into the flask under argon atmosphere. The solution was degassed and flashed with argon. Hydrogen gas was introduced to the flask by a balloon. The mixture was stirred at H2 atmosphere at room temperature overnight. The mixture was filtered and the filtrate was concentrated. The resulting residue was purified by MPLC (biotage) to afford 730 mg (71%) of the title compound. $^1$H-NMR (CDCl$_3$) δ 6.77 (d, J=7.6 Hz, 1H), 6.10 (dd, J=8.0 Hz, 2.8 Hz, 1H), 5.95 (d, J=2.4 Hz, 1H), 3.24 (t, J=5.9 Hz, 2H), 2.66 (t, J=5.9 Hz, 2H), 2.44 (m, 2H); R$_f$=0.74, 50% ethyl acetate-hexane.

Step 2: Preparation of Intermediate 1-benzyl-1,2,3,4-tetrahydro-quinolin-7-ol

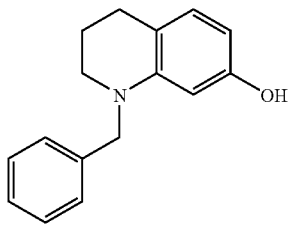

To a solution of 1,2,3,4-tetrahydro-quinolin-7-ol (200 mg, 1.34 mmol) from step 1 in anhydrous N,N-dimethyl-formamide (5 mL) was added bromomethyl-benzene (229 mg, 1.34 mmol), and potassium carbonate (556 mg, 4.02 mmol). The reaction mixture was stirred at 60° C. overnight. Added some water to the reaction mixture and extracted it with methylene chloride several times. The organic layer was combined, dried over magnesium sulfate, and filtrated. The solution was evaporated under vacuum. The crude residue was purified by MPLC (biotage) to afford 297 mg (93%) of the title compound. $^1$H-NMR (CDCl3) δ 7.35–7.20 (m, 5H), 6.81 (d, J=8.1 Hz, 1H), 6.05 (dd, J=7.8 Hz, 2.2 Hz, 1H), 5.98 (d, 2.5 Hz, 1H), 4.53 (bs, 1H), 4.44 (s, 2H), 3.34 (t, J=5.0 Hz, 2H), 2.73 (t, J=5.8 Hz, 2H), 1.98 (m, 2H); MS LC-MS (MH$^+$=240.1), LC MS RT: 3.08 min.

Step 3: Preparation of Intermediate 1-benzyl-7-hydroxy-1,2,3,4-tetrahydro-quinoline-6-carbaldehyde

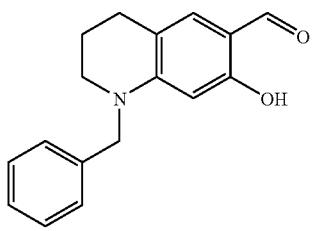

To a solution of 1-benzyl-1,2,3,4-tetrahydro-quinolin-7-ol (297 mg, 1.24 mmol) from step 2 in anhydrous acetonitrile (6 mL) was added magnesium chloride (177 mg, 1.86 mmol), triethylamine (650 µl, 4.65 mmol) and paraformaldehyde (251 mg, 8.38 mmol). The reaction mixture was reflux for a half hour. Added some water and saturated aqueous ammonium chloride until pH=7. Extracted it with ether several times. The organic layer was combined, dried over magnesium sulfate, and filtrated. The solution was evaporated under vacuum. The crude residue was purified by prep TLC eluting with 25% ethyl acetate-hexane and providing 50 mg (15%) of the title compound. $^1$H-NMR (CDCl3) δ 11.4 (s, 1H), 9.38 (s, 1H), 7.30–7.20 (m, 3H), 7.14–7.10 (m, 2H), 6.94 (s, 1H), 5.93 (s, 1H), 4.48 (s, 2H), 3.36 (t, J=5.5 Hz, 2H), 2.68 (t, J=6.2 Hz, 2H), 1.93 (m, 2H); MS LC-MS (MH$^+$=268.5), LC MS RT: 3.24 min.

Step 4: Preparation of Intermediate 1-benzyl-7-hydroxy-1,2,3,4-tetrahydro-quinoline-6-carbonitrile

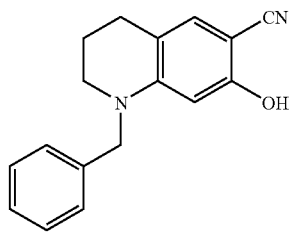

To a solution of 1-benzyl-7-hydroxy-1,2,3,4-tetrahydro-quinoline-6-carbaldehyde (45 mg, 0.17 mmol) from step 3 in acetic acid (0.38 mL, 6.6 mmol) was added nitroethane (0.24 mL, 3.4 mmol) and sodium acetate (270 mg, 3.4 mmol). The reaction mixture was heated at a sealed tube at 115° C. overnight. Added some water and extracted it with ether. Combined organic layer and evaporated under vacuum. It was purified by prep TLC eluting with 10% ethyl acetate-hexane and providing 20 mg (45%) of the title compound. $^1$H-NMR (CDCl3) δ 7.36–7.21 (m, 3H), 7.18–7.14 (m, 2H), 6.99 (s, 1H), 5.98 (s, 1H), 4.48 (s, 2H), 3.41 (t, J=5.7 Hz, 2H), 2.70 (t, J=6.4 Hz, 2H), 1.97 (m, 2H).

Step 5: Preparation of (3-Amino-8-benzyl-5,6,7,8-tetrahydro-furo[3,2-g]quinolin-2-yl)-(2,4-dichloro-phenyl)methanone

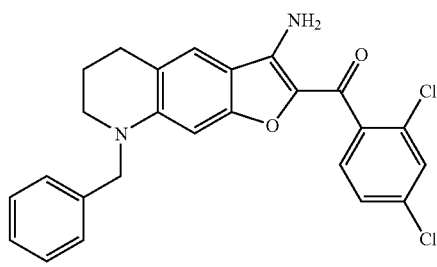

This compound was prepared from 1-benzyl-7-hydroxy-1,2,3,4-tetrahydro-quinoline-6-carbonitrile (20 mg, 0.08 mmol) from step 4 in the manner described for [(3-amino-6-iodo-benzofuran-2-yl)-(2,4-dichloro-phenyl)-methanone, affording 10 mg (29%) of the title compound as a yellow solid. $^1$H-NMR (CDCl3) δ 7.44–7.40 (m, 2H), 7.33–7.22 (m, 4H), 7.18 (s, 1H), 7.15–7.13 (m, 2H), 6.25 (s, 1H), 5.96

(bs, 2H), 4.52 (s, 2H), 3.47 (t, J=6.0 Hz, 2H), 2.89 (t, J=5.9 Hz, 2H), 2.03 (m, 2H); MS LC-MS (MH⁺=451.3), LC MS RT: 3.81 min.

Example 148

Method III-9

Preparation of (3-amino-6,7-dihydro-5H-1-oxa-s-indacen-2-yl)-(3-amino-phenyl)-methanone

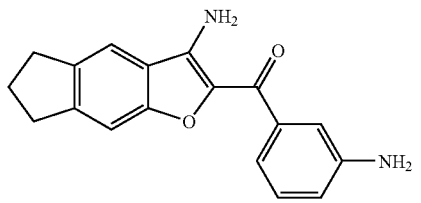

To an oven dried flask was placed 10% Pd/C (4.0 mg, 0.01 eq), evacuate air and filled the flask with argon. (3-amino-6,7-dihydro-5H-1-oxa-s-indacen-2-yl)-(3-amino-phenyl)-methanone (120 mg, 0.37 mmol) in 1:1=v/v ethyl acetate/ethanol (100 mL) was added to the flask. Stir the reaction mixture under H2 for 18 h. The reaction mixture was filtered through a pad of celite, rinsed the pad of celite well with EtOAc. Concentrate the solution, the product was purified by MPLC (Biotage), eluting with 70/30=v/v hexane/ethyl acetate, followed by trituration from hexane, to give the product as a yellow solid (38.2 mg, 35.1%). 1H-NMR (Acetone-d6) δ7.72 (s, 1H), 7.49 (m, 2H), 7.30 (s, 1H), 7.23 (m, 1H), 6.88 (broad, s, 3H), 4.83 (broad, s, 2H), 2.98 (m, 4H), 2.10 (m, 2H); MS ES (MH+=293); Rf=0.25, Hexanes/EtOAc=50/50.

The other compounds of Table 3 can be prepared in like manner as described above (method III-3 to III-9) by choosing the appropriate starting materials that are readily available and/or the synthesis of which is taught herein, and using the process described above or other standard chemical processes known in the art.

TABLE 3

Examples prepared using Method III-2 through III-9

| Example | Structure | Rf (TLC solvent) Or RT (min)* | LC/MS ([M + H]⁺) | Synth. of (III)** | Synth. of (IIa)** | Synth. of (Ia) |
|---|---|---|---|---|---|---|
| 149 | 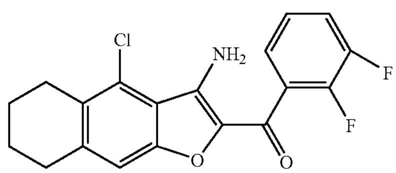 | RT = 4.11 | 362 | comm | II-5 | III-3 |
| 150 | 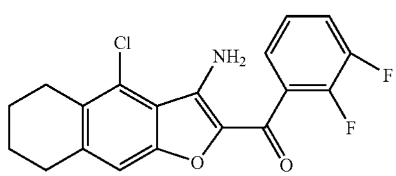 | RT = 4.23 | 371 | comm | II-5 | III-3 |
| 151 | 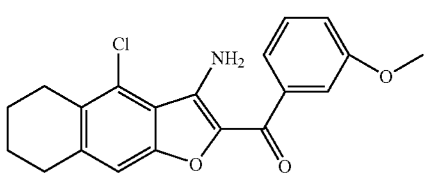 | RT = 4.23 | 356 | comm | II-5 | III-3 |
| 152 | 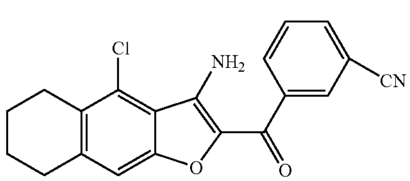 | RT = 3.92 | 351 | comm | II-5 | III-3 |
| 153 | 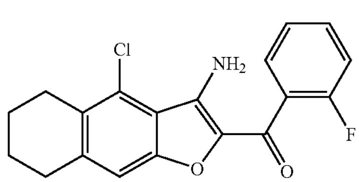 | RT = 4.03 | 344 | I-2 | II-5 | III-3 |

TABLE 3-continued

Examples prepared using Method III-2 through III-9

| Example | Structure | Rf (TLC solvent) Or RT (min)* | LC/MS ([M + H]+) | Synth. of (III)** | Synth. of (IIa)** | Synth. of (Ia) |
|---|---|---|---|---|---|---|
| 154 | (structure: 4-chloro tetrahydronaphthofuran with NH2 and 2,4-dimethylbenzoyl) | RT = 4.33 | 354 | comm | II-5 | III-3 |
| 155 | (structure: tetrahydronaphthofuran with NH2 and 3-aminobenzoyl) | Rf = 0.38 [50% EtOAc/HEX] | 307 | comm | II-2 | III-9 |
| 156 | (structure: tetrahydronaphthofuran with benzamide-NH and 2,4-dichlorobenzoyl) | Rf = 0.28 [5% EA/HEX] | Elemental Analysis for C26H19Cl2NO3: % C 66.6% H 4.20% N 2.99. Found % C 66.61 % H 4.17 % N 2.99 | comm | II-2 | III-8 |

Footnotes:
*The following is the LCMS conditions:
HPLC - electrospray mass spectra (HPLC ES-MS) were obtained using a Gilson HPLC system equipped with two Gilson 306 pumps, a Gilson 215 Autosampler, a Gilson diode array detector, a YMC Pro C-18 column (2 × 23 mm, 120 A), and a Micromass LCZ single quadrupole mass spectrometer with z-spray electrospray ionization. Spectra were scanned from 120–1000 amu over 2 seconds. ELSD (Evaporative Light Scattering Detector) data was also acquired as an analog channel. Gradient elution was used with Buffer A as 2% acetonitrile in water with 0.02% TFA and Buffer B as 2% water in Acetonitrile with 0.02% TEA at 1.5 mL/min. Samples were eluted as follows: 90% A for 0.5 minutes ramped to 95% B over 3.5 minutes and held at 95% B for 0.5 minutes and then the column is brought back to initial conditions over 0.1 minutes. Total run time is 4.8 minutes.
**comm means commercially available.

Example 157

Method IV Preparation of Benzothiophene

Preparation of (3-amino-5,6,7,8-tetrahydro-naphtho[2,3-b]thiophen-2-yl)-(2,4-dichlorophenyl)methanone

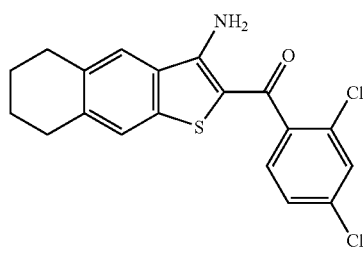

Step 1: Preparation of Dimethylthiocarbamic Acid O-(3-cyano-5,6,7,8-tetrahydro-naphthalen-2-yl)ester To a solution of 3-hydroxy-5,6,7,8-tetrahydronaphthalene-2-carbonitrile prepared in method II-2 (3.00 g, 17.3 mmol) in acetone (60 mL) was added dropwise a solution of potassium hydroxide (1.07 g, 19.1 mmol, 1.1 eq) in water (40 mL) at 0° C. After stirring for 45 min, a solution of dimethylthiocarbamoyl chloride (2.35 g, 19.1 mmol, 1.1 eq) in acetone (40 mL) was added at 0° C. over 30 min. The reaction mixture was then stirred at room temperature for 16 h, and poured into ethyl acetate and water. The organic layer was washed with saturated aqueous ammonium chloride, water, and brine. The combined aqueous wash was re-extracted with ethyl acetate, and the organic washes were dried over magnesium sulfate and evaporated at reduced pressure. The crude oil was crystallized from ether/hexane to give dimethyl-thiocarbamic acid O-(3-cyano-5,6,7,8-tetrahydro-naphthalen-2-yl) ester (2.90 g, 64.3%) as a beige solid. $^1$H-NMR (Acetone-$d_6$) δ 7.46 (s, 1H), 6.98 (s, 1H), 3.43 (d, J=4.2 Hz, 6H), 2.80 (m, 4H), 1.81 (m, 4H); MS ES (MH$^+$=261). R$_f$=0.70 (30% ethyl acetate-hexane).

Step 2: Preparation of dimethyl-thiocarbamic acid S-(3-cyano-5,6,7,8-tetrahydro-naphthalen-2-yl)ester

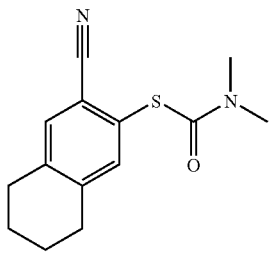

Dimethyl-thiocarbamic acid O-(3-cyano-5,6,7,8-tetrahydro-naphthalen-2-yl)ester (2.90 g, 11.1 mmol) was heated to a melt at 190° C. under argon for 6 h. The reaction was cooled to room temperature, and the resultant brown solid was purified on the MPLC (Biotage) eluted with 20% ethyl acetate-hexane to give dimethylthiocarbamic acid S-(3-cyano-5,6,7,8-tetrahydronaphthalen-2-yl)ester as a white solid (2.30 g; 79.3%). $^1$H-NMR (Acetone-d$_6$) δ 7.55 (s, 1H), 7.36 (s, 1H), 3.05 (broad d, 6H), 2.83 (m, 4H), 1.82 (m, 4H); MS ES (MH$^+$=261.0), R$_f$=0.45, 30% ethyl acetate-hexane).

Step 3: Preparation of 3-mercapto-5,6,7,8-tetrahydronaphthalene-2-carbonitrile

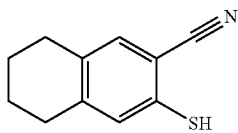

To a solution of dimethylthiocarbamic acid S-(3-cyano-5,6,7,8-tetrahydronaphthalen-2-yl) ester (1.00 g, 3.84 mmol) in anhydrous N,N-dimethylformamide (10 mL) under argon was added dropwise 25% sodium methoxide in methanol (2.6 mL, 11.5 mmol, 3.0 eq) at 0° C. The resultant yellow reaction mixture was stirred at room temperature for 1 h. The reaction mixture was poured into cold 2N HCl (100 mL) and then extracted with ethyl acetate. The combined organic layers were dried over magnesium sulfate and evaporated at reduced pressure to give 700 mg (96%) of crude 3-mercapto-5,6,7,8-tetrahydronaphthalene-2-carbonitrile.

Step 4: Preparation of the Title Compound: (3-amino-5,6,7,8-tetrahydronaphtho[2,3-b]thiophen-2-yl)-(2,4-dichlorophenyl)methanone

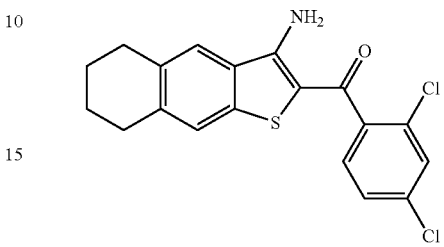

To a solution of crude 3-mercapto-5,6,7,8-tetrahydronaphthalene-2-carbonitrile (121 mg, 0.64 mmol) and 2,2',4'-trichloroacetophenone (143 mg, 0.64 mmol, 1.0 eq) in anhydrous N,N-dimethylformamide (5 mL) was added powdered potassium hydroxide (177 mg, 1.28 mmol, 2.0 eq). The reaction mixture was stirred under argon at 80° C. for 16 h. The brown reaction mixture was cooled and poured into ethyl acetate and water. The organic layer was washed with water, brine, and dried over magnesium sulfate. The solvent was removed at reduced pressure, and the crude product was purified on the MPLC (Biotage), eluted with 30% ethyl acetate-hexane. Trituration from hexane afforded 92.4 mg (38.4%) of the benzothiophene. $^1$H-NMR (Acetone-d$_6$) δ 7.88 (broad, s, 3H), 7.62 (d, J=1.5 Hz, 1H), 7.53 (m, 2H), 7.42 (s, 1H), 2.85 (m, 4H), 1.83 (m, 4H); MS ES (MH$^+$=376/378); R$_f$=0.60 (30% ethyl acetate-hexane).

The other compounds of Table 4 can be prepared in like manner to the preparation of except that the right hand portion of the molecule of (as it appears in Table 4) can be changed by employing the appropriate starting materials that are readily available and/or the synthesis of which is taught herein, and using the process described above or other standard chemical processes known in the art.

TABLE 4

Examples prepared using Method IV

| Example | Structure | Rf (TLC solvent) Or RT (min)* | LC/MS ([M + H]$^+$) | Synth. of (III)** | Synth. of (IIa)** | Synth. of (Ia) |
|---|---|---|---|---|---|---|
| 158 | (structure shown) | Rf = 0.25, [30% EtOAc/HEX] | 323 | I-4 | IV | IV |

TABLE 4-continued

Examples prepared using Method IV

| Example | Structure | Rf (TLC solvent) Or RT (min)* | LC/MS ([M + H]+) | Synth. of (III)** | Synth. of (IIa)** | Synth. of (Ia) |
|---|---|---|---|---|---|---|
| 159 | 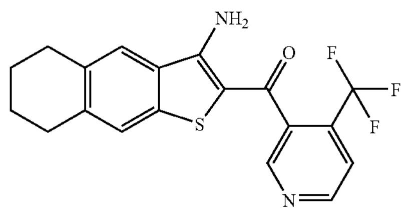 | Rf = 0.38, [30% EtOAc/HEX] | 377 | I-4 | IV | IV |
| 160 | 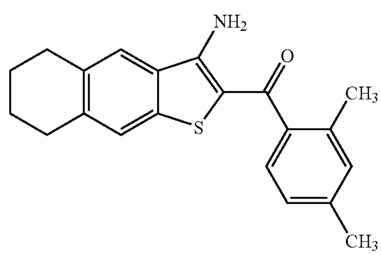 | Rf = 0.65, [30% EtOAc/HEX] | 336 | comm | IV | IV |
| 161 | 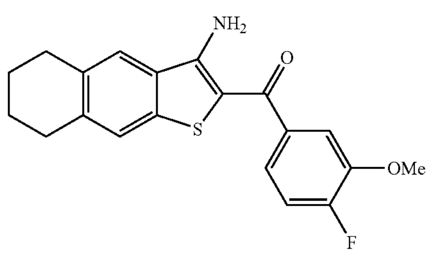 | Rf = 0.60, [30% EtOAc/HEX] | 356 | I-2 | IV | IV |
| 162 | 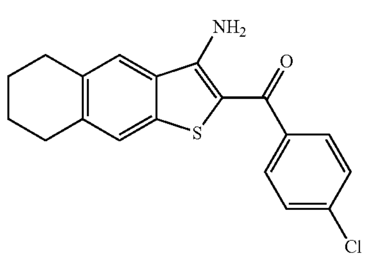 | Rf = 0.62, [30% EtOAc/HEX] | 342/344 | comm | IV | IV |
| 163 | 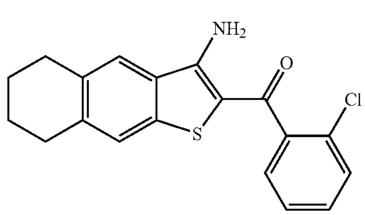 | Rf = 0.52, [30% EtOAc/HEX] | 342/344 | comm | IV | IV |

TABLE 4-continued

Examples prepared using Method IV

| Example | Structure | Rf (TLC solvent) Or RT (min)* | LC/MS ([M + H]+) | Synth. of (III)** | Synth. of (IIa)** | Synth. of (Ia) |
|---|---|---|---|---|---|---|
| 164 | 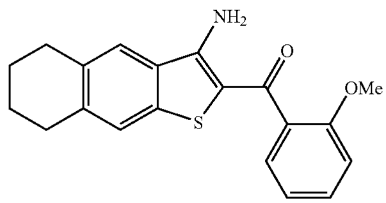 | Rf = 0.38, [30% EtOAc/HEX] | 338 | comm | IV | IV |
| 165 | 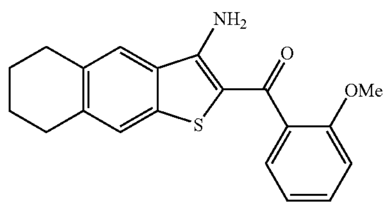 | Rf = 0.45, [30% EtOAc/HEX] | 338 | comm | IV | IV |
| 166 | 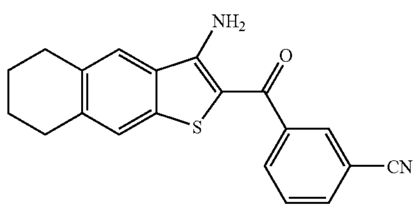 | Rf = 0.40, [30% EtOAc/HEX] | 333 | comm | IV | IV |
| 167 | 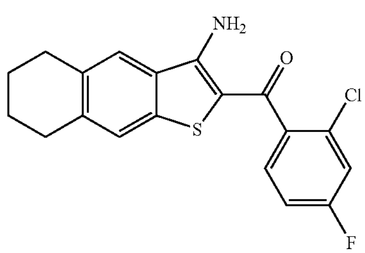 | Rf = 0.40, [30% EtOAc/HEX] | 360/362 | I-2 | IV | IV |

Footnotes:
*The following is the LCMS conditions:
HPLC - electrospray mass spectra (HPLC ES-MS) were obtained using a Gilson HPLC system equipped with two Gilson 306 pumps, a Gilson 215 Autosampler, a Gilson diode array detector, a YMC Pro C-18 column (2 × 23 mm, 120 A), and a Micromass LCZ single quadrupole mass spectrometer with z-spray electrospray ionization. Spectra were scanned from 120–1000 amu over 2 seconds. ELSD (Evaporative Light Scattering Detector) data was also acquired as an analog channel. Gradient elution was used with Buffer A as 2% acetonitrile in water with 0.02% TFA and Buffer B as 2% water in Acetonitrile with 0.02% TEA at 1.5 mL/min. Samples were eluted as follows: 90% A for 0.5 minutes ramped to 95% B over 3.5 minutes and held at 95% B for 0.5 minutes and then the column is brought back to initial conditions over 0.1 minutes. Total run time is 4.8 minutes.
**comm means commercially available.

Using the above described methods, and substituting the appropriate starting materials, other formula (Ia) and formula (Ib) compounds, such as those shown in Tables 5 and 6 below, may be prepared.

TABLE 5

(Ia)

| Example | X | NR¹R¹ | R² | R³ | R⁴ | Ring B (Points of fusion of Ring B to Ia are designated by the symbol •) |
|---|---|---|---|---|---|---|
| 168 | O | NH$_2$ | Ph | H | H | 4H-pyran-4-one |
| 169 | O | NH$_2$ | 2,4-diCl—Ph | H | H | dihydropyranone |
| 170 | O | NH$_2$ | 2-naphthyl | H | H | dihydropyran |
| 171 | S | NH$_2$ | 2-naphthyl | H | H | dihydropyran |
| 172 | O | N[C(O)Me]$_2$ | 2,4-diCl—Ph | OH | H | dihydropyran |
| 173 | O | NH[C(O)Me] | 2,4-diCl—Ph | H | H | dihydropyran |
| 174 | O | NH[C(O)Ph] | 2,4-diCl—Ph | H | H | dihydropyran |
| 175 | O | N(n-Pr)$_2$ | 2,4-diCl—Ph | H | H | dihydropyran |

TABLE 5-continued
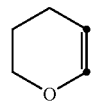
(Ia)
| Example | X | NR¹R¹ | R² | R³ | R⁴ | Ring B (Points of fusion of Ring B to Ia are designated by the symbol •) |
|---|---|---|---|---|---|---|
| 176 | O | NHEt | 2,4,6-trCl—Ph | H | H | 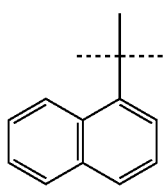 |
| 177 | O | NH₂ | 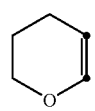 | H | H | 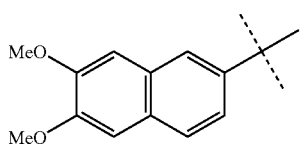 |
| 178 | O | NH₂ | 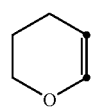 | H | H | 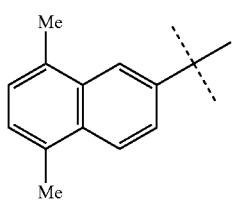 |
| 179 | O | NH₂ | 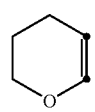 | H | H | 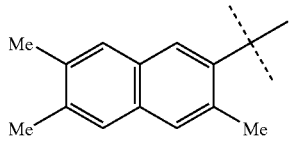 |
| 180 | S | NH₂ | 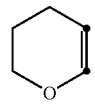 | H | OH | 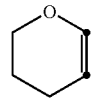 |
| 181 | O | NH₂ | 4-Cl—Ph- | H | H | 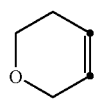 |
| 182 | O | NH₂ | 3-NO₂Ph— | H | H | 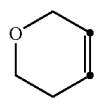 |
| 183 | O | NH₂ | 4-CN—Ph— | H | H | |

TABLE 5-continued (Ia)

| Example | X | NR¹R¹ | R² | R³ | R⁴ | Ring B (Points of fusion of Ring B to Ia are designated by the symbol •) |
|---|---|---|---|---|---|---|
| 184 | O | NH₂ | 2,4,6-triCl—Ph— | H | H | tetrahydrothiopyran-4-one (S, C=O) |
| 185 | O | NH₂ | 3,4,5-triMe—Ph | H | H | pyrimidine |
| 186 | O | NH₂ | 4-CF₃—Ph— | H | H | pyrimidine |
| 187 | O | NH₂ | 3-CH₃CO—Ph | H | H | pyridine |
| 188 | O | NH₂ | 4-(COOH)—Ph— | H | H | pyridine |
| 189 | O | NH₂ | 3-(CO₂Et)—Ph— | H | H | oxazole |
| 190 | O | NH₂ | 4-[CON(Me)₂]—Ph | H | H | thiazole |
| 191 | O | NH₂ | 3-(NHCH₂CH₂SO₂Me)—Ph | H | H | imidazole |
| 192 | O | NH₂ | 4-(NHSO₂Me)—Ph | H | H | N-Me-imidazole |
| 193 | O | NH₂ | 3-(NHCOEt)—Ph | H | H | N-Me-imidazole |

TABLE 5-continued (Ia)

| Example | X | NR¹R¹ | R² | R³ | R⁴ | Ring B (Points of fusion of Ring B to Ia are designated by the symbol •) |
|---|---|---|---|---|---|---|
| 194 | O | NH₂ | 4-(NH—(CH₂)₄—COMe)—Ph | H | H | pyridine |
| 195 | O | NH₂ | 3-pyridyl | H | H | pyridine |
| 196 | O | NH₂ | 5-pyrimidinyl | H | H | dihydrothiopyran |
| 197 | O | NH₂ | 1,2,4-triazin-3-yl | H | H | dihydrofuran |
| 198 | O | NH₂ | 3-pyridazinyl | H | H | dihydrofuran |
| 199 | O | NH₂ | 2-pyrimidinyl | H | H | dihydrofuran |
| 200 | O | NH₂ | 1,2,4-triazin-3-yl | H | H | 3,4-dimethylfuran |
| 201 | O | NH₂ | 6-hydroxypyridin-3-yl | H | H | N-methyl-tetrahydropyridine |
| 202 | O | NH₂ | 6-nitropyridin-3-yl | H | H | N-methyl-dihydropyridinone |
| 203 | O | NH₂ | 6-chloropyridin-3-yl | H | H | cyclopentene |

TABLE 5-continued (Ia)

| Example | X | NR¹R¹ | R² | R³ | R⁴ | Ring B (Points of fusion of Ring B to Ia are designated by the symbol •) |
|---|---|---|---|---|---|---|
| 204 | O | NH₂ | 2-MeO-5-(t-Bu)-pyridin-5-yl (MeO-pyridine with t-Bu attachment) | H | OH | cyclopentene |
| 205 | O | NH₂ | 2-Cl-4-Me-5-(t-Bu)-pyridine | OH | H | cyclopentene |
| 206 | S | NH₂ | 2-Me-4-(CO₂CH₂CH₂NH₂)-5-(t-Bu)-pyridine | F | H | cyclopentene |
| 207 | O | NH₂ | 2-Me-4-(CO₂Me)-5-(t-Bu)-pyridine | F | H | cyclopentene |
| 208 | O | NH₂ | 6-C(O)CH₃-pyridin-3-yl with t-Bu | Cl | H | cyclopentene |
| 209 | O | NH₂ | 6-C(O)N(CH₃)₂-pyridin-3-yl with t-Bu | F | H | cyclopentene |
| 210 | O | NH₂ | 6-N(Et)₂-pyridin-3-yl with t-Bu | OH | H | cyclohexene |

TABLE 5-continued
(Ia)
| Example | X | NR¹R¹ | R² | R³ | R⁴ | Ring B (Points of fusion of Ring B to Ia are designated by the symbol •) |
|---|---|---|---|---|---|---|
| 211 | O | NH₂ | 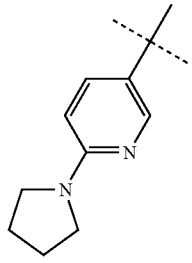 | H | Cl |  |
| 212 | O | NH₂ | 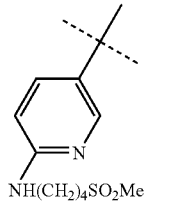 NH(CH₂)₄SO₂Me | H | F |  |
| 213 | S | NH₂ | 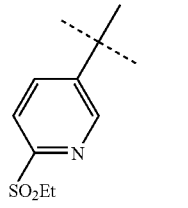 SO₂Et | F | H |  |
| 214 | S | NH₂ | 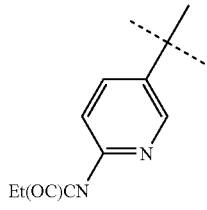 Et(OC)CN | Cl | H |  |
| 215 | S | NH₂ | 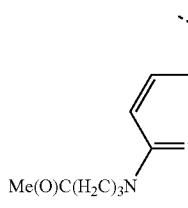 Me(O)C(H₂C)₃N | H | Cl | |

TABLE 5-continued
(Ia)
| Example | X | NR¹R¹ | R² | R³ | R⁴ | Ring B (Points of fusion of Ring B to Ia are designated by the symbol •) |
|---|---|---|---|---|---|---|
| 216 | S | $NH_2$ |  | F | H |  |
| 217 | S | $NH_2$ |  | H | F |  |
| 218 | O | $NH_2$ |  | H | Cl |  |
| 219 | O | $NH_2$ |  | $CF_3$ | H |  |
| 220 | O | $NH_2$ |  | $OCF_3$ | H |  |
| 221 | O | $NH_2$ |  | $CH_3$ | H |  |
| 222 | O | $NH_2$ | | H | F |  |

TABLE 5-continued
(Ia)
| Example | X | NR¹R¹ | R² | R³ | R⁴ | Ring B (Points of fusion of Ring B to Ia are designated by the symbol •) |
|---|---|---|---|---|---|---|
| 223 | O | NH₂ |  | H | Cl |  |
| 224 | O | NH₂ |  | H | OH |  |
| 225 | O | NH₂ |  | H | H |  |
| 226 | O | NH₂ |  | H | Cl |  |
| 227 | O | NH₂ |  | H | OH |  |
| 228 | O | NH₂ |  | H | F |  |
| 229 | O | NH₂ |  | OH | H |  |

TABLE 5-continued (Ia)

| Example | X | NR¹R¹ | R² | R³ | R⁴ | Ring B (Points of fusion of Ring B to Ia are designated by the symbol •) |
|---|---|---|---|---|---|---|
| 230 | O | NH₂ | (Et)₂N-substituted tert-butyl-thiophene | H | F | cyclohexene |
| 231 | O | NH₂ | HO-(CH₂)₃-NH-substituted tert-butyl-thiophene | H | H | cyclohexene |
| 232 | O | NH₂ | MeO₂S-NH-substituted tert-butyl-thiophene | H | F | dihydropyran |
| 233 | O | NH₂ | MeC(O)CH₂-NH-substituted tert-butyl-furan | F | H | dihydropyran |
| 234 | S | NH₂ | Me-, Me-substituted tert-butyl-thieno[2,3-b]pyridine | Cl | H | dihydropyran |
| 235 | S | NH₂ | trimethyl-substituted tert-butyl-quinoline | OCH₃ | H | dihydropyran |
| 236 | S | NH₂ | trimethyl-substituted tert-butyl-naphthyridine | H | H | dihydropyran |

TABLE 5-continued (Ia)

| Example | X | NR¹R¹ | R² | R³ | R⁴ | Ring B (Points of fusion of Ring B to Ia are designated by the symbol •) |
|---|---|---|---|---|---|---|
| 237 | S | NH₂ | 2,6-dimethyl-pyrido[2,3-b]pyrazin-3-yl | H | H | dihydropyran |
| 238 | O | NHEt | quinolin-3-yl | F | H | dihydropyran |
| 239 | O | N(Me)₂ | 2-piperidin-1-yl-quinolin-3-yl | OCF₃ | H | dihydropyran |
| 240 | O | NH₂ | 5,8-bis(ethoxycarbonyl)-2-hydroxyquinolin-3-yl | F | H | dihydropyran |
| 241 | O | NH₂ | 3-methyl-isoxazolo[5,4-b]pyridin-5-yl | Cl | H | dihydropyran |
| 242 | O | NH₂ | 3-(dimethylaminocarbonyl)-isothiazolo[5,4-b]pyridin-5-yl | H | H | dihydropyran |
| 243 | O | NH₂ | 2-trifluoromethyl-quinolin-3-yl | H | H | dihydropyran |

TABLE 5-continued (Ia)

| Example | X | NR¹R¹ | R² | R³ | R⁴ | Ring B (Points of fusion of Ring B to Ia are designated by the symbol •) |
|---|---|---|---|---|---|---|
| 244 | O | NH₂ | 3-(2-amino-1,8-naphthyridin-3-yl) | OH | H | tetrahydropyran |
| 245 | O | NH₂ | 2-chloro-6,7-dimethoxyquinolin-3-yl | H | H | cyclohexene |
| 246 | O | NH₂ | 7-acetylquinoxalin-6-yl | H | H | cyclohexene |
| 247 | O | NH₂ | 6-(acetamidomethyl)oxazolo[4,5-b]pyridin-5-yl | H | H | cyclohexene |
| 248 | O | NH₂ | 2-(N,N-dimethylcarbamoyl)quinolin-3-yl | H | H | cyclohexene |
| 249 | O | NH₂ | 2-(N,N-diethylamino)quinolin-3-yl | H | H | cyclohexene |
| 250 | O | NH₂ | 6-(ethylsulfonylmethylamino)oxazolo[4,5-b]pyridin-5-yl | H | H | cyclohexene |

TABLE 5-continued (Ia)

| Example | X | NR¹R¹ | R² | R³ | R⁴ | Ring B (Points of fusion of Ring B to Ia are designated by the symbol •) |
|---------|---|-------|-----|----|----|-----|
| 251 | O | NH₂ | 3-tert-butyl-6-(trifluoromethylsulfonyl)benzothiophene | H | H | cyclohexanone |
| 252 | O | NH₂ | 7-tert-butyl-N-(2-oxopropyl)quinoline-3-carboxamide | H | H | cyclohexanone |
| 253 | O | NH₂ | 3-tert-butyl-3,4-dihydro-2H-pyrano[2,3-b]pyridine | H | H | cyclohexanone |
| 254 | O | NH₂ | 3-tert-butyl-7,8-dihydro-5H-pyrano[4,3-b]pyridine | H | H | cyclohexanone |
| 255 | O | NH₂ | 1-tert-butyl-3-(trifluoromethyl)benzene | H | H | cyclohexanone |
| 256 | O | NH₂ | 3-(2-(dimethylamino)ethyl)-1-tert-butylbenzene | H | H | cyclohexanone |
| 257 | O | NH₂ | 1-tert-butyl-3-((methylsulfinyl)methyl)benzene | H | H | cyclohexanone |

TABLE 5-continued (Ia)

| Example | X | NR¹R¹ | R² | R³ | R⁴ | Ring B (Points of fusion of Ring B to Ia are designated by the symbol •) |
|---|---|---|---|---|---|---|
| 258 | O | NH₂ | 3-(tBu)-C₆H₄-CH₂-N(CH₃)(CH₂CH₂OMe) | H | H | cyclohexanone |
| 259 | O | NH₂ | 3-(tBu)-C₆H₄-SO₂-N(CH₃)(C(O)CH₃) | H | H | cyclohexanone |
| 260 | S | NH₂ | 3-(tBu)-C₆H₄-CH₂-C(O)-cyclopropyl | H | H | cyclohexanone |
| 261 | O | NH₂ | 3-(tBu)-C₆H₄-CH₂-N(propyl)(CH₂CH₂OMe) with N=NH guanidine | H | H | cyclohexanone |
| 262 | O | NHMe | 3-(MeO)-C₆H₄-C(CH₃)₂- | H | H | cyclohexanone |

TABLE 6

(Ib)

| Example | X | NR¹R¹ | R² | R³ | R⁴ | Ring B (Points of fusion of Ring B to Ib are designated by the symbol •) |
|---|---|---|---|---|---|---|
| 263 | O | NH$_2$ | Ph | H | H | dihydropyranone |
| 264 | O | NH$_2$ | 2,4-diCl—Ph | H | H | dihydropyranone |
| 265 | O | NH$_2$ | naphthyl | H | H | dihydropyran |
| 266 | S | NH$_2$ | naphthyl | H | H | dihydropyran |
| 267 | O | N[C(O)Me]$_2$ | 2,4-diCl—Ph | OH | H | dihydropyran |
| 268 | O | NH[C(O)Me] | 2,4-diCl—Ph | H | H | dihydropyran |
| 269 | O | NH[C(O)Ph] | 2,4-diCl—Ph | H | H | dihydropyran |
| 270 | O | N(n-Pr)$_2$ | 2,4-diCl—Ph | H | H | dihydropyran |
| 271 | O | NHEt | 2,4,6-trCl—Ph | H | H | dihydropyran |

TABLE 6-continued (Ib)

| Example | X | NR¹R¹ | R² | R³ | R⁴ | Ring B (Points of fusion of Ring B to Ib are designated by the symbol •) |
|---|---|---|---|---|---|---|
| 272 | O | NH₂ | 1-naphthyl | H | H | dihydropyran |
| 273 | O | NH₂ | 6,7-dimethoxy-2-naphthyl | H | H | dihydropyran |
| 274 | O | NH₂ | 5,8-dimethyl-2-naphthyl | H | H | dihydropyran |
| 275 | S | NH₂ | 3,6,7-trimethyl-2-naphthyl | H | OH | dihydropyran |
| 276 | O | NH₂ | 4-Cl—Ph— | H | H | dihydropyran |
| 277 | O | NH₂ | 3-NO₂Ph— | H | H | dihydropyran |
| 278 | O | NH₂ | 4-CN—Ph— | H | H | dihydropyran |
| 279 | O | NH₂ | 2,4,6-triCl—Ph— | H | H | dihydrothiopyranone |

TABLE 6-continued (Ib)

| Example | X | NR¹R¹ | R² | R³ | R⁴ | Ring B (Points of fusion of Ring B to Ib are designated by the symbol •) |
|---|---|---|---|---|---|---|
| 280 | O | NH₂ | 3,4,5-triMe—Ph | H | H | pyrimidine |
| 281 | O | NH₂ | 4-CF₃—Ph— | H | H | pyrimidine |
| 282 | O | NH₂ | 3-CH₃CO—Ph | H | H | pyridine |
| 283 | O | NH₂ | 4-(COOH)—Ph— | H | H | pyridine |
| 284 | O | NH₂ | 3-(CO₂Et)—Ph— | H | H | oxazole |
| 285 | O | NH₂ | 4-[CON(Me)₂]—Ph | H | H | thiazole |
| 286 | O | NH₂ | 3-(NHCH₂CH₂SO₂Me)—Ph | H | H | imidazole |
| 287 | O | NH₂ | 4-(NHSO₂Me)—Ph | H | H | N-Me imidazole |
| 288 | O | NH₂ | 3-(NHCOEt)—Ph | H | H | N,N-diMe imidazole |
| 289 | O | NH₂ | (4-NH—(CH₂)₄—COMe)—Ph | H | H | pyridine |

TABLE 6-continued
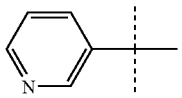
(Ib)
| Example | X | NR¹R¹ | R² | R³ | R⁴ | Ring B (Points of fusion of Ring B to Ib are designated by the symbol •) |
|---|---|---|---|---|---|---|
| 290 | O | $NH_2$ |  | H | H | 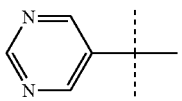 |
| 291 | O | $NH_2$ |  | H | H | 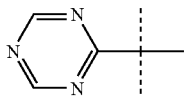 |
| 292 | O | $NH_2$ |  | H | H | 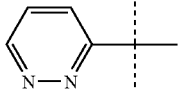 |
| 293 | O | $NH_2$ |  | H | H | 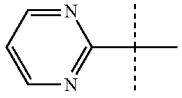 |
| 294 | O | $NH_2$ |  | H | H | 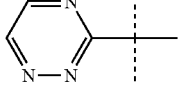 |
| 295 | O | $NH_2$ | 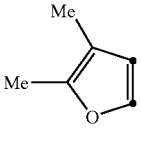 | H | H | 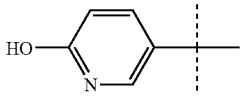 |
| 296 | O | $NH_2$ | 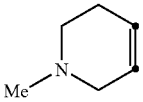 | H | H | 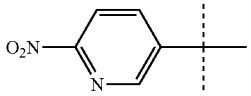 |
| 297 | O | $NH_2$ | 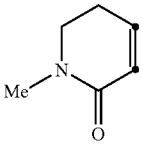 | H | H | 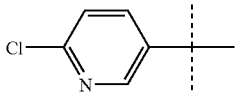 |
| 298 | O | $NH_2$ |  | H | H | 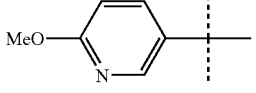 |
| 299 | O | $NH_2$ |  | H | OH | |

TABLE 6-continued (Ib)

| Example | X | NR¹R¹ | R² | R³ | R⁴ | Ring B (Points of fusion of Ring B to Ib are designated by the symbol •) |
|---------|---|-------|-----|-----|-----|-----|
| 300 | O | $NH_2$ | 4-Me, 2-Cl pyridine with t-Bu | OH | H | cyclopentene |
| 301 | S | $NH_2$ | 2-Me pyridine, 4-$CO_2CH_2CH_2NH_2$, 5-t-Bu | F | H | cyclopentene |
| 302 | O | $NH_2$ | 2-Me pyridine, 4-$CO_2Me$, 5-t-Bu | F | H | cyclopentene |
| 303 | O | $NH_2$ | 5-t-Bu, 2-C(O)CH₃ pyridine | Cl | H | cyclopentene |
| 304 | O | $NH_2$ | 5-t-Bu, 2-C(O)N(CH₃)₂ pyridine | F | H | cyclopentene |
| 305 | O | $NH_2$ | 5-t-Bu, 2-N(Et)₂ pyridine | OH | H | cyclohexene |

TABLE 6-continued
(Ib)
| Example | X | NR¹R¹ | R² | R³ | R⁴ | Ring B (Points of fusion of Ring B to Ib are designated by the symbol •) |
|---|---|---|---|---|---|---|
| 306 | O | NH₂ | 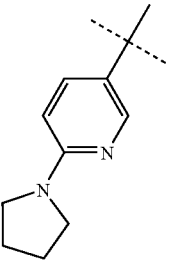 | H | Cl |  |
| 307 | O | NH₂ |  NH(CH₂)₄SO₂Me | H | F |  |
| 308 | S | NH₂ | 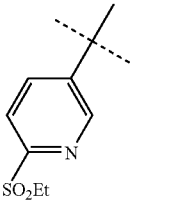 SO₂Et | F | H |  |
| 309 | S | NH₂ |  Et(OC)CN | Cl | H |  |
| 310 | S | NH₂ | 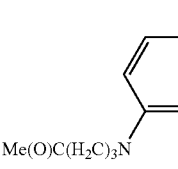 Me(O)C(H₂C)₃N | H | Cl | |

TABLE 6-continued (Ib)

| Example | X | NR¹R¹ | R² | R³ | R⁴ | Ring B (Points of fusion of Ring B to Ib are designated by the symbol •) |
|---------|---|-------|-----|-----|-----|-----|
| 311 | S | NH₂ | 3-isoxazolyl | F | H | cyclohexene |
| 312 | S | NH₂ | 4-thiazolyl | H | F | cyclohexene |
| 313 | O | NH₂ | 4-oxazolyl | H | Cl | cyclohexene |
| 314 | O | NH₂ | 1-Me-imidazol-4-yl | CF₃ | H | cyclohexene |
| 315 | O | NH₂ | 4-oxazolyl | OCF₃ | H | cyclohexene |
| 316 | O | NH₂ | 1-Me-1,2,4-triazol-3-yl | CH₃ | H | cyclohexene |
| 317 | O | NH₂ | 1,2,3-thiadiazol-4-yl | H | F | cyclohexene |

TABLE 6-continued (Ib)

| Example | X | NR¹R¹ | R² | R³ | R⁴ | Ring B (Points of fusion of Ring B to Ib are designated by the symbol •) |
|---------|---|-------|-----|-----|-----|-----|
| 318 | O | NH₂ | 3-thienyl | H | Cl | cyclohexenyl |
| 319 | O | NH₂ | 2,5-dimethyl-4-methylfuran-3-yl | H | OH | cyclohexenyl |
| 320 | O | NH₂ | 2,5-dichloro-4-methylthien-3-yl | H | H | cyclohexenyl |
| 321 | O | NH₂ | 2-(2-methoxyethoxycarbonyl)furan-3-yl | H | Cl | cyclohexenyl |
| 322 | O | NH₂ | 2,5-bis(methoxycarbonyl)furan-3-yl | H | OH | cyclohexenyl |
| 323 | O | NH₂ | 5-acetylfuran-3-yl | H | F | cyclohexenyl |
| 324 | O | NH₂ | 5-(N,N-dimethylcarbamoyl)thien-3-yl | OH | H | cyclohexenyl |

TABLE 6-continued (Ib)

| Example | X | NR¹R¹ | R² | R³ | R⁴ | Ring B (Points of fusion of Ring B to Ib are designated by the symbol • |
|---------|---|-------|-----|-----|-----|------|
| 325 | O | NH₂ | (Et)₂N-substituted thiophene | H | F | cyclohexene |
| 326 | O | NH₂ | HO(CH₂)₃NH-substituted thiophene | H | H | cyclohexene |
| 327 | O | NH₂ | MeO₂S-NH-substituted thiophene | H | F | dihydropyran |
| 328 | O | NH₂ | Me-C(O)-CH₂-NH-substituted furan | F | H | dihydropyran |
| 329 | S | NH₂ | dimethyl-thienopyridine | Cl | H | dihydropyran |
| 330 | S | NH₂ | tetramethylquinoline | OCH₃ | H | dihydropyran |
| 331 | S | NH₂ | tetramethylnaphthyridine | H | H | dihydropyran |

TABLE 6-continued
(Ib)
| Example | X | NR¹R¹ | R² | R³ | R⁴ | Ring B (Points of fusion of Ring B to Ib are designated by the symbol •) |
|---|---|---|---|---|---|---|
| 332 | S | NH₂ | 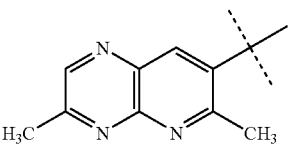 | H | H |  |
| 333 | O | NHEt | 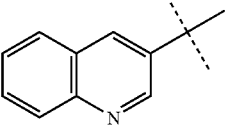 | F | H |  |
| 334 | O | N(Me)₂ | 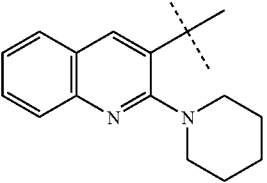 | OCF₃ | H |  |
| 335 | O | NH₂ | 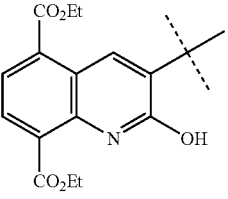 | F | H |  |
| 336 | O | NH₂ | 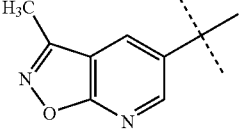 | Cl | H |  |
| 337 | O | NH₂ | 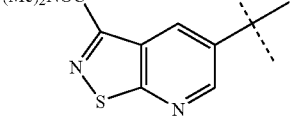 | H | H |  |
| 338 | O | NH₂ | 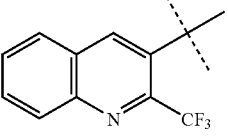 | H | H |  |

TABLE 6-continued (Ib)

| Example | X | NR¹R¹ | R² | R³ | R⁴ | Ring B (Points of fusion of Ring B to Ib are designated by the symbol •) |
|---------|---|-------|-----|-----|-----|---|
| 339 | O | $NH_2$ | (1,8-naphthyridin-3-yl with 2-NH₂) | OH | H | tetrahydropyran |
| 340 | O | $NH_2$ | (6,7-dimethoxy-2-chloroquinolin-3-yl) | H | H | cyclohexene |
| 341 | O | $NH_2$ | (quinoxalin-6-yl with 7-C(O)Me) | H | H | cyclohexene |
| 342 | O | $NH_2$ | (oxazolo[4,5-b]pyridin-5-yl with 6-NHC(O)Me) | H | H | cyclohexene |
| 343 | O | $NH_2$ | (quinolin-3-yl with 2-CON(Me)₂) | H | H | cyclohexene |
| 344 | O | $NH_2$ | (quinolin-3-yl with 2-N(Et)CH₃) | H | H | cyclohexene |
| 345 | O | $NH_2$ | (oxazolo[4,5-f]benzo with NHCH₂SO₂Et) | H | H | tetrahydropyran |

TABLE 6-continued (Ib)

| Example | X | NR¹R¹ | R² | R³ | R⁴ | Ring B (Points of fusion of Ring B to Ib are designated by the symbol •) |
|---|---|---|---|---|---|---|
| 346 | O | NH₂ | F₃C—O₂S- substituted benzothiophene with t-Bu | H | H | cyclohexanone |
| 347 | O | NH₂ | Me-C(O)-CH₂-NH-C(O)- quinoline | H | H | cyclohexanone |
| 348 | O | NH₂ | chromeno-pyridine | H | H | cyclohexanone |
| 349 | O | NH₂ | pyrano-pyridine | H | H | cyclohexanone |
| 350 | O | NH₂ | F₃C-phenyl | H | H | cyclohexanone |
| 351 | O | NH₂ | (Me)₂N-CH₂CH₂-phenyl | H | H | cyclohexanone |
| 352 | O | NH₂ | H₃C-S(O)-CH₂-phenyl | H | H | cyclohexanone |

TABLE 6-continued

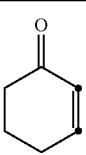

(Ib)

| Example | X | NR¹R¹ | R² | R³ | R⁴ | Ring B (Points of fusion of Ring B to Ib are designated by the symbol •) |
|---|---|---|---|---|---|---|
| 353 | O | $NH_2$ | 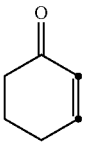 | H | H | 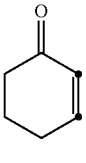 |
| 354 | O | $NH_2$ | | H | H | |
| 355 | S | $NH_2$ | | H | H | |
| 356 | O | $NH_2$ | | H | H | |
| 357 | O | NHMe | | H | H | |

Compositions Useful for the Method of this Invention

The term "Formula I" means, severally and collectively, Formula Ia and Formula Ib.

A compound of Formula I is useful in this method for treating the conditions described further herein when it is formulated as a pharmaceutically acceptable composition. A pharmaceutically acceptable composition is a compound of Formula I in admixture with a pharmaceutically acceptable carrier. A pharmaceutically acceptable carrier is any carrier that is relatively non-toxic and innocuous to a patient at concentrations consistent with effective activity of the active ingredient so that any side effects ascribable to the carrier do not vitiate the beneficial effects of the active ingredient.

Commonly used pharmaceutical ingredients which can be used as appropriate to formulate the composition for its intended route of administration include:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include but are not limited to powdered cellulose and activated charcoal);

aerosol propellants (examples include but are not limited to carbon dioxide, $CCl_2F_2$, $F_2ClC$—$CClF_2$ and $CClF_3$);

air displacement agents (examples include but are not limited to nitrogen and argon);

antifungal preservatives (examples include but are not limited to benzoic acid, butylparaben, ethylparaben, methylparaben, propylparaben, sodium benzoate);

antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate dihydrate);

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection);

chelating agents (examples include but are not limited to edetate disodium and edetic acid);

colorants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include but are not limited to bentonite);

emulsifying agents (examples include but are not limited to acacia, cetomacrogol, cetyl alcohol, glyceryl monostearate, lecithin, sorbitan monooleate, polyoxyethylene 50 monostearate);

encapsulating agents (examples include but are not limited to gelatin and cellulose acetate phthalate);

flavorants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin);

oils (examples include but are not limited to arachis oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas);

plasticizers (examples include but are not limited to diethyl phthalate and glycerol);

solvents (examples include but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (mixtures);

surfactants (examples include but are not limited to benzalkonium chloride, nonoxynol 10, oxtoxynol 9, polysorbate 80, sodium lauryl sulfate and sorbitan mono-palmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);

tablet anti-adherents (examples include but are not limited to magnesium stearate and talc);

tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include but are not limited to dibasic calcium phosphate);

tablet disintegrants (examples include but are not limited to alginic acid, carboxymethylcellulose calcium, microcrystalline cellulose, polacrillin potassium, cross-linked polyvinylpyrrolidone, sodium alginate, sodium starch glycollate and starch);

tablet glidants (examples include but are not limited to colloidal silica, corn starch and talc);

tablet lubricants (examples include but are not limited to calcium stearate, magnesium stearate, mineral oil, stearic acid and zinc stearate);

tablet/capsule opaquants (examples include but are not limited to titanium dioxide);

tablet polishing agents (examples include but are not limited to carnuba wax and white wax);

thickening agents (examples include but are not limited to beeswax, cetyl alcohol and paraffin);

tonicity agents (examples include but are not limited to dextrose and sodium chloride);

viscosity increasing agents (examples include but are not limited to alginic acid, bentonite, carbomers, carboxymethylcellulose sodium, methylcellulose, polyvinyl pyrrolidone, sodium alginate and tragacanth); and wetting agents (examples include but are not limited to heptadecaethylene oxycetanol, lecithins, sorbitol monooleate, polyoxyethylene sorbitol monooleate, and polyoxyethylene stearate).

The compounds of the present invention can be administered with pharmaceutically-acceptable carriers well known in the art using any effective conventional dosage unit forms formulated as immediate, slow or timed release preparations, including, for example, the following.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule which can be of the ordinary hard- or soft-shelled gelatin type containing, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatin, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, coloring agents, and flavoring agents such as peppermint, oil of wintergreen, or cherry flavoring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavoring and coloring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more coloring agents; one or more flavoring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavoring and coloring agents.

The compounds of this invention may also be administered parenterally, that is, subcutaneously, intravenously, intraocularly, intrasynovially, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulation ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such material are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, issued Jun. 11, 1991, incorporated herein by reference). Such patches may be constructed for continuous, pulsatile, or on demand delivery of pharmaceutical agents.

Controlled release formulations for parenteral administration include liposomal, polymeric microsphere and polymeric gel formulations which are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized. Such ingredients and procedures include those described in the following references, each of which is incorporated herein by reference: Powell, M. F. et al., "Compendium of Excipients for Parenteral Formulations" *PDA Journal of Pharmaceutical Science & Technology* 1998, 52(5), 238–311; Strickley, R. G "Parenteral Formulations of Small Molecule Therapeutics Marketed in the United States (1999)-Part-1" *PDA Journal of Pharmaceutical Science & Technology* 1999, 53(6), 324–349; and Nema, S. et al, "Excipients and Their Use in Injectable Products" *PDA Journal of Pharmaceutical Science & Technology* 1997, 51(4), 166–171.

It is believed that one skilled in the art, utilizing the preceding information, can utilize the present invention to its fullest extent. Nevertheless, the following are examples of pharmaceutical formulations that can be used in the method of the present invention. They are for illustrative purposes only, and are not to be construed as limiting the invention in any way.

Pharmaceutical compositions according to the present invention can be further illustrated as follows:

Sterile IV Solution: A 5 mg/mL solution of the desired compound of this invention is made using sterile, injectable water, and the pH is adjusted if necessary. The solution is diluted for administration to 1–2 mg/mL with sterile 5% dextrose and is administered as an IV infusion over 60 min.

Lyophilized powder for IV administration: A sterile preparation can be prepared with (i) 100–1000 mg of the desired compound of this invention as a lypholized powder, (ii) 32–327 mg/mL sodium citrate, and (iii) 300–3000 mg Dextran 40. The formulation is reconstituted with sterile, injectable saline or dextrose 5% to a concentration of 10 to 20 mg/mL, which is further diluted with saline or dextrose 5% to 0.2–0.4 mg/mL, and is administered either IV bolus or by IV infusion over 15–60 min.

Intramuscular suspension: The following solution or suspension can be prepared, for intramuscular injection:
  50 mg/mL of the desired, water-insoluble compound of this invention
  5 mg/mL sodium carboxymethylcellulose
  4 mg/mL TWEEN 80
  9 mg/mL sodium chloride
  9 mg/mL benzyl alcohol Hard Shell Capsules: A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules: A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets: A large number of tablets are prepared by conventional procedures so that the dosage unit was 100 mg of active ingredient, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules: These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Method of Treating Cancer

The compounds and compositions described herein can be used to treat or prevent hyper-proliferative disorders. An effective amount of a compound or composition of this invention can be administered to a patient in need thereof in order to achieve a desired pharmacological effect. A patient, for the purpose of this invention, is a mammal, including a human, in need of treatment (including prophylactic treatment) for a particular disorder described further herein. A pharmaceutically effective amount of compound or composition is that amount which produces a desired result or exerts an influence on the particular hyper-proliferative disorder being treated.

Hyper-proliferative disorders include but are not limited to solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumor.

Tumors of the male reproductive organs include, but are not limited to prostate and testicular cancer. Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallbladder, gastric, pancreatic, rectal, small-intestine, and salivary gland cancers.

Tumors of the urinary tract include, but are not limited to bladder, penile, kidney, renal pelvis, ureter, and urethral cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal/hypopharyngeal/nasopharyngeal/oropharyngeal cancer, and lip and oral cavity cancer.

Lymphomas include, but are not limited to AIDS-related lymphoma, non-Hodgkin's lymphoma, cutaneous T-cell lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

The disorders described above have been well characterized in humans, but also exist with a similar etiology in other mammals. Accordingly, the method of this invention can be administered to mammals, including humans, in need thereof for the treatment of angiogenesis and/or proliferative dependent disorders.

The utility of the compounds of the present invention can be illustrated, for example, by their activity in vitro in the in vitro tumor cell proliferation assay described below. The link between activity in tumor cell proliferation assays in vitro and anti-tumor activity in the clinical setting has been very well established in the art. For example, the therapeutic utility of taxol (Silvestrini et al. *Stem Cells* 1993, 11(6), 528–35), taxotere (Bissery et al. *Anti Cancer Drugs* 1995, 6(3), 339), and topoisomerase inhibitors (Edelman et al. *Cancer Chemother. Pharmacol.* 1996, 37(5), 385–93) were demonstrated with the use of in vitro tumor proliferation assays.

The compounds and compositions described herein, including salts and esters thereof, exhibit anti-proliferative activity and are thus useful to prevent or treat the disorders associated with hyper-proliferation. The following assay is one of the methods by which compound activity relating to treatment of the disorders identified herein can be determined.

In Vitro Tumor Cell Proliferation Assay

The adherent tumor cell proliferation assay used to test the compounds of the present invention involves a readout called Cell Titre-Glo developed by Promega (Cunningham, B A "A Growing Issue: Cell Proliferation Assays. Modern kits ease quantification of cell growth" *The Scientist* 2001, 15(13), 26, and Crouch, S P et al., "The use of ATP bioluminescence as a measure of cell proliferation and cytotoxicity" *Journal of Immunological Methods* 1993, 160, 81–88).

H460 cells (lung carcinoma, purchased from ATCC) are plated in 96-well plates at 3000 cells/well in complete media with 10% Fetal Calf Serum and incubated 24 hours at 37° C. Twenty-four hours after plating, test compounds are added over a final concentration range of 10 nM to 20 µM in serial dilutions at a final DMSO concentration of 0.2%. Cells are incubated for 72 hours at 37° C. in complete growth media after addition of the test compound. On day 4, using a Promega Cell Titer Glo Luminescent® assay kit, the cells are lysed and 100 microliters of substrate/buffer mixture is added to each well, mixed and incubated at room temperature for 8 minutes. The samples are read on a luminometer to measure the amount of ATP present in the cell lysates from each well, which corresponds to the number of viable cells in that well. Values read at 24-hour incubation are subtracted as Day 0. For determination of IC50's, a linear regression analysis can be used to determine drug concentration which results in a 50% inhibition of cell proliferation using this assay format. Compounds of this invention showed a significant inhibition of tumor cell proliferation in this assay.

Based upon the above and other standard laboratory techniques known to evaluate compounds useful for the prevention and/or treatment of the diseases or disorders described above by standard toxicity tests and by standard pharmacological assays for the determination of the prevention and/or treatment of the conditions identified above in mammals, and by comparison of these results with the results of known medicaments that are used to treat these conditions, the effective dosage of the compounds of this invention can readily be determined for prevention and/or treatment of each desired indication. The amount of the active ingredient to be administered in the prevention and/or treatment of one of these conditions can vary widely according to such considerations as the particular compound and dosage unit employed, the mode of administration, the duration of treatment (including prophylactic treatment), the age and sex of the patient treated, and the nature and extent of the condition to be prevented and/or treated.

The total amount of the active ingredient to be administered will generally range from about 0.001 mg/kg to about 300 mg/kg, and preferably from about 0.10 mg/kg to about 150 mg/kg body weight per day. A unit dosage may contain from about 0.5 mg to about 1500 mg of active ingredient, and can be administered one or more times per day. The daily dosage for administration by injection, including intravenous, intramuscular, subcutaneous and parenteral injections, and use of infusion techniques will preferably be from 0.01 to 200 mg/kg of total body weight. The daily rectal dosage regimen will preferably be from 0.01 to 200 mg/kg of total body weight. The daily vaginal dosage regimen will preferably be from 0.01 to 200 mg/kg of total body weight. The daily topical dosage regimen will preferably be from 0.1 to 200 mg administered between one to four times daily. The transdermal concentration will preferably be that required to maintain a daily dose of from 0.01 to 200 mg/kg. The daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of administration and number of doses of a compound or composition of the present invention or a pharmaceutically acceptable salt or ester thereof can be ascertained by those skilled in the art using conventional prevention and/or treatment tests.

The compounds of this invention can be administered as the sole pharmaceutical agent or in combination with one or more other pharmaceutical agents where the combination causes no unacceptable adverse effects. For example, the compounds of this invention can be combined with other anti-hyper-proliferative or other indication agents, and the like, as well as with admixtures and combinations thereof.

For example, optional anti-hyper-proliferative agents which can be added to the composition include but are not limited to compounds listed on the cancer chemotherapy drug regimens in the 11th Edition of the *Merck Index*, (1996), which is hereby incorporated by reference, such as asparaginase, bleomycin, carboplatin, carmustine, chlorambucil, cisplatin, colaspase, cyclophosphamide, cytarabine, dacarbazine, dactinomycin, daunorubicin, doxorubicin (adriamycine), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, and vindesine.

Other anti-hyper-proliferative agents suitable for use with the composition of the invention include but are not limited to those compounds acknowledged to be used in the treatment and/or prevention of neoplastic diseases in *Goodman and Gilman's The Pharmacological Basis of Therapeutics* (Ninth Edition), editor Molinoff et al., publ. by McGraw-Hill, pages 1225–1287, (1996), which is hereby incorporated by reference, such as aminoglutethimide, L-asparaginase, azathioprine, 5-azacytidine cladribine, busulfan, diethylstilbestrol, 2',2'-difluorodeoxycytidine, docetaxel, erythrohydroxynonyladenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-L-aspartate (PALA), plicamycin, semustine, teniposide, testosterone propionate, thiotepa, trimethylmelamine, uridine, and vinorelbine.

Other anti-hyper-proliferative agents suitable for use with the composition of this invention include but are not limited to other anti-cancer agents such as epothilone, irinotecan, raloxifen and topotecan.

It is believed that one skilled in the art, using the preceding information and information available in the art, can utilize the present invention to its fullest extent. It should be apparent to one of ordinary skill in the art that changes and modifications can be made to this invention without departing from the spirit or scope of the invention as it is set forth herein.

What is claimed is:

1. A compound selected from Formula Ia and Formula Ib

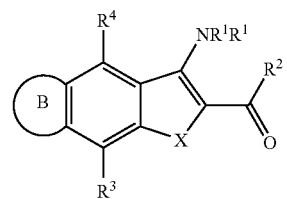

Ia

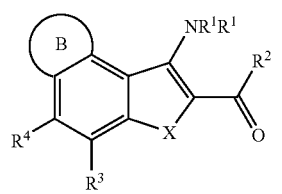

Ib where
  X is O or S;
  $R^1$ is in each instance independently selected from H, $C_1$–$C_6$ alkyl, benzoyl, and $C(O)R^4$;
  $R^4$ is in each instance independently H, ($C_1$–$C_6$)alkoxy, $NR^B R^B$, or ($C_1$–$C_6$)alkyl, said alkyl being optionally substituted with OH, =O, ($C_1$–$C_3$)alkoxy, C(O)$R^B$, halo or $NR^BR^B$;

$R^B$ is in each instance independently H, ($C_3$–$C_6$)cycloalkyl, or ($C_1$–$C_6$)alkyl, said alkyl being optionally substituted with OH, =O, halo, ($C_1$–$C_6$)alkoxy, NH($C_1$–$C_3$)alkyl, N[($C_1$–$C_3$)alkyl]$_2$, NC(O)($C_1$–$C_3$)alkyl or phenyl, and where $R^B$, when it is attached to a N atom, is in each instance ($C_1$–$C_4$)alkyl, then the 2 ($C_1$–$C_4$)alkyl groups, taken together with the N atom to which they are attached, may be joined together to form a saturated ring, and where $R^B$ and $R^B$ together with the N to which they are attached may form a morpholinyl ring or a piperazinyl ring optionally substituted on the available N atom with ($C_1$–$C_6$)alkyl, said alkyl being optionally substituted with OH, =O, NH$_2$, NH($C_1$–$C_3$)alkyl, N[($C_1$–$C_3$)alkyl]$_2$, or ($C_1$–$C_6$)alkoxy, and with the proviso that when $R^B$ is attached to S(O) or to S(O)$_2$, it cannot be H;

$R^2$ is selected from phenyl and naphthyl, each optionally substituted with 1, 2, or 3 substitutents each independently selected from OH, CN, NO$_2$, ($C_1$–$C_6$)alkyl, ($C_1$–$C_6$)alkoxy, ($C_3$–$C_6$)cycloalkyl, halo, halo($C_1$–$C_6$)alkyl, halo ($C_1$–$C_6$)alkoxy, C(O)$R^A$, C(O)$NR^BR^B$, $NR^BR^B$, NH[($C_1$–$C_6$)alkyl]$_{0-1}$S(O)$_2R^B$, NH[($C_1$–$C_6$)alkyl]$_{0-1}$C(O)$R^A$, and NH[($C_1$–$C_6$)alkyl]$_{0-1}$C(O)$OR^B$, a heterocycle selected from a six membered heterocycle, a five membered heterocycle and a fused bicyclic heterocycle, each heterocycle being optionally substituted with 1, 2 or 3 substitutents each independently selected from OH, CN, NO$_2$, ($C_1$–$C_6$)alkyl, ($C_3$–$C_6$)cycloalkyl, ($C_1$–$C_6$)alkoxy, halo, halo($C_1$–$C_6$)alkyl, halo ($C_1$–$C_6$)alkoxy, C(O)$R^A$, C(O)$NR^BR^B$, $NR^BR^B$, NH[($C_1$–$C_6$)alkyl]$_{0-1}$S(O)$_2R^B$, NH[($C_1$–$C_6$)alkyl]$_{0-1}$C(O)$R^A$, and NH[($C_1$–$C_6$)alkyl]$_{0-1}$C(O)$OR^B$, $R^3$ and $R^4$ are each independently selected from H, halo, OH, CN, ($C_1$–$C_3$)alkoxy, ($C_1$–$C_3$)alkyl, halo($C_1$–$C_3$) alkoxy and halo($C_1$–$C_3$)alkyl with the proviso that when X in Formula Ib is S, then $R^4$ cannot be ($C_1$–$C_3$) alkyl;

B is a 5 or 6 membered cyclic moiety being optionally substituted with 1 or 2 subsituents each independently selected from =O, OH, N oxide, halo, halo($C_1$–$C_6$) alkyl, halo($C_1$–$C_6$)alkoxy, ($C_1$–$C_6$)alkyl, ($C_1$–$C_3$)alkylphenyl, ($C_1$–$C_6$)alkoxy, C(O)$R^A$, C(O)$OR^B$, C(O)$NR^BR^B$, $NR^BR^B$, NH[($C_1$–$C_6$)alkyl]$_{0-1}$S(O)$_2R^B$, and NH[($C_1$–$C_6$)alkyl]$_{0-1}$C(O)$R^A$;

or a pharmaceutically acceptable salt or ester thereof.

2. A compound of claim 1 comprising a compound of Formula Ia.

3. A compound of claim 1 comprising a compound of Formula Ib.

4. A compound of claim 2 where $R^2$ is selected from phenyl, a six membered heterocycle and a 5 membered heterocycle, each being optionally substituted.

5. A compound of claim 2 where at least one $R^1$ is H.

6. A compound of claim 2 where B is selected from a ring having all C atoms and a ring having one heteroatom, each being optionally substituted.

7. A compound of claim 2 where $R^2$ is selected from phenyl, a six membered heterocycle and a 5 membered heterocycle, each being optionally substituted, and B is selected from a ring having all C atoms and a ring having one heteroatom, each being optionally substituted.

8. A compound of claim 6 where $R^2$ is optionally substituted with 1 or 2 substituents and $R^3$ and $R^4$ are each independently selected from H, OH, Cl, F, CN, CH$_3$, OCH$_3$, CF$_3$ and OCF$_3$.

9. A compound of claim 7 where optionally substituted B, contains no unsaturation other than the shared double bond which is part of the phenyl ring from which B is fused to.

10. A compound of claim 9 where B is substituted with =O, OH, Cl, F, ($C_1$–$C_6$)alkyl, ($C_1$–$C_6$)alkoxy, $NR^BR^B$, CF$_3$ or OCF$_3$.

11. A compound of claim 3 where $R^2$ is selected from phenyl, a six membered heterocycle and a 5 membered heterocycle, each being optionally substituted.

12. A compound of claim 3 where at least one $R^1$ is H.

13. A compound of claim 3 where B is selected from a ring having all C atoms and a ring having one heteroatom, each being optionally substituted.

14. A compound of claim 3 where $R^2$ is selected from phenyl, a six membered heterocycle and a 5 membered heterocycle, each being optionally substituted, and B is selected from a ring having all C atoms and a ring having one heteroatom, each being optionally substituted.

15. A compound of claim 13 where $R^2$ is optionally substituted with 1 or 2 substituents and $R^3$ and $R^4$ are each independently selected from H, OH, Cl, F, CN, CH$_3$, OCH$_3$, CF$_3$ and OCF$_3$.

16. A compound of claim 14 where optionally substituted B, contains no unsaturation other than the shared double bond which is part of the phenyl ring from which B is fused to.

17. A compound of claim 16 where B is substituted with =O, OH, Cl, F, ($C_1$–$C_6$)alkyl, ($C_1$–$C_6$)alkoxy, $NR^BR^B$, CF$_3$ or OCF$_3$.

18. A composition comprising a compound of Formula Ia or Formula Ib.

19. A composition of claim 18 comprising a compound of Formula Ia.

20. A composition of claim 18 comprising a compound of Formula Ib.

21. A composition of claim 19 where $R^2$ is selected from phenyl, a six membered heterocycle and a 5 membered heterocycle, each being optionally substituted.

22. A composition of claim 21 where at least one $R^1$ is H.

23. A composition of claim 21 where B is selected from a ring having all C atoms and a ring having one heteroatom, each being optionally substituted.

24. A composition of claim 20 where $R^2$ is selected from phenyl, a six membered heterocycle and a 5 membered heterocycle, each being optionally substituted.

25. A composition of claim 24 where at least one $R^1$ is H.

26. A composition of claim 24 where B is selected from a ring having all C atoms and a ring having one heteroatom, each being optionally substituted.

* * * * *